(12) United States Patent
Dochnahl et al.

(10) Patent No.: US 9,556,141 B2
(45) Date of Patent: *Jan. 31, 2017

(54) PROCESS FOR PREPARING N-SUBSTITUTED 1H-PYRAZOLE-5-CARBOXYLATE COMPOUNDS AND DERIVATIVES THEREOF

(71) Applicant: BASF SE, Ludwigshafen (DE)

(72) Inventors: Maximilian Dochnahl, Mannheim (DE); Karsten Koerber, Eppelheim (DE); Prashant Deshmukh, Mannheim (DE); Florian Kaiser, Mannheim (DE); Michael Rack, Eppelheim (DE); Timo Frassetto, Mannheim (DE); Gemma Veitch, Basel (CH)

(73) Assignee: BASF SE, Ludwigshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/359,446

(22) PCT Filed: Nov. 20, 2012

(86) PCT No.: PCT/EP2012/073128
§ 371 (c)(1),
(2) Date: May 20, 2014

(87) PCT Pub. No.: WO2013/076092
PCT Pub. Date: May 30, 2013

(65) Prior Publication Data
US 2015/0087843 A1    Mar. 26, 2015

Related U.S. Application Data

(60) Provisional application No. 61/561,975, filed on Nov. 21, 2011.

(30) Foreign Application Priority Data

Nov. 21, 2011   (EP) .................................... 11189973

(51) Int. Cl.
C07D 401/14    (2006.01)
C07D 471/10    (2006.01)
C07D 401/04    (2006.01)

(52) U.S. Cl.
CPC ........... C07D 401/04 (2013.01); C07D 471/10 (2013.01)

(58) Field of Classification Search
CPC .............................. C07D 471/10; C07D 401/14
(Continued)

(56) References Cited

U.S. PATENT DOCUMENTS 8,513,260 B2    8/2013   Schwarz et al.
8,629,273 B2    1/2014   Schwarz et al.
(Continued)

FOREIGN PATENT DOCUMENTS

DE    102007003036    6/2008
EP         1265850    1/2007
(Continued)

OTHER PUBLICATIONS

Cho et al., "Synthesis of Pyrroloazepines. Facile Synthesis of 2-Sustituted Pyrrole Derivatives by the Phosgene Method", J. Heterocyclic Chem., vol. 34, No. 87, 1997, pp. 87-91.
(Continued)

Primary Examiner — Noble Jarrell
Assistant Examiner — Daniel Carcanague
(74) Attorney, Agent, or Firm — Brinks Gilson & Lione

(57) ABSTRACT

The present invention relates to a process for preparing an N-substituted 1H-pyrazole-5-carboxylate compound of the formula (I-A)

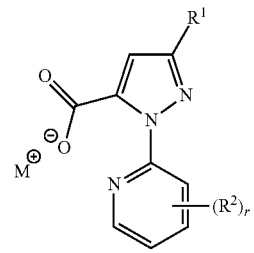

(I-A)

comprising the steps of
i) deprotonating a compound of the formula (II)

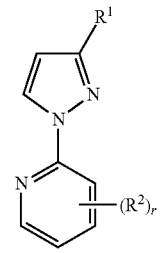

(II)

in which the variables $R^1$, $R^2$ and r are each as defined in the description and the claims,
with a magnesium-organic base having a carbon bound magnesium; and
ii) subjecting the product obtained in step (i) to a carbonylation by reacting it with a reagent selected from the group consisting carbon dioxide or a carbon dioxide equivalent, to obtain a compound of formula (I-A);
and it relates to further conversions to yield a N-substituted 1H-pyrazole-5-carbonyl chloride compound of the formula (I)

(Continued)

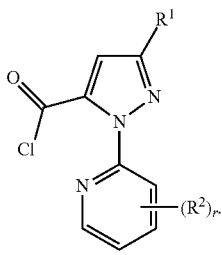

(I)

16 Claims, No Drawings

(58) Field of Classification Search
USPC ................................... 546/275.4; 514/406
See application file for complete search history.

(56) References Cited

U.S. PATENT DOCUMENTS

| | | | |
|---|---|---|---|
| 8,921,567 B2* | 12/2014 | Korber et al. | 546/278.4 |
| 9,006,485 B2 | 4/2015 | Koerber et al. | |
| 9,282,741 B2 | 3/2016 | Koerber et al. | |
| 2005/0075375 A1* | 4/2005 | Vourloumis et al. | 514/362 |
| 2009/0143228 A1* | 6/2009 | Kruger et al. | 504/100 |
| 2009/0181956 A1* | 7/2009 | Ikegami | C07D 207/34 514/227.8 |
| 2010/0144672 A1 | 6/2010 | Frackenpohl et al. | |
| 2011/0190365 A1 | 8/2011 | Werner et al. | |
| 2014/0155451 A1 | 6/2014 | Koerber et al. | |
| 2014/0163234 A1 | 6/2014 | Koerber et al. | |
| 2015/0087843 A1 | 3/2015 | Dochnahl et al. | |
| 2015/0216166 A1 | 8/2015 | Koerber et al. | |
| 2015/0237858 A1 | 8/2015 | Koerber et al. | |
| 2015/0250172 A1 | 9/2015 | Koerber et al. | |

FOREIGN PATENT DOCUMENTS

| | | |
|---|---|---|
| EP | 2 143 720 | 1/2010 |
| JP | 2007077106 | 3/2007 |
| WO | WO 01/70671 | 9/2001 |
| WO | WO 0170671 | 9/2001 |
| WO | WO 02/070483 | 9/2002 |
| WO | WO 03/015518 | 2/2003 |
| WO | WO 03/015519 | 2/2003 |
| WO | WO 03/016284 | 2/2003 |
| WO | WO 03/016300 | 2/2003 |
| WO | WO 03/024222 | 2/2003 |
| WO | WO 03015518 | 2/2003 |
| WO | WO 03015519 | 2/2003 |
| WO | WO 03016284 | 2/2003 |
| WO | WO 03016300 | 2/2003 |
| WO | WO 03024222 | 3/2003 |
| WO | WO 2006/000336 | 1/2006 |
| WO | WO 2006/068669 | 1/2006 |
| WO | WO 2006000336 | 1/2006 |
| WO | WO 2007/006670 | 1/2007 |
| WO | WO 2007/043677 | 4/2007 |
| WO | WO 2007043677 | 4/2007 |
| WO | WO 2008/011131 | 1/2008 |
| WO | WO 2008011131 | 1/2008 |
| WO | WO 2008/130021 | 4/2008 |
| WO | WO 2008/077483 | 7/2008 |
| WO | WO 2008130021 | 10/2008 |
| WO | WO 2009/156090 | 12/2009 |
| WO | WO 2010/017902 | 2/2010 |
| WO | WO 2010/136145 | 12/2010 |
| WO | WO 2011/057984 | 5/2011 |
| WO | WO 2011/064188 | 6/2011 |
| WO | WO 2013/024007 | 2/2013 |
| WO | WO 2013/024008 | 2/2013 |
| WO | WO 2013/024009 | 2/2013 |
| WO | WO 2013/024010 | 2/2013 |
| WO | WO 2013/073092 | 5/2013 |
| WO | WO 2013/113789 | 8/2013 |
| WO | WO 2013/144213 | 10/2013 |
| WO | WO 2013/164295 | 11/2013 |
| WO | WO 2013/174645 | 11/2013 |
| WO | WO 2014/053395 | 4/2014 |
| WO | WO 2014/053396 | 4/2014 |
| WO | WO 2014/053401 | 4/2014 |
| WO | WO 2014/053402 | 4/2014 |
| WO | WO 2014/053403 | 4/2014 |
| WO | WO 2014/053404 | 4/2014 |
| WO | WO 2014/053405 | 4/2014 |
| WO | WO 2014/053406 | 4/2014 |
| WO | WO 2014/053407 | 4/2014 |
| WO | WO 2014/079820 | 5/2014 |
| WO | WO 2014/128136 | 8/2014 |
| WO | WO 2014/128188 | 8/2014 |
| WO | WO 2014/154807 | 10/2014 |
| WO | WO2014/184343 | 11/2014 |

OTHER PUBLICATIONS deGroot et al., "Synthesis and Photoisomerisation of 2,3.17,18,22-pentamethyl-10,23-dihydro-1,19-[21$H$,24$H$]-bilindione, an unsymmetrical bilirubin model compound", Journal of the Royal Netherlands Chemical Society, vol. 101, No. 6, 1982, pp. 219-223.

Liu et al., "Design, Synthesis and Insecticidal Evaluation of Novel Pyrazolecarboxamides Containing Cyano Substituted N-Pyridylpyrazole", Chin. J. Chem., vol. 28, 2010, pp. 1757-1760.

Clark, David A. et al., "Synthesis of insecticidal fluorinated anthranilic diamides" Bioorganic & Medicinal Chemistry, 2008, p. 3163-3170, vol. 16.

Gschwend, Heinz W., et al., "Heteroatom-Facilitated Lthiations", H.R. Organic Reactions, 1979, p. 1-111, vol. 26.

Lahm, George P., et al., "Rynaxypyre: A new insecticidal anthranilic diamide that acts as a potent and selective ryanodine receptor activator", Bioorganic & Medicinal Chemistry Letters, 2007, p. 6274-6279, vol. 17.

Micetech, Ronald. G., et al. "The sequential lithiation of 1-phenylpyrazoles", Heterocycles, 1985, p. 943-951, vol. 23, No. 4.

Mutule, Ilga, et al. "Arylzinc species by microwave assisted Gringnard formation—transmetallation sequence: application in the Negishi coupling", Tetrahedron, 2005, p. 11168-11176, vol. 61.

Purandare, Ashok V. et al., "Pyrazole inhibitors of coactivator associated arginine methyltransferase 1 (CARM1)", Bioorganic & Medicinal Chemistry Letters, 2008, p. 4438-4441, vol. 18.

Tertov, B.A., et al. "Reactions of N-substituted diazoles and their halo derivatives with naphthyllithium and naphthylsodium", translated from Khimiya Geterotsiklicheskikh, Soedinenii, Mar. 1975, pp. 392-395, No. 3.

International Search Report dated Dec. 19, 2012,prepared in International Application No. PCT/EP2012/073128.

International Preliminary Report on Patentability dated May 27, 2014, prepared in International Application No. PCT/EP2012/073128.

Hongyun, Fong et al. "Research Progress on New-type Organomagnesium Reagents", Chemistry Online 2005, vol. 68, No. 1, p. 8-12.

Aggarwal et al., "Synthesis and antibacterial activity of some new 1-heteroaryl-5-amino-3Hlmethyl-4-phenylpyrazoles", Bioorganic & Medicinal Chemistry, vol. 14, 2006, pp. 1785-1791.

Caira, Mino R., "Crystalline Polymorphism of Organic Compounds", Topics in Current Chemistry, vol. 198, 1998, pp. 164-208.

Clark, David A., *"Synthesis of insecticidal fluorinated anthranilic diamides", Bioorganic & Medicinal Chemistry, 2008, p. 3163-3170, vol. 16.

Clososki, G.C., "Direct Magnesiation of Polyfuncionalized arenes and heteroarenes using (tmp)2Mg•2LiCl**", Angnew Chem Int. Ed. 2007, vol. 46, p. 7681-7684.

(56) References Cited

OTHER PUBLICATIONS

Despotopoulou, C, et al. "Synthesis of Fully Substituted Pyrazoles via Regio-and chemoselective Metalations", Organic Letters, 2009, p. 3326-3329, vol. 11, No. 15.
Dymek et al., "Synthesa I Badania Pochodnych Pirazolu", Acta Poloniae Pharamaceutica, vol. 25, No. 4, Jan. 1, 1968, pp. 375-382, compounds XXVII and XXVIII on p. 381.
Gschwend, Heinz W., et al. "Heteroaton-Faciliated Lithions", Organic Reactions, 1979, p. 6-105.
Haag, B. et al. "Regio and Chemoselctive metalation of arenes and heteroarenes using hindered metal amide bases", Angnew Chem Int. Ed, 2011, p. 9794-9824, vol. 50.
Henderson, Kenneth W., et al. "Magnesium Bisamides as reagents in synthesis", Chem Eur. J., 2001, p. 3430-3437, vol. 7.
Krasovskiy, Arkady et al. "Mixed Mg/Li amides of the type R2NMgCl•LiCL as highly efficient bases for the regioslective generation of functionalized aryl and heteroaryl magnesium compounds", Anggew, Chem. Int. Ed. 2006, p. 2958-2961, vol. 45.
Lahm, George P., et al. "Insecticidal anthranilic diamides: A new class of potent ryanodine receptor activators", Bioorganic & Medicinal Chemistry Letters, 2005, p. 4898-4906, vol. 15.
Lahm, George P., et al., "Rynaxypyre: A new insecticidal anthranilic diamide that acts as a potent and selective ryanodine receptor activator", Bioorganic & Medicinal Chemistry Letters 17 (2007) 6274-6279.
Micetich, Ronald G., et al. "The sequential Lithiated of 1-phenylpyrasoles", Heterocycles, 1985, vol. 23, No. 4, p. 943-951.
Purandare, Ashok V., et al. "Pyrazole inhibitors of coactivator associated arginine methyltransferase 1 (CARM1)", Bioorganic & Medicinal Chemistry Letters, 2008, p. 4438-4441, vol. 18.
Shilai, Manabu et al. "Selective metalation of thiophene and thiazole rings with magnesium amide base", J. ChemSoc. Perkin Trans. 2001, p. 442-444, vol. 1.
Tertov, B.A., et al. "Reaction of N-substituted Diazoles and their halo derivatives with naphthyllithium and naphthylsodium", Rostov State University, Rostov-on-Don, Translated from Khimiya Geterotsiklicheskikh Soedinenii, Mar. 1975, p. 395-395, No. 3.
Winters et al., "Synthesis of Fused Isoquinolinones by Thermal Cyclization of Beta-Phenyl-Alpha-Substituted Amino Heterocyclic Compounds", Tetrahedron Letters, No. 44, Jan. 1, 1975, pp. 3877-3878.
Office action dated Aug. 1, 2016 from U.S. Appl. No. 14/890,711, filed Nov. 12, 2015.

* cited by examiner

PROCESS FOR PREPARING N-SUBSTITUTED 1H-PYRAZOLE-5-CARBOXYLATE COMPOUNDS AND DERIVATIVES THEREOF

This application is a National Stage application of International Application No. PCT/EP2012/073128, filed Nov. 20, 2012, which claims the benefit of U.S. Provisional Application No. 61/561,975, filed Nov. 21, 2011, the entire contents of which are hereby incorporated herein by reference. This application also claims priority under 35 U.S.C. §119 to European Patent Application No. 11189973.8, filed Nov. 21, 2011, the entire contents of which is hereby incorporated herein by reference.

The present invention relates to a process for preparing N-substituted 1H-pyrazole-5-carboxylate compounds and derivatives thereof, in particular the corresponding carbonylchloride compounds (acid chlorides). It also relates to the use of these acid chlorides for preparing anthranilamide derivatives that are useful pesticides.

N-substituted 1H-pyrazole-5-carboxylate compounds and the corresponding acid chlorides, in particular substituted 1-pyridin-2-yl-1H-pyrazole-5-carbonylchlorides are important precursors for anthranilamide derivates that carry a 1-pyridin-2-yl-1H-pyrazol-5-yl-carbonyl substituent at the aromatic amino group. Such compounds find use as pesticides, especially as insecticides, which are disclosed, for example, in WO 01/70671, WO 03/015518, WO 03/015519, WO 03/016284, WO 03/016300, WO 03/024222, WO 06/000336; WO 06/068669, WO 07/043,677 and WO 08/130,021.

For preparation of substituted 1-pyridin-2-yl-1H-pyrazole-5-carbonylchlorides, a process described in WO 02/070483, WO03/015519, WO 07/043,677 and WO 08/130,021 has been found to be useful. It is based on the deprotonation of a 1-pyridin-2-yl-1H-pyrazole compound with either n-butyl lithium or lithium diisoproylamide, followed by reacting the resulting lithiated species with carbon dioxide to the corresponding carboxylic acid, which is subsequently chlorinated using a dehydrative chlorinating agent such as thionyl chloride or oxalyl chloride to give the corresponding acid chloride. Similar synthetic routes that all require the formation of the pyrazole-5-carboxylic acid as an intermediate are described for example in: Khimiya Geterotsiklicheskikh Soedinenii 1975, 3, 392-395; Heterocycles 1985, 23, 943-951; Bioorganic & Medicinal Chemistry Letters 2005, 15, 4898-4906; WO 06/000336; WO 06/068669; Bioorganic & Medicinal Chemistry Letters 2007, 17, 6274-6279; Bioorganic & Medicinal Chemistry 2008, 16, 3163-3170; Organic Reactions 1979, 26; Bioorganic & Medicinal Chemistry Letters 2008, 18, 4438-4441 and WO 08/011,131.

However, these procedures of the prior art suffer from several limitations rendering them hardly suitable for industrial scale production. For instance, the application of the highly reactive organolithium bases, such as lithium butyllithium, phenyllithium or lithium diisopropylamide, for the deprotonation of pyrazoles represents a potentially hazardous step in the synthesis, in particular if performed on a large scale. Moreover, these organolithium bases are very expensive and require the very low reaction temperatures, which in itself already results in excessive energy costs. Additionally, a conversion of 1-pyridin-2-yl-1H-pyrazole compounds to the corresponding pyrozole-5-carboxylic acid chloride in less than the four steps required by the known procedures, would be highly desirable, as every synthetic step is time and energy consuming and leads to a loss of material.

It is an object of the present invention to provide processes for preparing N-substituted 1H-pyrazole-5-carboxylate and N-substituted 1H-pyrazole-5-carbonylchloride compounds and for preparing pyrazolecarboxamides of anthranilamides derived therefrom. These processes should be simple to carry out, require 4 or 3 or less steps and be suitable for the industrial scale production. They should additionally be inexpensive and safe and be based on selective reactions.

The object is achieved by the processes described in detail hereinafter.

A first aspect of the present invention relates to a process for preparing an N-substituted 1H-pyrazole-5-carboxylate compound of the formula (I-A)

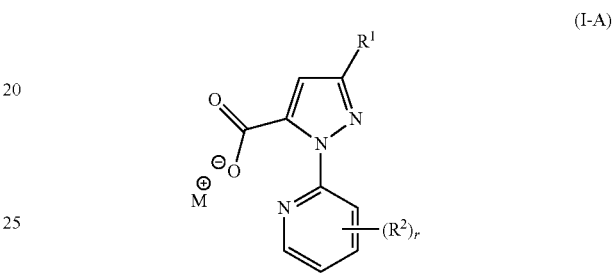

in which $R^1$ is selected from hydrogen, halogen, cyano, —$SF_5$, $C_1$-$C_6$-alkyl, $C_1$-$C_6$-fluoroalkyl, $CBrF_2$, $C_3$-$C_8$-cycloalkyl, $C_3$-$C_8$-fluorocycloalkyl, $C_2$-$C_6$-alkenyl, $C_2$-$C_6$-fluoroalkenyl, wherein the six last mentioned radicals may be substituted by one or more radicals $R^a$; —$Si(R^f)_2R^g$, —$OR^b$, —$SR^b$, —$S(O)_mR^b$, —$S(O)_nN(R^c)R^d$, —$N(R^{c1})R^{d1}$, phenyl which may be substituted by 1, 2, 3, 4 or 5 radicals $R^e$, and a 3-, 4-, 5-, 6- or 7-membered saturated, partially unsaturated or aromatic heterocyclic ring containing 1, 2 or 3 heteroatoms or heteroatom groups selected from N, O, S, NO, SO and $SO_2$, as ring members, where the heterocyclic ring may be substituted by one or more radicals $R^e$;

each $R^2$ is independently selected from the group consisting of halogen, $SF_5$, $C_1$-$C_6$-alkyl, $C_1$-$C_6$-fluoroalkyl, $C_3$-$C_8$-cycloalkyl, $C_3$-$C_8$-fluorocycloalkyl, $C_2$-$C_6$-alkenyl, $C_2$-$C_6$-fluoroalkenyl, wherein the six last mentioned radicals may be substituted by one or more radicals $R^a$; —$Si(R^f)_2R^g$, —$OR^b$, —$SR^b$, —$S(O)_mR^b$, —$S(O)_nN(R^c)R^d$, —$N(R^{c1})R^{d1}$, phenyl which may be substituted by 1, 2, 3, 4 or 5 radicals $R^e$, and a 3-, 4-, 5-, 6- or 7-membered saturated, partially unsaturated or completely unsaturated heterocyclic ring containing 1, 2 or 3 heteroatoms or heteroatom groups selected from N, O, S, NO, SO and $SO_2$, as ring members, where the heterocyclic ring may be substituted by one or more radicals $R^e$;

$R^a$ is selected from the group consisting $SF_5$, $C_1$-$C_6$-alkyl, $C_1$-$C_6$-fluoroalkyl, $C_1$-$C_6$-alkoxy-$C_1$-$C_6$-alkyl, $C_3$-$C_8$-cycloalkyl, $C_3$-$C_8$-fluorocycloalkyl, $C_2$-$C_6$-alkenyl, $C_2$-$C_6$-fluoroalkenyl, —$Si(R^f)_2R^g$, —$OR^b$, —$SR^b$, —$S(O)_mR^b$, —$S(O)_nN(R^c)R^d$, —$N(R^{c1})R^{d1}$, phenyl which may be substituted by 1, 2, 3, 4 or 5 radicals $R^e$, and a 3-, 4-, 5-, 6- or 7-membered saturated, partially unsaturated or completely unsaturated heterocyclic ring containing 1, 2 or 3 heteroatoms or heteroatom groups selected from N, O, S, NO, SO and $SO_2$, as ring members, where the heterocyclic ring may be substituted by one or more radicals $R^e$;

or two geminally bound radicals $R^a$ together form a group selected from =$CR^hR^i$, =$NR^{c1}$, =$NOR^b$ and =$NNR^{c1}$;

or two radicals $R^a$, together with the carbon atoms to which they are bound, form a 3-, 4-, 5-, 6-, 7- or 8-membered saturated or partially unsaturated carbocyclic or heterocyclic ring containing 1, 2 or 3 heteroatoms or heteroatom groups selected from N, O, S, NO, SO and $SO_2$, as ring members;

wherein, in the case of more than one $R^a$, $R^a$ can be identical or different;

$R^b$ is selected from the group consisting of $C_1$-$C_6$-alkyl, $C_1$-$C_6$-fluoroalkyl, $C_2$-$C_6$-alkenyl, $C_2$-$C_6$-fluoroalkenyl, $C_3$-$C_8$-cycloalkyl, $C_3$-$C_8$-fluorocycloalkyl, wherein the six last mentioned radicals may optionally carry 1 or 2 radicals selected from $C_1$-$C_6$-alkoxy, $C_1$-$C_6$-fluoroalkoxy, $C_1$-$C_6$-alkylthio, $C_1$-$C_6$-fluoroalkylthio, $C_1$-$C_6$-alkylsulfinyl, $C_1$-$C_6$-fluoroalkylsulfinyl, $C_1$-$C_6$-alkylsulfonyl, $C_1$-$C_6$-fluoroalkylsulfonyl, —Si$(R^f)_2R^g$, phenyl, benzyl, pyridyl and phenoxy, wherein the four last mentioned radicals may be unsubstituted, partially or fully halogenated and/or may carry 1, 2 or 3 substituents selected from the group consisting of $C_1$-$C_6$-alkyl, $C_1$-$C_6$-fluoroalkyl, $C_1$-$C_6$-alkoxy and $C_1$-$C_6$-fluoroalkoxy;

wherein, in the case of more than one $R^b$, $R^b$ can be identical or different;

$R^c$, $R^d$ are, independently from one another and independently of each occurrence, selected from the group consisting of cyano, $C_1$-$C_6$-alkyl, $C_1$-$C_6$-fluoroalkyl, $C_2$-$C_6$-alkenyl, $C_2$-$C_6$-fluoroalkenyl, $C_3$-$C_8$-cycloalkyl, $C_3$-$C_8$-fluorocycloalkyl, wherein the six last mentioned radicals may optionally carry 1 or 2 radicals selected from $C_1$-$C_6$-alkoxy, $C_1$-$C_6$-fluoroalkoxy, $C_1$-$C_6$-alkylthio, $C_1$-$C_6$-fluoroalkylthio, $C_1$-$C_6$-alkylsulfinyl, $C_1$-$C_6$-alkylsulfonyl, —Si$(R^f)_2R^g$, phenyl, benzyl, pyridyl and phenoxy, wherein the four last mentioned radicals may be unsubstituted, partially or fully halogenated and/or may carry 1, 2 or 3 substituents selected from the group consisting of $C_1$-$C_6$-alkyl, $C_1$-$C_6$-fluoroalkyl, $C_1$-$C_6$-alkoxy and $C_1$-$C_6$-fluoroalkoxy;

or $R^c$ and $R^d$, together with the nitrogen atom to which they are bound, form a 3-, 4-, 5-, 6- or 7-membered saturated, partly unsaturated or completely unsaturated heterocyclic ring which may contain 1 or 2 further heteroatoms selected from N, O and S as ring members, where the heterocyclic ring may carry 1, 2, 3 or 4 substituents selected from halogen, $C_1$-$C_4$-alkyl, $C_1$-$C_4$-fluoroalkyl, $C_1$-$C_4$-alkoxy and $C_1$-$C_4$-fluoroalkoxy;

$R^{c1}$ is hydrogen or has one of the meanings given for $R^c$;

$R^{d1}$ is hydrogen or has one of the meanings given for $R^d$;

$R^e$ is selected from the group consisting of halogen, $C_1$-$C_6$-alkyl, $C_1$-$C_6$-fluoroalkyl, $C_2$-$C_6$-alkenyl, $C_2$-$C_6$-fluoroalkenyl, $C_3$-$C_8$-cycloalkyl, $C_3$-$C_8$-fluorocycloalkyl, where the six last mentioned radicals may optionally carry 1 or 2 radicals selected from $C_1$-$C_4$-alkoxy; $C_1$-$C_6$-alkoxy, $C_1$-$C_6$-fluoroalkoxy, $C_1$-$C_6$-alkylthio, $C_1$-$C_6$-fluoroalkylthio, $C_1$-$C_6$-alkylsulfinyl, $C_1$-$C_6$-fluoroalkylsulfinyl, $C_1$-$C_6$-alkylsulfonyl, $C_1$-$C_6$-fluoroalkylsulfonyl, —Si$(R^f)_2R^g$, phenyl, benzyl, pyridyl and phenoxy, wherein the four last mentioned radicals may be unsubstituted, partially or fully halogenated and/or may carry 1, 2 or 3 substituents selected from the group consisting of $C_1$-$C_6$-alkyl, $C_1$-$C_6$-fluoroalkyl, $C_1$-$C_6$-alkoxy and $C_1$-$C_6$-fluoroalkoxy;

wherein, in the case of more than one $R^e$, $R^e$ can be identical or different;

$R^f$, $R^g$ are, independently of each other and independently of each occurrence, selected from the group consisting of $C_1$-$C_4$-alkyl, $C_3$-$C_6$-cycloalkyl, $C_1$-$C_4$-alkoxy-$C_1$-$C_4$-alkyl, phenyl and benzyl;

$R^h$, $R^i$ are, independently from one another and independently of each occurrence, selected from the group consisting of hydrogen, halogen, $SF_5$, $C_1$-$C_6$-alkyl, $C_1$-$C_6$-fluoroalkyl, $C_2$-$C_6$-alkenyl, $C_2$-$C_6$-fluoroalkenyl, $C_3$-$C_8$-cycloalkyl, $C_3$-$C_8$-fluorocycloalkyl, where the six last mentioned radicals may optionally carry 1 or 2 radicals selected from $C_1$-$C_4$-alkyl and $C_1$-$C_4$-fluoroalkyl; $C_1$-$C_6$-alkoxy, $C_1$-$C_6$-fluoroalkoxy, $C_1$-$C_6$-alkylthio, $C_1$-$C_6$-fluoroalkylthio, $C_1$-$C_6$-alkylsulfinyl, $C_1$-$C_6$-alkylsulfonyl, —Si$(R^f)_2R^g$, phenyl, benzyl, pyridyl and phenoxy, wherein the four last mentioned radicals may be unsubstituted, partially or fully halogenated and/or may carry 1, 2 or 3 substituents selected from the group consisting of $C_1$-$C_6$-alkyl, $C_1$-$C_6$-fluoroalkyl, $C_1$-$C_6$-alkoxy, $C_1$-$C_6$-fluoroalkoxy, ($C_1$-$C_6$-alkoxy)carbonyl, ($C_1$-$C_6$-alkyl)amino and di-($C_1$-$C_6$-alkyl)amino;

m is 1 or 2, wherein, in the case of several occurrences, m may be identical or different;

n is 0, 1 or 2; wherein, in the case of several occurrences, n may be identical or different;

r is 0, 1, 2, 3 or 4;

$M^+$ is a cation or cation equivalent compensating the charge of the carboxylate;

comprising the steps of i) deprotonating a compound of the formula (II)

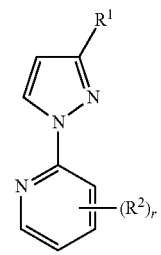

(II)

in which the variables $R^1$, $R^2$ and r are each as defined above, with a magnesium-organic base having a carbon bound magnesium; and ii) subjecting the product obtained in step (i) to a carboxylation by reacting it with carbon dioxide or a carbon dioxide equivalent, to obtain a compound of formula (I-A).

A further aspect of the present invention relates to a process for preparing an N-substituted 1H-pyrazole-5-carboxylate compound of the formula (I-A) as described herein, wherein the carboxylate compound of formula I-A is further converted in a step (ii-a) to the corresponding carbonylchloride compound of formula (I):

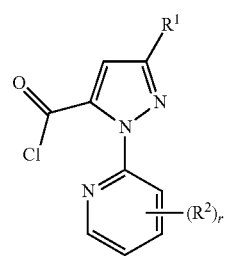

(I)

in which the variables $R^1$, $R^2$ and r are each as defined herein.

A further aspect of the present invention relates to a process for preparing an N-substituted 1H-pyrazole-5-carboxylate compound of the formula (I-A) as described herein, wherein the carboxylate compound of formula I-A is further converted in a step (ii-b) to the corresponding acid compound (I-B):

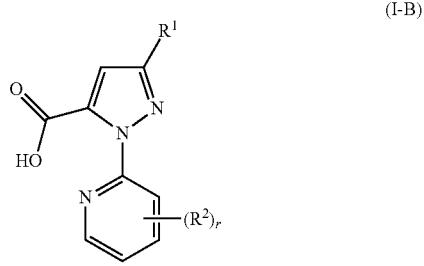

in which the variables $R^1$, $R^2$ and r are each as defined herein, and
wherein the acid compound (I-B) is optionally further converted in a step (ii-c) to the corresponding carbonylchloride compound (I):

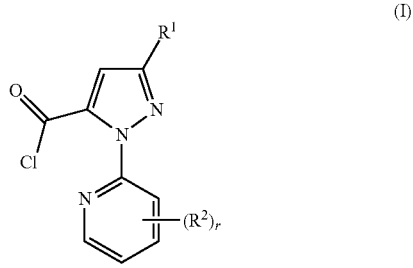

in which the variables $R^1$, $R^2$ and r are each as defined herein.

The preceding processes of the invention are associated with a series of advantages as they overcome the aforementioned shortcomings of the prior art processes. For instance, the process according to the invention enables the preparation of N-substituted 1H-pyrazole-5-carboxylate compounds of the formula (I-A) de facto in one process step, since the deprotonated intermediate obtained after reaction step i) is converted in-situ without prior work-up or purification into the product of formula (I-A). The processes of the invention further enable the preparation of N-substituted 1H-pyrazole-5-carbonylchloride compounds of the formula (I) via useful intermediates of formula I-A respectively I-A and I-B. The intermediate of formula I-A can be isolated or can be further converted directly to a compound of formula I or to a compound of formula I-B, with or without prior work-up or purification. The intermediate of formula I-B can be converted to a compound of formula I with or without prior work-up or purification. If the processes are without work-up or purification steps, the preparation of carbonylchloride compounds of the formula (I) is done de facto in one process step. This prevents losses during work-up or purification, and this also saves time, resources and/or energy. Also, after completion of the conversion the acid chloride I can be readily isolated and purified by means of a simple protocol including crystallization and solvent evaporation to remove unwanted byproducts. Furthermore, the deprotonation step is carried out with an inexpensive Grignard reagent, which allows for selective and high-yielding conversions at moderate temperatures that can be safely and smoothly carried out on an industrial scale.

Advantages of the processes of the present invention are that the processes can be run at moderate temperatures and with safe and inexpensive reagents, which is favourable in view of costs and safety aspects. The yields are generally high, and that there are only few by-products, which saves time, resources and energy. Due to these properties, the processes are therefore suitable for an industrial scale, which is a further advantage.

A further aspect of the invention relates to a process for preparing a sulfimine compound of formula (VI)

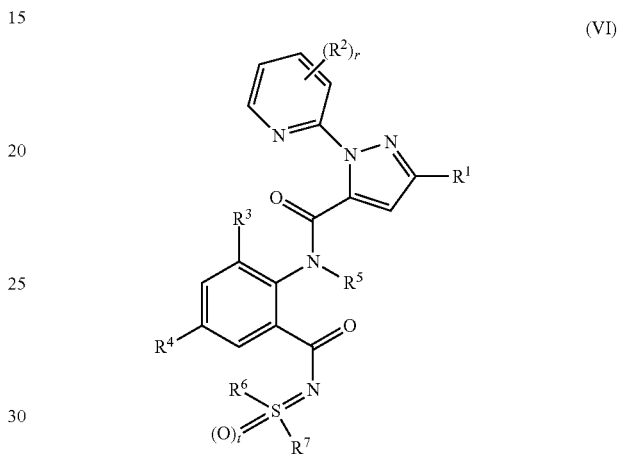

in which
$R^1$, $R^2$ and r are each as defined herein and in the claims;
$R^3$ and $R^4$ are independently selected from the group consisting of halogen, cyano, azido, nitro, —SCN, $SF_5$, $C_1$-$C_6$-alkyl, $C_1$-$C_6$-haloalkyl, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl, wherein the eight last mentioned radicals may be substituted by one or more radicals $R^a$, —Si$(R^f)_2R^g$, —OR$^{b1}$, —OS(O)$_n$R$^{b1}$, SR$^{b1}$, —S(O)$_m$R$^{b1}$, —S(O)$_n$N(R$^{b1}$)R$^{d1}$, —N(R$^{c1}$)R$^{d1}$, —N(R$^{c1}$)C(=O)R$^a$, —C(=O)R$^a$, —C(=O)OR$^{b1}$, —C(=S)R$^a$, —C(=S)OR$^{b1}$, —C(=NR$^{c1}$)R$^a$, —C(=O)N(R$^{c1}$)R$^{d1}$, —C(=S)N(R$^{c1}$)R$^{d1}$, phenyl which may be substituted by 1, 2, 3, 4 or 5 radicals $R^e$, and a 3-, 4-, 5-, 6- or 7-membered saturated, partially unsaturated or completely unsaturated heterocyclic ring containing 1, 2 or 3 heteroatoms or heteroatom groups selected from N, O, S, NO, SO and $SO_2$, as ring members, where the heterocyclic ring may be substituted by one or more radicals $R^e$;
$R^5$ is selected from the group consisting of hydrogen; cyano; $C_1$-$C_{10}$-alkyl, $C_1$-$C_{10}$-haloalkyl, $C_3$-$C_8$-cycloalkyl, $C_3$-$C_8$-halocycloalkyl, $C_2$-$C_{10}$-alkenyl, $C_2$-$C_{10}$-haloalkenyl, $C_2$-$C_{10}$-alkynyl, $C_2$-$C_{10}$-haloalkynyl, wherein the eight last radicals may optionally be substituted by one or more radicals $R^a$; —N(R$^{c1}$)R$^{d1}$; Si$(R^f)_2R^g$; —OR$^{b1}$; —SR$^{b1}$; —S(O)$_m$R$^{b1}$; —S(O)$_n$N(R$^{c1}$)R$^{d1}$; —C(=O)R$^a$; —C(=O)OR$^{b1}$; —C(=O)N(R$^{c1}$)R$^{d1}$; —C(=S)R$^a$; —C(=S)OR$^{b1}$; —C(=S)N(R$^{c1}$)R$^{d1}$; —C(=NR$^{c1}$)R$^a$; phenyl which may be substituted by 1, 2, 3, 4 or 5 radicals $R^e$; and a 3-, 4-, 5-, 6- or 7-membered saturated, partially unsaturated or completely unsaturated heterocyclic ring containing 1, 2 or 3 heteroatoms or heteroatom groups selected from N, O, S, NO, SO and $SO_2$, as ring members, where the heterocyclic ring may be substituted by one or more radicals $R^e$;

$R^6$ and $R^7$ are selected independently of one another from the group consisting of hydrogen, $C_1$-$C_{10}$-alkyl, $C_1$-$C_{10}$-haloalkyl, $C_3$-$C_8$-cycloalkyl, $C_3$-$C_8$-halocycloalkyl, $C_2$-$C_{10}$-alkenyl, $C_2$-$C_{10}$-haloalkenyl, $C_2$-$C_{10}$-alkynyl, $C_2$-$C_{10}$-haloalkynyl, wherein the eight last radicals may optionally be substituted by one or more radicals $R^a$;

or $R^6$ and $R^7$ together represent a $C_2$-$C_7$-alkylene, $C_2$-$C_7$-alkenylene or $C_6$-$C_9$-alkynylene chain forming together with the sulfur atom to which they are attached a 3-, 4-, 5-, 6-, 7-, 8-, 9- or 10-membered saturated, partially unsaturated or completely unsaturated ring, wherein 1 to 4 of the $CH_2$ groups in the $C_2$-$C_7$-alkylene chain or 1 to 4 of any of the $CH_2$ or CH groups in the $C_6$-$C_7$-alkenylene chain or 1 to 4 of any of the $CH_2$ groups in the $C_6$-$C_9$-alkynylene chain may be replaced by 1 to 4 groups independently selected from the group consisting of C=O, C=S, O, S, N, NO, SO, $SO_2$ and NH, and wherein the carbon and/or nitrogen atoms in the $C_2$-$C_7$-alkylene, $C_2$-$C_7$-alkenylene or $C_6$-$C_9$-alkynylene chain may be substituted with 1 to 5 substituents independently selected from the group consisting of halogen, cyano, $C_1$-$C_6$-alkyl, $C_1$-$C_6$-haloalkyl, $C_1$-$C_6$-alkoxy, $C_1$-$C_6$-haloalkoxy, $C_1$-$C_6$-alkylthio, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl; said substituents being identical or different from one another if more than one substituent is present;

$R^a$, $R^{c1}$, $R^{d1}$, $R^e$, $R^f$, $R^g$, m and n are each as defined herein and in the claims;

$R^{b1}$ is hydrogen or has one of the meanings given herein and in the claims for $R^b$; and t is 0 or 1;

which comprises providing a compound of the formula (I) by a process defined herein and in the claims and subsequently the step of iii) reacting the compound of the formula (I) with a compound of the formula (VII)

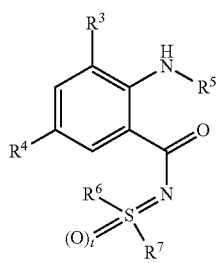

(VII)

in which the variables $R^3$, $R^4$, $R^5$, $R^6$, $R^7$ and t are each as defined above, optionally in the presence of a base, to obtain a compound of the formula VI.

In the context of the present invention, the terms used generically are each defined as follows:

The prefix $C_x$-$C_y$ refers in the particular case to the number of possible carbon atoms.

The term "halogen" denotes in each case fluorine, bromine, chlorine or iodine, in particular fluorine, chlorine or bromine.

The term "partially or fully halogenated" will be taken to mean that 1 or more, e.g. 1, 2, 3, 4 or 5 or all of the hydrogen atoms of a given radical have been replaced by a halogen atom, in particular by fluorine or chlorine.

The term "alkyl" as used herein (and in the alkyl moieties of other groups comprising an alkyl group, e.g. alkoxy, alkylcarbonyl, alkylthio, alkylsulfinyl, alkylsulfonyl and alkoxyalkyl) denotes in each case a straight-chain or branched alkyl group having usually from 1 to 10 carbon atoms, frequently from 1 to 6 carbon atoms, preferably 1 to 4 carbon atoms and in particular from 1 to 3 carbon atoms. Examples of an alkyl group are methyl, ethyl, n-propyl, iso-propyl, n-butyl, 2-butyl, iso-butyl, tert-butyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl, n-heptyl, 1-methylhexyl, 2-methylhexyl, 3-methylhexyl, 4-methylhexyl, 5-methylhexyl, 1-ethylpentyl, 2-ethylpentyl, 3-ethylpentyl, n-octyl, 1-methyloctyl, 2-methylheptyl, 1-ethylhexyl, 2-ethylhexyl, 1,2-dimethylhexyl, 1-propylpentyl and 2-propylpentyl.

The term "alkylene" (or alkanediyl) as used herein in each case denotes an alkyl radical as defined above, wherein one hydrogen atom at any position of the carbon backbone is replaced by one further binding site, thus forming a bivalent moiety.

The term "haloalkyl" as used herein (and in the haloalkyl moieties of other groups comprising a haloalkyl group, e.g. haloalkoxy and haloalkylthio) denotes in each case a straight-chain or branched alkyl group having usually from 1 to 10 carbon atoms, frequently from 1 to 6 carbon atoms, wherein the hydrogen atoms of this group are partially or totally replaced with halogen atoms. Preferred haloalkyl moieties are selected from $C_1$-$C_4$-haloalkyl, more preferably from $C_1$-$C_2$-haloalkyl, more preferably from halomethyl, in particular from $C_1$-$C_2$-fluoroalkyl such as fluoromethyl, difluoromethyl, trifluoromethyl, 1-fluoroethyl, 2-fluoroethyl, 2,2-difluoroethyl, 2,2,2-trifluoroethyl, pentafluoroethyl, and the like.

The term "fluoroalkyl", as used herein (and in the fluoroalkyl units of fluoroalkoxy, fluoroalkylthio, fluoroalkylsulfinyl and fluoroalkylsulfonyl) denotes in each case straight-chain or branched alkyl groups having usually from 1 to 10 carbon atoms, frequently from 1 to 6 carbon atoms and in particular 1 to 4 carbon atoms, wherein the hydrogen atoms of this group are partially or totally replaced with fluorine atoms. Examples thereof are fluoromethyl, difluoromethyl, trifluoromethyl, 1-fluoroethyl, 2-fluoroethyl, 2,2-difluoroethyl, 2,2,2-trifluoroethyl, pentafluoroethyl, 3,3,3-trifluoroprop-1-yl, 1,1,1-trifluoroprop-2-yl, heptafluoroisopropyl, 1-fluorobutyl, 2-fluorobutyl, 3-fluorobutyl, 4-fluorobutyl, 4,4,4-trifluorobutyl, fluoro-tert-butyl and the like.

The term "cycloalkyl" as used herein (and in the cycloalkyl moieties of other groups comprising a cycloalkyl group, e.g. cycloalkoxy and cycloalkylalkyl) denotes in each case a mono- or bicyclic cycloaliphatic radical having usually from 3 to 10 carbon atoms, 3 to 8 carbon atoms or 3 to 6 carbon atoms, such as cyclopropyl, cyclobutyl, cyclopentyl, cyclohexyl, cycloheptyl, cyclooctyl, bicyclo[2.1.1]hexyl, bicyclo[3.1.1]heptyl, bicyclo[2.2.1]heptyl, and bicyclo[2.2.2]octyl.

The term "halocycloalkyl" as used herein (and in the halocycloalkyl moieties of other groups comprising an halocycloalkyl group, e.g. halocycloalkylmethyl) denotes in each case a mono- or bicyclic cycloaliphatic radical having usually from 3 to 10 carbon atoms, 3 to 8 carbon atoms or 3 to 6 carbon atoms, wherein at least one, e.g. 1, 2, 3, 4 or 5 of the hydrogen atoms are replaced by halogen, in particular by fluorine or chlorine. Examples are 1- and 2-fluorocyclopropyl, 1,2-, 2,2- and 2,3-difluorocyclopropyl, 1,2,2-trifluorocyclopropyl, 2,2,3,3-tetrafluorocyclpropyl, 1- and 2-chlorocyclopropyl, 1,2-, 2,2- and 2,3-dichlorocyclopropyl, 1,2,2-trichlorocyclopropyl, 2,2,3,3-tetrachlorocyclpropyl, 1-, 2- and 3-fluorocyclopentyl, 1,2-, 2,2-, 2,3-, 3,3-, 3,4-, 2,5-difluorocyclopentyl, 1-, 2- and 3-chlorocyclopentyl, 1,2-, 2,2-, 2,3-, 3,3-, 3,4-, 2,5-dichlorocyclopentyl and the like.

The term "fluorocylcoalkyl" as used herein, denotes a halocycloalkyl radical, as defined above, wherein the one or more halogen atoms are fluorine atoms.

The term "alkenyl" as used herein denotes in each case a singly unsaturated hydrocarbon radical having usually 2 to 10, preferably 2 to 4 carbon atoms, e.g. vinyl, allyl (2-propen-1-yl), 1-propen-1-yl, 2-propen-2-yl, methallyl (2-methylprop-2-en-1-yl), 2-buten-1-yl, 3-buten-1-yl, 2-penten-1-yl, 3-penten-1-yl, 4-penten-1-yl, 1-methylbut-2-en-1-yl, 2-ethylprop-2-en-1-yl and the like.

The term "alkenylene" (or alkenediyl) as used herein in each case denotes an alkenyl radical as defined above, wherein one hydrogen atom at any position of the carbon backbone is replaced by one further binding site, thus forming a bivalent moiety.

The term "haloalkenyl" as used herein, which may also be expressed as "alkenyl which may be substituted by halogen", and the haloalkenyl moieties in haloalkenyloxy, haloalkenylcarbonyl and the like refers to unsaturated straight-chain or branched hydrocarbon radicals having 2 to 10 ("$C_2$-$C_{10}$-haloalkenyl") or 2 to 6 ("$C_2$-$C_6$-haloalkenyl") carbon atoms and a double bond in any position, where some or all of the hydrogen atoms in these groups are replaced by halogen atoms as mentioned above, in particular fluorine, chlorine and bromine, for example chlorovinyl, chloroallyl and the like.

The term "fluoroalkenyl" as used herein, denotes a haloalkenyl radical, as defined above, wherein the one or more halogen atoms are fluorine atoms.

The term "alkynyl" as used herein denotes unsaturated straight-chain or branched hydrocarbon radicals having usually 2 to 10, frequently 2 to 6, preferably 2 to 4 carbon atoms and one or two triple bonds in any position, e.g. ethynyl, propargyl (2-propyn-1-yl), 1-propyn-1-yl, 1-methylprop-2-yn-1-yl), 2-butyn-1-yl, 3-butyn-1-yl, 1-pentyn-1-yl, 3-pentyn-1-yl, 4-pentyn-1-yl, 1-methylbut-2-yn-1-yl, 1-ethylprop-2-yn-1-yl and the like.

The term "alkynylene" (or alkynediyl) as used herein in each case denotes an alkynyl radical as defined above, wherein one hydrogen atom at any position of the carbon backbone is replaced by one further binding site, thus forming a bivalent moiety.

The term "haloalkynyl" as used herein, which is also expressed as "alkynyl which may be substituted by halogen", refers to unsaturated straight-chain or branched hydrocarbon radicals having usually 3 to 10 carbon atoms, frequently 2 to 6, preferably 2 to 4 carbon atoms, and one or two triple bonds in any position (as mentioned above), where some or all of the hydrogen atoms in these groups are replaced by halogen atoms as mentioned above, in particular fluorine, chlorine and bromine.

The term "alkoxy" as used herein denotes in each case a straight-chain or branched alkyl group usually having from 1 to 10 carbon atoms, frequently from 1 to 6 carbon atoms, preferably 1 to 4 carbon atoms, which is bound to the remainder of the molecule via an oxygen atom. Examples of an alkoxy group are methoxy, ethoxy, n-propoxy, iso-propoxy, n-butyloxy, 2-butyloxy, iso-butyloxy, tert-butyloxy, and the like.

The term "haloalkoxy" as used herein denotes in each case a straight-chain or branched alkoxy group, as defined above, having from 1 to 10 carbon atoms, frequently from 1 to 6 carbon atoms, preferably 1 to 4 carbon atoms, preferably 1 to 3 carbon atoms, wherein the hydrogen atoms of this group are partially or totally replaced with halogen atoms, in particular fluorine atoms. Preferred haloalkoxy moieties include $C_1$-$C_4$-haloalkoxy, in particular halomethoxy, and also in particular $C_1$-$C_2$-fluoroalkoxy, such as fluoromethoxy, difluoromethoxy, trifluoromethoxy, 1-fluoroethoxy, 2-fluoroethoxy, 2,2-difluoroethoxy, 2,2,2-trifluoroethoxy, 2-chloro-2-fluoroethoxy, 2-chloro-2,2-difluoro-ethoxy, 2,2-dichloro-2-fluoroethoxy, 2,2,2-trichloroethoxy, pentafluoroethoxy and the like.

The term "alkoxy-alkyl" as used herein denotes in each case alkyl usually comprising 1 to 6 carbon atoms, preferably 1 to 4 carbon atoms, wherein 1 carbon atom carries an alkoxy radical usually comprising 1 to 10, frequently 1 to 6, in particular 1 to 4, carbon atoms as defined above. Examples are $CH_2OCH_3$, $CH_2$—$OC_2H_5$, n-propoxymethyl, $CH_2$—$OCH(CH_3)_2$, n-butoxymethyl, (1-methylpropoxy)-methyl, (2-methylpropoxy)methyl, $CH_2$—$OC(CH_3)_3$, 2-(methoxy)ethyl, 2-(ethoxy)ethyl, 2-(n-propoxy)-ethyl, 2-(1-methylethoxy)-ethyl, 2-(n-butoxy)ethyl, 2-(1-methylpropoxy)-ethyl, 2-(2-methylpropoxy)-ethyl, 2-(1,1-dimethylethoxy)-ethyl, 2-(methoxy)-propyl, 2-(ethoxy)-propyl, 2-(n-propoxy)-propyl, 2-(1-methylethoxy)-propyl, 2-(n-butoxy)-propyl, 2-(1-methylpropoxy)-propyl, 2-(2-methylpropoxy)-propyl, 2-(1,1-dimethylethoxy)-propyl, 3-(methoxy)-propyl, 3-(ethoxy)-propyl, 3-(n-propoxy)-propyl, 3-(1-methylethoxy)-propyl, 3-(n-butoxy)-propyl, 3-(1-methylpropoxy)-propyl, 3-(2-methylpropoxy)-propyl, 3-(1,1-dimethylethoxy)-propyl, 2-(methoxy)-butyl, 2-(ethoxy)-butyl, 2-(n-propoxy)-butyl, 2-(1-methylethoxy)-butyl, 2-(n-butoxy)-butyl, 2-(1-methylpropoxy)-butyl, 2-(2-methylpropoxy)-butyl, 2-(1,1-dimethylethoxy)-butyl, 3-(methoxy)-butyl, 3-(ethoxy)-butyl, 3-(n-propoxy)-butyl, 3-(1-methylethoxy)-butyl, 3-(n-butoxy)-butyl, 3-(1-methylpropoxy)-butyl, 3-(2-methylpropoxy)-butyl, 3-(1,1-dimethylethoxy)-butyl, 4-(methoxy)-butyl, 4-(ethoxy)-butyl, 4-(n-propoxy)-butyl, 4-(1-methylethoxy)-butyl, 4-(n-butoxy)-butyl, 4-(1-methylpropoxy)-butyl, 4-(2-methylpropoxy)-butyl, 4-(1,1-dimethylethoxy)-butyl and the like.

The term "fluoroalkoxy-alkyl" as used herein denotes in each case alkyl as defined above, usually comprising 1 to 6 carbon atoms, preferably 1 to 4 carbon atoms, wherein 1 carbon atom carries an fluoroalkoxy radical as defined above, usually comprising 1 to 10, frequently 1 to 6, in particular 1 to 4, carbon atoms as defined above. Examples are fluoromethoxymethyl, difluoromethoxymethyl, trifluoromethoxymethyl, 1-fluoroethoxymethyl, 2-fluoroethoxymethyl, 1,1-difluoroethoxymethyl, 1,2-difluoroethoxymethyl, 2,2-difluoroethoxymethyl, 1,1,2-trifluoroethoxymethyl, 1,2,2-trifluoroethoxymethyl, 2,2,2-trifluoroethoxymethyl, pentafluoroethoxymethyl, 1-fluoroethoxy-1-ethyl, 2-fluoroethoxy-1-ethyl, 1,1-difluoroethoxy-1-ethyl, 1,2-difluoroethoxy-1-ethyl, 2,2-difluoroethoxy-1-ethyl, 1,1,2-trifluoroethoxy-1-ethyl, 1,2,2-trifluoroethoxy-1-ethyl, 2,2,2-trifluoroethoxy-1-ethyl, pentafluoroethoxy-1-ethyl, 1-fluoroethoxy-2-ethyl, 2-fluoroethoxy-2-ethyl, 1,1-difluoroethoxy-2-ethyl, 1,2-difluoroethoxy-2-ethyl, 2,2-difluoroethoxy-2-ethyl, 1,1,2-trifluoroethoxy-2-ethyl, 1,2,2-trifluoroethoxy-2-ethyl, 2,2,2-trifluoroethoxy-2-ethyl, pentafluoroethoxy-2-ethyl, and the like.

The term "alkylthio" (also alkylsulfanyl or alkyl-S—)" as used herein denotes in each case a straight-chain or branched saturated alkyl group as defined above, usually comprising 1 to 10 carbon atoms, frequently comprising 1 to 6 carbon atoms, preferably 1 to 4 carbon atoms, which is attached via a sulfur atom at any position in the alkyl group. Examples are methylthio, ethylthio, n-propylthio, iso-propylthio, n-butylthio, 2-butylthio, iso-butylthio, tert-butylthio, and the like.

The term "haloalkylthio" as used herein refers to an alkylthio group as defined above wherein the hydrogen atoms are partially or fully substituted by fluorine, chlorine, bromine and/or iodine. Examples are fluoromethylthio, difluoromethylthio, trifluoromethylthio, 1-fluoroethylthio, 2-fluoroethylthio, 2,2-difluoroethylthio, 2,2,2-trifluoroethylthio, 2-chloro-2-fluoroethylthio, 2-chloro-2,2-difluoro-ethylthio, 2,2-dichloro-2-fluorethylthio, 2,2,2-trichloroethylthio, pentafluoroethylthio and the like The terms "alkylsulfinyl" and "$S(O)_n$-alkyl" (wherein n is 1) are equivalent and, as used herein, denote an alkyl group, as defined above, attached via a sulfinyl [S(O)] group. For example, the term "$C_1$-$C_6$-alkylsulfinyl" refers to a $C_1$-$C_6$-alkyl group, as defined above, attached via a sulfinyl [S(O)] group. Examples are methylsulfinyl, ethylsulfinyl, n-propylsulfinyl, 1-methylethylsulfinyl (isopropylsulfinyl), butylsulfinyl, 1-methylpropylsulfinyl (sec-butylsulfinyl), 2-methylpropylsulfinyl (isobutylsulfinyl), 1,1-dimethylethylsulfinyl (tert-butylsulfinyl), pentylsulfinyl, 1-methylbutylsulfinyl, 2-methylbutylsulfinyl, 3-methylbutylsulfinyl, 1,1-dimethylpropylsulfinyl, 1,2-dimethylpropylsulfinyl, 2,2-dimethylpropylsulfinyl, 1-ethylpropylsulfinyl, hexylsulfinyl, 1-methylpentylsulfinyl, 2-methylpentylsulfinyl, 3-methylpentylsulfinyl, 4-methylpentylsulfinyl, 1,1-dimethylbutylsulfinyl, 1,2-dimethylbutylsulfinyl, 1,3-dimethylbutylsulfinyl, 2,2-dimethylbutylsulfinyl, 2,3-dimethylbutylsulfinyl, 3,3-dimethylbutylsulfinyl, 1-ethylbutylsulfinyl, 2-ethylbutylsulfinyl, 1,1,2-trimethylpropylsulfinyl, 1,2,2-trimethylpropylsulfinyl, 1-ethyl-1-methylpropylsulfinyl and 1-ethyl-2-methylpropylsulfinyl.

The terms "alkylsulfonyl" and "$S(O)_n$-alkyl" (wherein n is 2) are equivalent and, as used herein, denote an alkyl group, as defined above, attached via a sulfonyl $[S(O)_2]$ group. For example, the term "$C_1$-$C_6$-alkylsulfonyl" refers to a $C_1$-$C_6$-alkyl group, as defined above, attached via a sulfonyl $[S(O)_2]$ group. Examples are methylsulfonyl, ethylsulfonyl, n-propylsulfonyl, 1-methylethylsulfonyl (isopropylsulfonyl), butylsulfonyl, 1-methylpropylsulfonyl (sec-butylsulfonyl), 2-methylpropylsulfonyl (isobutylsulfonyl), 1,1-dimethylethylsulfonyl (tert-butylsulfonyl), pentylsulfonyl, 1-methylbutylsulfonyl, 2-methylbutylsulfonyl, 3-methylbutylsulfonyl, 1,1-dimethylpropylsulfonyl, 1,2-dimethylpropylsulfonyl, 2,2-dimethylpropylsulfonyl, 1-ethylpropylsulfonyl, hexylsulfonyl, 1-methylpentylsulfonyl, 2-methylpentylsulfonyl, 3-methylpentylsulfonyl, 4-methylpentylsulfonyl, 1,1-dimethylbutylsulfonyl, 1,2-dimethylbutylsulfonyl, 1,3-dimethylbutylsulfonyl, 2,2-dimethylbutylsulfonyl, 2,3-dimethylbutylsulfonyl, 3,3-dimethylbutylsulfonyl, 1-ethylbutylsulfonyl, 2-ethylbutylsulfonyl, 1,1,2-trimethylpropylsulfonyl, 1,2,2-trimethylpropylsulfonyl, 1-ethyl-1-methylpropyl-sulfonyl and 1-ethyl-2-methylpropylsulfonyl.

The term "alkylamino" as used herein denotes in each case a group —NHR, wherein R is a straight-chain or branched alkyl group usually having from 1 to 6 carbon atoms, preferably 1 to 4 carbon atoms. Examples of an alkylamino group are methylamino, ethylamino, n-propylamino, isopropylamino, n-butylamino, 2-butylamino, isobutylamino, tert-butylamino, and the like.

The term "dialkylamino" as used herein denotes in each case a group —NRR', wherein R and R', independently of each other, are a straight-chain or branched alkyl group each usually having from 1 to 6 carbon atoms, preferably 1 to 4 carbon atoms. Examples of a dialkylamino group are dimethylamino, diethylamino, dipropylamino, dibutylamino, methyl-ethyl-amino, methyl-propyl-amino, methyl-isopropylamino, methyl-butyl-amino, methyl-isobutyl-amino, ethyl-propyl-amino, ethyl-isopropylamino, ethyl-butyl-amino, ethyl-isobutyl-amino, and the like.

The suffix "-carbonyl" in a group denotes in each case that the group is bound to the remainder of the molecule via a carbonyl C=O group. This is the case e.g. in alkylcarbonyl, haloalkylcarbonyl, alkoxycarbonyl and haloalkoxycarbonyl.

The term "aryl" as used herein refers to a mono-, bi- or tricyclic aromatic hydrocarbon radical having 6 to 14 carbon atoms. Examples thereof comprise phenyl, naphthyl, fluorenyl, azulenyl, anthracenyl and phenanthrenyl. Aryl is preferably phenyl or naphthyl and especially phenyl.

The term "3-, 4-, 5-, 6-, 7- or 8-membered saturated carbocyclic ring" as used herein refers to carbocyclic rings, which are monocyclic and fully saturated. Examples of such rings include cyclopropane, cyclobutane, cyclopentane, cyclohexane, cycloheptane, cyclooctane and the like.

The terms "3-, 4-, 5-, 6-, 7- or 8-membered partially unsaturated carbocyclic ring" and "5- or 6-membered partially unsaturated carbocyclic ring" refer to carbocyclic rings, which are monocyclic and have one or more degrees of unsaturation. Examples of such rings include include cyclopropene, cyclobutene, cyclopentene, cyclohexene, cycloheptene, cyclooctene and the like.

The term "3-, 4-, 5-, 6- or 7-membered saturated, partially unsaturated or completely unsaturated heterocyclic ring containing 1, 2 or 3 heteroatoms or heteroatom groups selected from N, O, S, NO, SO and $SO_2$, as ring members" [wherein "completely/fully unsaturated" includes also "aromatic"] as used herein denotes monocyclic radicals, the monocyclic radicals being saturated, partially unsaturated or fully unsaturated (including aromatic). The heterocyclic ring may be attached to the remainder of the molecule via a carbon ring member or via a nitrogen ring member.

Examples of a 3-, 4-, 5-, 6- or 7-membered saturated heterocyclic ring include: oxiranyl, aziridinyl, azetidinyl, tetrahydrofuran-2-yl, tetrahydrofuran-3-yl, tetrahydrothien-2-yl, tetrahydrothien-3-yl, pyrrolidin-2-yl, pyrrolidin-3-yl, pyrazolidin-3-yl, pyrazolidin-4-yl, pyrazolidin-5-yl, imidazolidin-2-yl, imidazolidin-4-yl, oxazolidin-2-yl, oxazolidin-4-yl, oxazolidin-5-yl, isoxazolidin-3-yl, isoxazolidin-4-yl, isoxazolidin-5-yl, thiazolidin-2-yl, thiazolidin-4-yl, thiazolidin-5-yl, isothiazolidin-3-yl, isothiazolidin-4-yl, isothiazolidin-5-yl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2-tetrahydropyranyl, 4-tetrahydropyranyl, 1,3-dioxan-5-yl, 1,4-dioxan-2-yl, piperidin-2-yl, piperidin-3-yl, piperidin-4-yl, hexahydropyridazin-3-yl, hexahydropyridazin-4-yl, hexahydropyrimidin-2-yl, hexahydropyrimidin-4-yl, hexahydropyrimidin-5-yl, piperazin-2-yl, 1,3,5-hexahydrotriazin-2-yl and 1,2,4-hexahydrotriazin-3-yl, morpholin-2-yl, morpholin-3-yl, thiomorpholin-2-yl, thiomorpholin-3-yl, 1-oxothiomorpholin-2-yl, 1-oxothiomorpholin-3-yl, 1,1-dioxothiomorpholin-2-yl, 1,1-dioxothiomorpholin-3-yl, azepan-1-, -2-, -3- or -4-yl, oxepan-2-, -3-, -4- or -5-yl, hexahydro-1,3-diazepinyl, hexahydro-1,4-diazepinyl, hexahydro-1,3-oxazepinyl, hexahydro-1,4-oxazepinyl, hexahydro-1,3-dioxepinyl, hexahydro-1,4-dioxepinyl and the like. Examples of a 3-, 4-, 5-, 6- or 7-membered partially unsaturated heterocyclic ring include: 2,3-dihydrofur-2-yl, 2,3-dihydrofur-3-yl, 2,4-dihydrofur-2-yl, 2,4-dihydrofur-3-yl, 2,3-dihydrothien-2-yl, 2,3-dihydrothien-3-yl, 2,4-dihydrothien-2-yl, 2,4-dihydrothien-3-yl, 2-pyrrolin-2-yl, 2-pyrrolin-3-yl, 3-pyrrolin-2-yl, 3-pyrrolin-3-yl, 2-isoxazolin-3-yl, 3-isoxazolin-3-yl, 4-isoxazolin-3-yl, 2-isoxazolin-4-yl, 3-isoxazolin-4-yl, 4-isoxazolin-4-yl, 2-isoxazolin-5-yl, 3-isoxazolin-5-yl, 4-isoxazolin-5-yl, 2-isothiazolin-3-yl, 3-isothiazolin-3-yl, 4-isothiazolin-3-yl, 2-isothiazolin-4-yl, 3-isothiazolin-4-yl, 4-isothiazolin-4-yl, 2-isothiazolin-5-yl, 3-isothiazolin-5-yl, 4-isothiazolin-5-yl, 2,3-dihydropyrazol-1-yl, 2,3-dihydropyrazol-2-yl, 2,3-dihydropyrazol-3-yl, 2,3-dihydropyrazol-4-yl, 2,3-dihydropyrazol-5-yl, 3,4-dihydropyrazol-1-yl, 3,4-dihydropyrazol-3-yl, 3,4-dihydropyrazol-4-yl, 3,4-dihydropyrazol-5-yl, 4,5-dihydropyrazol-1-yl, 4,5-dihydropyrazol-3-yl, 4,5-dihydropyrazol-4-yl, 4,5-dihydropyrazol-5-yl, 2,3-dihydrooxazol-2-yl, 2,3-dihydrooxazol-3-yl, 2,3-dihydrooxazol-4-yl, 2,3-dihydrooxazol-5-yl, 3,4-dihydrooxazol-2-yl, 3,4-dihydrooxazol-3-yl, 3,4-dihydrooxazol-4-yl, 3,4-dihydrooxazol-5-yl, 3,4-dihydrooxazol-2-yl, 3,4-dihydrooxazol-3-yl, 3,4-dihydrooxazol-4-yl, 2-, 3-, 4-, 5- or 6-di- or tetrahydropyridinyl, 3-di- or tetrahydropyridazinyl, 4-di- or tetrahydropyridazinyl, 2-di- or tetrahydropyrimidinyl, 4-di- or tetrahydropyrimidinyl, 5-di- or tetrahydropyrimidinyl, di- or tetrahydropyrazinyl, 1,3,5-di- or tetrahydrotriazin-2-yl, 1,2,4-di- or tetrahydrotriazin-3-yl, 2,3,4,5-tetrahydro[1H]azepin-1-, -2-, -3-, -4-, -5-, -6- or -7-yl, 3,4,5,6-tetrahydro[2H]azepin-2-, -3-, -4-, -5-, -6- or -7-yl, 2,3,4,7-tetrahydro[1H]azepin-1-, -2-, -3-, -4-, -5-, -6- or -7-yl, 2,3,6,7-tetrahydro[1H]azepin-1-, -2-, -3-, -4-, -5-, -6- or -7-yl, tetrahydrooxepinyl, such as 2,3,4,5-tetrahydro[1H]oxepin-2-, -3-, -4-, -5-, -6- or -7-yl, 2,3,4,7-tetrahydro[1H]oxepin-2-, -3-, -4-, -5-, -6- or -7-yl, 2,3,6,7-tetrahydro[1H]oxepin-2-, -3-, -4-, -5-, -6- or -7-yl, tetrahydro-1,3-diazepinyl, tetrahydro-1,4-diazepinyl, tetrahydro-1,3-oxazepinyl, tetrahydro-1,4-oxazepinyl, tetrahydro-1,3-dioxepinyl and tetrahydro-1,4-dioxepinyl.

A 3-, 4-, 5-, 6- or 7-membered completely unsaturated (including aromatic) heterocyclic ring is e.g. a 5- or 6-membered fully unsaturated (including aromatic) heterocyclic ring. Examples are: 2-furyl, 3-furyl, 2-thienyl, 3-thienyl, 2-pyrrolyl, 3-pyrrolyl, 3-pyrazolyl, 4-pyrazolyl, 5-pyrazolyl, 2-oxazolyl, 4-oxazolyl, 5-oxazolyl, 4-isoxazolyl, 2-thiazolyl, 4-thiazolyl, 5-thiazolyl, 4-isothiazolyl, 2-imidazolyl, 4-imidazolyl, 1,3,4-triazol-2-yl, 2-pyridinyl, 3-pyridinyl, 4-pyridinyl, 3-pyridazinyl, 4-pyridazinyl, 2-pyrimidinyl, 4-pyrimidinyl, 5-pyrimidinyl and 2-pyrazinyl.

The term "a 3-, 4-, 5-, 6-, 7- or 8-membered saturated or partially unsaturated carbocyclic or heterocyclic ring containing 1, 2 or 3 heteroatoms or heteroatom groups selected from N, O, S, NO, SO and $SO_2$, as ring members" as used herein denotes a saturated or unsaturated 3- to 8-membered ring system which optionally contains 1 to 3 heteroatoms selected from N, O, S, NO, SO and $SO_2$, as defined above, with the exception of the completely unsaturated ring systems.

The remarks made below concerning preferred embodiments of the variables of the compounds of the formulae (I), (I-A), (I-B), (II), (VI) and (VII) are valid on their own as well as preferably in combination with each other concerning the compounds of formula (I), (I-A) and (I-B) as well as concerning the methods according to the invention.

In the compounds of the formulae (I), (I-A), (I-B), (II) and (VI), $R^1$ is preferably an electron-withdrawing group and is preferably selected from halogen, $C_1$-$C_4$-alkyl, fluoroalkyl, $CBrF_2$, $C_5$-$C_6$-cycloalkyl, $C_5$-$C_6$-fluorocycloalkyl, $C_2$-$C_4$-alkenyl, $C_2$-$C_4$-fluoroalkenyl, wherein the six last mentioned radicals may be substituted by 1, 2 or 3 radicals $R^a$; —N($R^{c1}$)$R^{d1}$, phenyl which may be substituted by 1, 2 or 3 radicals $R^e$, and a 5- or 6-membered saturated, partially unsaturated or aromatic heterocyclic ring containing 1 or 2 heteroatoms or heteroatom groups selected from N, O and S as ring members, where the heterocyclic ring may be substituted by 1, 2 or 3 radicals $R^e$. In a specific embodiment, $R^1$ is as defined herein and in the claims, with the proviso, that it is not $CBrF_2$.

More preferably $R^1$ is selected from halogen, $C_1$-$C_4$-fluoroalkyl, $C_1$-$C_4$-alkoxy and $C_1$-$C_4$-fluoroalkoxy-$C_1$-$C_4$-alkyl, particularly selected from halogen, $CF_3$, $CHF_2$ and methoxy, and specifically from $CF_3$ and $CHF_2$.

In the compounds of the formulae (I), (I-A), (I-B), (II) and (VI), each $R^2$ preferably is independently selected from halogen, $C_1$-$C_4$-alkyl, $C_1$-$C_4$-fluoroalkyl, $C_5$-$C_6$-cycloalkyl, $C_5$-$C_6$-fluorocycloalkyl, $C_2$-$C_4$-alkenyl, $C_2$-$C_4$-fluoroalkenyl, wherein the six last mentioned radicals may be substituted by one or more radicals $R^a$; —$OR^b$, —$SR^b$, —N($R^{c1}$)$R^{d1}$, phenyl which may be substituted by 1, 2 or 3 radicals $R^e$, and a 5- or 6-membered saturated, partially unsaturated or completely unsaturated heterocyclic ring containing 1 or 2 heteroatoms or heteroatom groups selected from N, O and S, as ring members, where the heterocyclic ring may be substituted by 1, 2 or 3 radicals $R^e$.

More preferably each $R^2$ is independently selected from halogen and halomethyl, in particular from halogen and $CF_3$ and specifically $R^2$ is chlorine.

In the compounds of the formulae (I), (I-A), (I-B), (II) and (VI), r is preferably 1, 2 or 3 and especially preferably 1. When r is 1, $R^2$ is preferably located in position 3 of the pyridyl moiety of the compound of the formulae I, I-A, I-B, II or VI, i.e. is bound to the ring carbon atom of the pyridyl moiety that is ortho to the pyrazole bond.

In the compounds of the formula (I-A), $M^+$ is a cation or cation equivalent compensating the charge of the anionic carboxylate. Due to the base used, $M^+$ will generally comprise a magnesium cation. However, if the reaction is performed in the presence of a salt or salt-like additive comprising another cation, $M^+$ may be at least partly or completely replaced by a different, such as an alkali metal cation or an earth alkali metal cation, which is different from a magnesium cation. Preferably, $M^+$ is a metal cation, in particular an alkali or earth alkali metal cation, in particular, $Li^+$, $Na^+$, $Ka^+$, $(Mg^{2+})/2$, $(Ca^{2+})/2$. Due to the reagents employed, Mg cations are present in the reaction mixture. Preferably, $M^+$ is a cation or cation equivalent compensating the charge of the carboxylate and comprising Mg, i.e. a magnesium cation. Preferably, $M^+$ comprises a magnesium cation, in particular a magnesium cation, selected from $(Mg^{2+})/2$, $(MgBr^+)$ or $(MgCl^+)$. Especially $M^+$ is $(Mg^{2+})/2$, $(MgBr^+)$ or $(MgCl^+)$. In a specific embodiment, $M^+$ is $(Mg^{2+})/2$.

Acid compounds of formula (I-B) are known, e.g. from WO 02/070483 or WO03/015519, where they are obtained after reaction with lithium organic bases, eg. LDA. The corresponding carboxylate compounds of formula (I-A) have not yet been isolated or described. In the crude work-up mixture, one may assume that the carboxylate may be present. However, the carboxylate is then present in the form of its lithium salt, due to the nature of the reagents employed.

Therefore, a further aspect of the present invention relates to a compound of formula I-A:

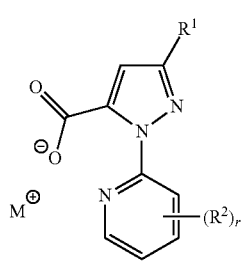

in which the variables $R^1$, $R^2$ and r are each as defined herein and in the claims, and in which $M^+$ is a cation or cation equivalent compensating the charge of the carboxylate and comprising magnesium in particular a magnesium cation, selected from $(Mg^{2+})/2$, $(MgBr^+)$ or $(MgCl^+)$. Especially $M^+$ in formula I-A is $(Mg^{2+})/2$, $(MgBr^+)$ or $(MgCl^+)$.

In the compounds of the formulae (VI) and (VII), $R^3$ and $R^4$ are preferably, independently of each other, selected from halogen, cyano, nitro, $C_1$-$C_4$-alkyl, $C_5$-$C_6$-cycloalkyl, $C_5$-$C_8$-halocycloalkyl, $C_2$-$C_4$-alkenyl, $C_2$-$C_4$-haloalkenyl, wherein the six last mentioned radicals may be substituted by one or more radicals $R^a$; —$OR^{b1}$, —$OS(O)_nR^{b1}$, $SR^{b1}$, —$N(R^{c1})R^{d1}$, —$C(=O)R^a$, phenyl which may be substituted by 1, 2 or 3 radicals $R^e$, and a 5- or 6-membered saturated, partially unsaturated or completely unsaturated heterocyclic ring containing 1 or 2 heteroatoms selected from N, O and S, as ring members, where the heterocyclic ring may be substituted by 1, 2 or 3 radicals $R^e$.

More preferably $R^3$ and $R^4$ are independently selected from halogen, cyano, $C_1$-$C_4$-alkyl, $C_1$-$C_4$-haloalkyl. Particularly preferred $R^3$ is selected from halogen, methyl and halomethyl, specifically from chlorine, bromine, methyl, $CF_3$ and $CHF_2$, and $R^4$ is selected from halogen, cyano, methyl and halomethyl, specifically from chlorine, bromine, cyano, $CF_3$ and $CHF_2$.

In the compounds of the formulae (VI) and (VII), $R^5$ is preferably selected from hydrogen, $C_1$-$C_6$-alkyl, $C_1$-$C_6$-haloalkyl, $C_5$-$C_6$-cycloalkyl, $C_5$-$C_6$-halocycloalkyl, wherein the four last radicals may optionally be substituted by one or more radicals $R^a$; —$C(=O)R^a$; phenyl which may be substituted by 1, 2 or 3 radicals $R^e$; and a 5- or 6-membered saturated, partially unsaturated or completely unsaturated heterocyclic ring containing 1 or 2 heteroatoms selected from N, O and S, as ring members, where the heterocyclic ring may be substituted by 1, 2 or 3 radicals $R^e$.

More preferably each $R^5$ is selected from hydrogen, $C_1$-$C_4$-alkyl, $C_1$-$C_4$-haloalkyl and —$C(=O)$—$C_1$-$C_4$-alkyl, in particular from hydrogen, $C_1$-$C_3$-alkyl and halomethyl, and specifically $R^5$ is hydrogen.

In the compounds of the formulae (VI) and (VII), t is preferably 0. In the compounds of the formulae (VI) and (VII), wherein t is 0, $R^6$ and $R^7$ are preferably, independently of each other, selected from hydrogen, $C_1$-$C_6$-alkyl, $C_1$-$C_6$-haloalkyl, $C_3$-$C_6$-cycloalkyl, $C_3$-$C_6$-halocycloalkyl, $C_2$-$C_4$-alkenyl, $C_2$-$C_4$-haloalkenyl, wherein the six last radicals may optionally be substituted by one or more radicals $R^a$; or $R^6$ and $R^7$ together represent a $C_4$-$C_5$-alkylene or $C_4$-$C_5$-alkenylene chain forming together with the sulfur atom to which they are attached a 5- or 6-membered saturated or partially unsaturated ring, wherein one of the $CH_2$ groups in the $C_4$-$C_5$-alkylene chain or one of the $CH_2$ or CH groups in the $C_4$-$C_5$-alkenylene chain may be replaced by a group independently selected from O, S and N and NH, and wherein the carbon and/or nitrogen atoms in the $C_4$-$C_5$-alkylene or $C_4$-$C_5$-alkenylene chain may be substituted with 1 or 2 substituents independently selected from halogen, cyano, $C_1$-$C_4$-alkyl, $C_1$-$C_4$-haloalkyl, $C_1$-$C_4$-alkoxy, $C_1$-$C_4$-haloalkoxy.

More preferably $R^6$ and $R^7$ are independently selected from $C_1$-$C_6$-alkyl, $C_1$-$C_6$-haloalkyl, or $R^6$ and $R^7$ together represent a $C_4$-$C_5$-alkylene chain forming together with the sulfur atom to which they are attached a 5- or 6-membered ring. Particularly preferred $R^6$ and $R^7$ are each $C_1$-$C_6$-alkyl, or together represent a $C_4$-$C_5$-alkylene chain forming together with the sulfur atom to which they are attached a 5- or 6-membered ring. More preferably $R^6$ and $R^7$ are independently selected from $C_1$-$C_4$-alkyl, $C_1$-$C_4$-haloalkyl, or $R^6$ and $R^7$ together represent a $C_4$-$C_5$-alkylene chain forming together with the sulfur atom to which they are attached a 5- or 6-membered ring. Particularly preferred $R^6$ and $R^7$ are each $C_1$-$C_4$-alkyl, or together represent a $C_4$-$C_5$-alkylene chain forming together with the sulfur atom to which they are attached a 5- or 6-membered ring. Particularly preferred, when t is 0, $R^6$ and $R^7$ are selected independently of one another from $C_1$-$C_6$-alkyl, or $R^6$ and $R^7$ together represent a $C_3$-$C_6$-alkylene chain forming together with the sulfur atom to which they are attached a 4-, 5-, 6- or 7-membered saturated ring. Specifically $R^6$ and $R^7$ are each methyl, isopropyl or ethyl, or together represent a butylene chain forming together with the sulfur atom to which they are attached a 5-membered ring.

In the compounds of the formulae (VI) and (VII), wherein t is 1, the preferred meanings of $R^6$ and $R^7$ are the preferred meanings as described above in the compounds of the formulae (VI) and (VII), wherein t is 0.

In this context, the variables $R^a$, $R^b$, $R^c$, $R^d$, $R^{b1}$, $R^{c1}$, $R^{d1}$, $R^e$, $R^f$, $R^g$, $R^h$, $R^i$, m and n, independently of each other, preferably have one of the following meanings:

$R^a$ is selected from $C_1$-$C_4$-alkyl, $C_1$-$C_4$-fluoroalkyl, $C_3$-$C_6$-cycloalkyl, $C_3$-$C_6$-fluorocycloalkyl, $C_2$-$C_4$-alkenyl, $C_2$-$C_4$-fluoroalkenyl, $C_1$-$C_4$-alkoxy, $C_1$-$C_4$-alkylthio, amino, di-($C_1$-$C_4$-alkyl)-amino, phenyl and a 5- or 6-membered saturated, partially unsaturated or completely unsaturated heterocyclic ring containing 1 or 2 heteroatoms selected from N, O and S, as ring members, where phenyl and the heterocyclic ring may be substituted by 1, 2 or 3 radicals selected from $C_1$-$C_4$-alkyl, $C_1$-$C_4$-fluoroalkyl, $C_5$-$C_6$-cycloalkyl and $C_5$-$C_6$-fluorocycloalkyl.

More preferably $R^a$ is selected from $C_1$-$C_4$-alkyl and $C_1$-$C_4$-fluoroalkyl, $C_1$-$C_4$-alkoxy, di-($C_1$-$C_4$-alkyl)-amino, phenyl and a 5- or 6-membered saturated, partially unsaturated or completely unsaturated heterocyclic ring containing 1 or 2 heteroatoms selected from N, O and S, as ring members, and in particular selected from $C_1$-$C_3$-alkyl and $C_1$-$C_2$-fluoroalkyl and $C_1$-$C_2$-alkoxy.

$R^b$ is selected from $C_1$-$C_4$-alkyl, $C_1$-$C_4$-fluoroalkyl, $C_5$-$C_6$-cycloalkyl, $C_5$-$C_6$-fluorocycloalkyl, $C_1$-$C_4$-alkoxy-$C_1$-$C_4$-alkyl, $C_1$-$C_4$-fluoroalkoxy-$C_1$-$C_4$-alkyl, phenyl-$C_1$-$C_4$-alkyl, phenoxy-$C_1$-$C_4$-alkyl and pyridyl-$C_1$-$C_4$-alkyl, wherein phenyl and pyridyl in the three last mentioned radicals may optionally carry 1 or 2 radicals selected from halogen, substituents $C_1$-$C_4$-alkyl, $C_1$-$C_2$-fluoroalkyl, $C_1$-$C_4$-alkoxy and $C_1$-$C_2$-fluoroalkoxy.

More preferably $R^b$ is selected from $C_1$-$C_4$-alkyl, $C_1$-$C_4$-fluoroalkyl and benzyl, and in particular selected from $C_1$-$C_3$-alkyl, $C_1$-$C_2$-fluoroalkyl and benzyl.

$R^c$, $R^d$ are, independently from one another and independently of each occurrence, selected from $C_1$-$C_4$-alkyl, $C_1$-$C_4$-fluoroalkyl, $C_5$-$C_6$-cycloalkyl, $C_5$-$C_6$-fluorocycloalkyl, wherein the four last mentioned radicals may optionally carry 1 or 2 radicals selected from $C_1$-$C_4$-alkoxy, $C_1$-$C_4$-fluoroalkoxy, $C_1$-$C_4$-alkylthio, $C_1$-$C_4$-fluoroalkylthio, phenyl, benzyl, pyridyl and phenoxy, wherein the four last mentioned radicals may carry 1 or 2 substituents selected from halogen, $C_1$-$C_4$-alkyl, $C_1$-$C_2$-fluoroalkyl, $C_1$-$C_4$-alkoxy and $C_1$-$C_2$-fluoroalkoxy; or $R^c$ and $R^d$, together with the nitrogen atom to which they are bound, form a 5- or 6-membered saturated, partly unsaturated or completely unsaturated heterocyclic ring which may contain 1 further heteroatom selected from N, O and S as ring members, where the heterocyclic ring may carry 1 or 2 substituents selected from halogen, $C_1$-$C_4$-alkyl and $C_1$-$C_4$-fluoroalkyl.

More preferably $R^c$, $R^d$ are, independently from one another and independently of each occurrence, selected from $C_1$-$C_4$-alkyl, $C_1$-$C_4$-fluoroalkyl and benzyl, or $R^c$ and $R^d$, together with the nitrogen atom to which they are bound, form a 5- or 6-membered saturated or partly unsaturated heterocyclic ring. In particular, $R^c$, $R^d$ are, independently from one another and independently of each occurrence, $C_1$-$C_3$-alkyl, $C_1$-$C_2$-fluoroalkyl, benzyl, or together with the nitrogen atom to which they are bound form a pyrrolidine or a piperidine ring.

$R^{b1}$ is hydrogen or has one of the preferred meanings given for $R^c$.

$R^{c1}$ is hydrogen or has one of the preferred meanings given for $R^c$.

$R^{d1}$ is hydrogen or has one of the preferred meanings given for $R^d$.

$R^e$ is selected from halogen, $C_1$-$C_4$-alkyl, $C_1$-$C_4$-fluoroalkyl, $C_2$-$C_4$-alkenyl, $C_2$-$C_4$-fluoroalkenyl, where the four last mentioned radicals may optionally carry 1 or 2 radicals selected from $C_1$-$C_2$-alkoxy; $C_1$-$C_4$-alkoxy, $C_1$-$C_4$-fluoroalkoxy, phenyl, benzyl, pyridyl and phenoxy, wherein the four last mentioned radicals may carry 1 or 2 substituents selected from halogen, $C_1$-$C_2$-alkyl and $C_1$-$C_2$-fluoroalkyl.

More preferably $R^e$ is selected from $C_1$-$C_4$-alkyl, $C_1$-$C_4$-fluoroalkyl, $C_1$-$C_4$-alkoxy and $C_1$-$C_4$-fluoroalkoxy, and in particular from $C_1$-$C_3$-alkyl, $C_1$-$C_2$-fluoroalkyl, $C_1$-$C_2$-alkoxy, $C_1$-$C_2$-fluoroalkoxy.

$R^f$, $R^g$ are, independently of each other and independently of each occurrence, selected from $C_1$-$C_4$-alkyl, $C_5$-$C_6$-cycloalkyl, $C_1$-$C_2$-alkoxy-$C_1$-$C_2$-alkyl, phenyl and benzyl.

More preferably $R^f$, $R^g$ are, independently of each other and independently of each occurrence, selected from $C_1$-$C_4$-alkyl, $C_5$-$C_6$-cycloalkyl, benzyl and phenyl, and in particular from $C_1$-$C_3$-alkyl, benzyl and phenyl.

$R^h$, $R^i$ are, independently from one another and independently of each occurrence, selected from hydrogen, halogen, $C_1$-$C_4$-alkyl, $C_1$-$C_4$-fluoroalkyl, $C_5$-$C_6$-cycloalkyl, $C_5$-$C_6$-fluorocycloalkyl, where the four last mentioned radicals may optionally carry 1 or 2 radicals selected from $C_1$-$C_3$-alkyl and $C_1$-$C_3$-fluoroalkyl; $C_1$-$C_4$-alkoxy, $C_1$-$C_4$-fluoroalkoxy, phenyl, pyridyl and phenoxy.

More preferably $R^h$, $R^i$ are, independently of each other and independently of each occurrence, selected from hydrogen, $C_1$-$C_3$-alkyl and $C_1$-$C_2$-fluoroalkyl.

m is 1 or 2, wherein, in the case of several occurrences, m may be identical or different. More preferably m is 2.

n is 1 or 2, wherein, in the case of several occurrences, n may be identical or different. More preferably n is 2.

The conversion in step (i) of the process according to the first aspect of the invention for preparing an N-substituted 1H-pyrazole-5-carboxylate compound I-A is a deprotonation of the carbon atom in position 5 of the pyrazole ring of compound II, i.e. an abstraction of a proton in said position. This transformation is effected by contacting the starting compounds including a compound II and a base, preferably in a solvent and under an inert atmosphere, using suitable reaction conditions.

For the deprotonation reaction in step (i) of the process according to the present invention any base selected from magnesium-organic compounds, and in particular selected from magnesium-organic base having a carbon bound magnesium, such as alkyl and cycloalkyl magnesium halides, e.g. isopropyl magnesium chloride or isopropyl magnesium bromide can be used. For the deprotonation reaction in step (i) of the process according to the present invention, it is also possible to use aryl magnesium halides, in particular phenyl magnesium halides such as phenyl magnesium bromide and phenyl magnesium chloride.

According to a preferred embodiment of the invention the base in step (i) in the process of the invention is selected from $C_1$-$C_6$-alkyl magnesium halides and $C_5$-$C_6$-cycloalkyl magnesium halides, more preferably selected from $C_1$-$C_4$-alkyl magnesium chlorides, $C_1$-$C_4$-alkyl magnesium bromides, $C_5$-$C_6$-cycloalkyl magnesium chlorides and $C_5$-$C_6$-cycloalkyl magnesium bromides, and in particular selected from methyl magnesium chloride, ethyl magnesium chloride, n-propyl magnesium chloride, isopropyl magnesium chloride, methyl magnesium bromide, ethyl magnesium bromide, n-propyl magnesium bromide, isopropyl magnesium bromide.

The base employed in step (i) is generally used in an amount of 0.8 to 3.5 mol, more preferably of 1.0 to 3.0 mol, in particular of 1.01 to 2.5 mol and especially of 1.1 to 2.2 mol, based in each case on 1 mol of the compound of the formula (II).

According to a particular embodiment of the invention in step (i) of the inventive process a magnesium-organic base is used in an amount of typically 1.0 to 3.5 mol, more preferably of 1.3 to 3.0 mol, in particular of 1.5 to 2.5 mol and especially of 1.7 to 2.2 mol, based in each case on 1 mol of the compound of the formula (II). It is also possible to use lower amounts of the magnesium organic base, e.g. from 0.8 to 1.7 mol, in particular from 1 to 1.5 mol, based in each case on 1 mol of the compound of the formula (II).

In addition to the magnesium-organic compound a salt or salt-like additive may be used, in particular a metal salt selected from Fe(II) salts, Fe(III) salts, Cu(I) salts, Cu(II) salts, Ni(II) salts, Co(II) salts, Co(III) salts, Zn(II) salts, Li salts and Mg salts. Suitable metal salts are e.g. the halides, sulfates, carbonates and alkoxides such as methoxides or ethoxides, in particular the halides, especially the chlorides and bromides of the aforementioned metals. Particularly preferred additives are lithium salts, in particular lithium halides such as lithium chloride or lithium bromide but also, lithium sulphate, lithium carbonate and lithium alkoxides such as lithium methoxide or lithium ethoxide. In this embodiment, the amount of metal salt will generally be from 0.1 to 3 mol, in particular from 0.5 to 2 mol, calculated as metal, per mol of magnesium in the base.

The deprotonation of step (i) is usually performed in an aprotic organic solvent or a mixture of aprotic organic solvents. Suitable aprotic organic solvents here include, for example, aprotic solvent having an ether moiety, e.g. aliphatic and cycloaliphatic $C_3$-$C_8$ ethers, in particular aliphatic $C_3$-$C_6$ ethers such as dimethoxyethane, diethylene glycol dimethyl ether, diethyl ether, dipropyl ether, diisopropyl ether, di-n-butyl ether, methyl isobutyl ether, methyl cyclopentyl ether, tert-butyl methyl ether and tert-butyl ethyl ether, alicyclic $C_3$-$C_6$ ethers, such as tetrahydrofuran (THF), tetrahydropyran, 2-methyltetrahydrofuran, 3-methyltetrahydrofuran and dioxane, aliphatic hydrocarbons, such as pentane, hexane, heptane and octane, and also petroleum ether, cycloaliphatic hydrocarbons, such as cyclopentane and cyclohexane, aromatic hydrocarbons, such as benzene, toluene, the xylenes and mesitylene, or mixtures of these solvents with one another.

The solvent for the conversion in step (i) preferably comprises at least one aprotic solvent having an ether moiety, which is in particular selected from aliphatic and alicyclic ethers, especially form $C_3$-$C_8$-aliphatic ethers and $C_4$-$C_6$ alicyclic ethers, or a mixture thereof. The solvent for the conversion in step (i) is in particular selected from aprotic solvents having an ether moiety, which is in particular selected from aliphatic and alicyclic ethers, especially form $C_3$-$C_6$-aliphatic ethers and $C_4$-$C_6$ alicyclic ethers, or a mixture thereof. Preferably, THF or dimethoxyethane or solvent mixtures comprising them are used as solvent. In a particular embodiment dimethoxyethane is used as solvent. In another particular embodiment, a mixture of tetrahydrofurane and dimethoxy ethane is used as a solvent. If compound II is initially present in the reaction vessel in a solvent, which is preferably dimethoxyethane, the base may be added in the same solvent or a different solvent, selected from THF, diethyl ether or dimethoxyethane.

The solvent may contain a aprotic amide or urea as a cosolvent, e.g. N-methyl pyrrolidone, N,N-dimethyl acetamide, N,N'-dimethyl propylene urea (DMPU), N,N,N',N'-Tetramethyl urea etc.

The total amount of the solvent used in step (i) of the process according to the invention is typically in the range from 500 to 6000 g, preferably in the range from 600 to 5000 g, in particular from 800 to 3000 g, based on 1 mol of the compound II.

Preference is given to using solvents which are essentially anhydrous, i.e. have a water content of less than 5000 ppm, in particular less than 2000 ppm, especially less than 1000 ppm. Generally, the water contained in the solvent will react with the magnesium organic compound resulting in a certain loss of base, which can be compensated by using higher amounts of the magnesium organic compound.

In general, the reaction of step (i) is performed under temperature control.

The reaction of step (i) may be performed in any type of reactor, e.g. a reaction vessel, which is operated continuously or batch-wise, or a continuously operated tube like reaction zone. The reaction vessel may be a closed or unclosed reaction vessel, optionally with stirring and/or a cooling device. The tube like reaction zone may have static or dynamic mixers. The reactor may also be a micro-reactor.

A suitable temperature profile for the reaction in step (i) is determined by several factors, for example the reactivity of the compound II used and the type of base selected, the type of additive, solvent or co-solvent, if present, and can be determined by the person skilled in the art in the individual case, for example by simple preliminary tests. Generally the deprotonation of step (i) will be performed at a temperature in the range from –30 to +50° C., in particular from –20 to +20° C., most preferably under cooling from –5 to +10° C.

The reactants and additives, if present, can in principle be contacted with one another in any desired sequence. For example, the compound II, optionally dissolved in a solvent or in dispersed form, optionally together with additive, can be initially charged and then the base, optionally in dissolved or dispersed form, is added, or, conversely, the base, optionally dissolved or dispersed in a solvent, optionally together with additive, can be initially charged and admixed with the compound II. Alternatively, the two reactants, optionally together with additive, can also be fed simultaneously to the reactor.

It has been found to be appropriate to initially charge the compound II, preferably in a solvent, and then adjust the reaction mixture to a temperature in the range of –20 to 50° C., preferably in the range of –10 to 25° C., depending on the reaction conditions of the individual case and in particular depending on the specific base to be used. Afterwards the base, optionally in a solvent, is added either stepwise, continuously or in one portion and the reaction is allowed to continue for a period of time, possibly at the same temperature, at an elevated temperature or at a gradually rising temperature, wherein the upper limit of the temperature is the upper limit of the temperature ranges described above as preferred.

For the conversion in step (i), compound II and the base are brought into contact at a set temperature typically in the range of –30 to 50° C., preferably of –20 to 30° C. and in particular of –10 to 25° C. Afterwards the conversion is usually continued either at the set temperature or by applying a temperature gradient with the set temperature as the lower limit and an upper limit in the range of –20 to 35°, preferably of –15 to 30° C. and in particular of –5 to 25° C. or ambient temperature. Ambient temperature is to be understood from 15 to 28° C., preferably from 20 to 25° C.

The reaction product obtained from the conversion in step (i) of the inventive process is usually subjected without preceding work-up to the conversion in step (ii) of the process according to the first aspect of the invention. To this end, typically the reaction mixture obtained after the completion of the conversion in step (i) is directly introduced to the conversion in step (ii).

The conversion in step (ii) of the process according to the first aspect of the invention for preparing an N-substituted 1H-pyrazole-5-carboxylate compound of the formula (I-A) is a carboxylation of the intermediate product obtained in step (i) of the process. This conversion comprises an electrophilic attack of the carbon atom present in carbon dioxide on the deprotonated carbon atom in position 5 of the pyrazole ring of the intermediate derived from compound II. Said electrophilic attack results in the covalent attachment of the carboxylate group $CO_2$— and, as a consequence, in the formation of the N-substituted 1H-pyrazole-5-carboxylate compound I-A. This reaction is effected by contacting the intermediate obtained in step (i) with carbon dioxide or a carbon dioxide equivalent, preferably in a solvent and under an inert atmosphere, using suitable reaction conditions.

Suitable carbon dioxide equivalents are compounds which react in the same manner as carbon dioxide or which have a capability to release carbon dioxide. These carbon dioxide equivalents may be used instead of carbon dioxide itself, provided they are free from water, to avoid side reactions. However, carbon dioxide is preferred as carboxylation reagent in step (ii).

The reactants can in principle be contacted with one another in any desired sequence. For example, the reaction mixture obtained from step (i) that includes the intermediate product resulting from the deprotonation in step (i), optionally mixed with additional solvent, can be initially charged and then solid or gaseous carbon dioxide, optionally in dissolved form, is added, or bubbled through the reaction mixture, or, alternatively, the atmosphere of the reaction vessel is exchanged to carbon dioxide bringing the reaction mixture into contact by suitably stirring. It is also possible to charge a solution or solid carbon dioxide into the reactor and then feed the intermediate product resulting from the deprotonation in step (i), preferably as a solution, to the reactor.

In case the reaction mixture of step (i) is admixed with additional solvent before the carboxylation in step (ii) is initiated, said additional solvent is an aprotic solvent which in particular is selected from the aprotic organic solvents mentioned herein before, especially from those mentioned as preferred. Preferably, the additional solvent is essentially anhydrous, i.e. it has a water content of less than 2000 ppm, in particular less than 1000 ppm.

Frequently, the carbon dioxide or carbon dioxide equivalent is introduced into the reaction of step (ii) in gaseous form either by bubbling through the reaction mixture or by changing the atmosphere to carbon dioxide with simultaneous vigorous stirring, or dissolved in a suitable solvent that is generally selected from the apolar aprotic organic solvents mentioned before. In other embodiments carbon dioxide is introduced into the reaction of step (ii) in solid form, i.e. by adding solid carbon dioxide to the reaction mixture, preferably with simultaneous vigorous stirring.

According to a particular embodiment of the invention, the carboxylation in step (ii) is effected by bubbling gaseous carbon dioxide through the reaction solution. Preferably, the gaseous carbon dioxide is dry, i.e. free from water. The pressure of the carbon dioxide gas is from 0.9 to 20 bar, preferred from 0.9 to 10 bar, more preferred from 0.95 to 2 bar, most preferred from 0.95 to 1.1 bar.

The progress of step (ii) of the reaction depends on the consumption of carbon dioxide, which in general is used in excess. The determination of the end of this reaction is usually done by monitoring the reaction enthalpy. Once, the exothermic reaction has ceased, the conversion to the carboxylate of formula (I-A) is complete and no more carbon dioxide needs to be introduced to the reaction mixture. The determination of the end of this reaction may also be monitored by analytical chromatography, e.g. by thin layer chromatography or by HPLC.

In general, the conversion in step (ii) is performed under temperature control.

The reaction of step (ii) may be performed in any type of reactor, e.g. a reaction vessel, which is operated continuously or batch-wise, or a continuously operated tube like reaction zone. The reaction vessel may be a closed or unclosed reaction vessel, optionally with stirring and/or a cooling device. The tube like reaction zone may have static or dynamic mixers. The reactor may also be a micro-reactor.

A suitable temperature profile for the reaction in step (ii) is determined by several factors, in particular the type of base that was used in the deprotonation of step (i), the reactivity of the intermediate obtained in step (i) and the carboxylation reagent selected, and can be determined by the person skilled in the art for each individual case by conventional measures, such as preliminary tests. Generally the reaction will be performed at temperatures ranging from −40 to +80° C., in particular from −20 to +50° C.

Frequently, the reaction mixture obtained after completion of step (i) is adjusted to a temperature in the range of −30 to +60° C., preferably in the range of −20 to +50° C., if required, and then the carboxylation reagent, optionally dissolved in a solvent or in gaseous form, is added. The reaction is allowed to continue for a period of time, possibly at the same temperature, or alternatively at an elevated or gradually rising temperature. Preferably, the temperature is controlled by the speed of the addition of the carboxylation reagent: As the reaction temperature will mostly rise during the reaction, a higher speed will increase the temperature of the reaction mixture. The speed of the carboxylation reagent addition is adjusted in a manner that the temperature of the reaction mixture is kept at the optimum where the reaction proceeds whereas side reactions are avoided.

The intermediate from step (i) and the reagent are brought into contact in step (ii) at a set temperature typically in the range of −30 to +60° C., preferably of −20 to +50° C. and in particular of −5 to +45° C. or ambient temperature. Afterwards the conversion is usually continued either at the set temperature or by applying a temperature gradient with the set temperature as the lower limit and an upper limit in the range of −10 to +60° C., preferably of −5 to +50° C. and in particular of 0 to +50° C. or ambient temperature, and then optionally allow the reaction to proceed at the upper limit temperature.

The reaction mixture obtained after the conversion in step (ii), that contains the N-substituted 1H-pyrazole-5-carboxylate compound of the formula (I-A) as product, can be employed without purification in the next step or can be subjected to a workup procedure before introducing it to a subsequent reaction step. It is also possible to change the solvent for the next reaction step, even in the case of absence of a purification step. In a particular embodiment, the solvent used in the previous step (ii) is at least partly removed, and, in preparation for the next step, the crude reaction mixture is dissolved in a different solvent, preferably an aliphatic, cycloaliphatic or aromatic hydrocarbon, which may be chlorinated, e.g. dichloromethane, dichloroethane, hexane, cyclohexane, chlorobenzene or toluene or a mixture thereof. In another particular embodiment, the solvent of the previous step (ii) is not removed but the reaction mixture, optionally after washing and/or filtration is directly employed in the subsequent step.

The N-substituted 1H-pyrazole-5-carboxylate compound of the formula (I-A) can be converted to the corresponding acid chloride (N-substituted 1H-pyrazole-5-carbonylchloride compound of the formula I) either directly (step ii-a) or via the free acid I-B (step ii-b+ii-c). The direct conversion of the carboxylate (I-A) to the acid chloride (I) according to chlorination step (ii-a) is effected by same methods as known in the art for the preparation of acid chlorides from the acids, by same methods as known in the art for the preparation of acid chlorides from the acids, by reacting the carboxylate compound (I-A) with a chlorinating agent, e.g. thionyl chloride, phosphorous pentachloride, phosphorous trichloride or oxalyl chloride, optionally in the presence of catalytic amounts of a polar carboxamide such as N,N-dimethylformamide (DMF). For example, U.S. Pat. No. 4,544,654 describes a conversion of a sodium salt of a carboxylic acid to the corresponding acid chloride, which method can be applied here by analogy. The chlorination step (ii-a) is preferably effected in a non-polar solvent, e.g. an aliphatic cycloaliphatic or aromatic hydrocarbon, which may be chlorinated, e.g. dichloromethane, dichloroethane, hexane, cyclohexane, chlorobenzene or toluene. The chlorination of step (ii-a) may also be effected in the solvent used for deprotonation/carboxylation or in a mixture of these solvents with the aforementioned non-polar solvents. The chlorination of step (ii-a) is generally effected at a temperature from −5° C. to +140° C., or from 0 to 110° C., or preferably from 0 to 25° C. The chlorination of step (ii-a) is preferably effected from 0 to 25° C. using oxalyl chloride or from 20 to 110° C. using thionyl chloride.

The conversion of the N-substituted 1H-pyrazole-5-carboxylate compound of the formula (I-A) to the corresponding free carbonic acid (I-B), step (ii-b), is effected by acidification of the reaction solution, e.g. by addition of aqueous acids, such as hydrochloric acid, sulfuric acid, phosphoric acid or the like. The resulting acid compound I-B can be isolated or employed in the next reaction step without purification. Preferably, the acid compound I-B is purified at least by a work-up in aqueous media and isolated from the organic phase after drying.

The conversion of the N-substituted 1H-pyrazole-5-carbonic acid compound of the formula (I-B) to the corresponding to the corresponding acid chloride (N-substituted 1H-pyrazole-5-carbonylchloride compound of the formula I), step (ii-c), is effected by standard methods of preparation of acid chlorides, as for example described in Organikum, Wiley-VCH, Weinheim, 21$^{st}$ ed. 2001, p. 498, e.g. by reacting I-B with a chlorinating agent, e.g. thionyl chloride or oxalyl chloride, optionally in the presence of catalytic amounts of a polar carboxamide such as DMF. The chlorination step (ii-c) is preferably effected in an non-polar solvent, e.g. an aliphatic cycloaliphatic or aromatic hydrocarbon, which may be chlorinated, e.g. dichloromethane, dichloroethane, hexane, cyclohexane, chlorobenzene or toluene and especially in toluene. The chlorination step (ii-c) is preferably effected at a temperature from −5° C. to +140° C. or from 0 to 110° C., in particular from 0 to 25° C. using oxalyl chloride or from 20 to 110° C. using thionyl chloride.

The reaction mixture obtained after the conversion in step (ii-a) or (ii-b+ii-c), that contains the N-substituted 1H-pyrazole-5-carbonylchloride compound of the formula (I) as product, may be subjected to a workup procedure before introducing it to a subsequent reaction step. However, it is also possible to use the crude reaction mixture obtained from the reaction of I-A or I-B with the chlorinating agent, optionally after filtration. The workup is typically effected by non-aqueous means known in the art to be applicable for similar reactions. Preferably, the reaction mixture, optionally after mixing it with an non-polar aprotic solvent, that usually is an aliphatic ether, an acyclic ether, an aliphatic or cycloaliphatic hydrocarbon, aromatic hydrocarbon or a mixture of the aforementioned solvents, in particular cyclohexane or toluene and specifically toluene, is worked-up by filtering off solids that may be present. The filtered solids, if present, are washed with the solvent, the combined filtrate is concentrated by evaporation and the residue is extracted with an non-polar aprotic solvent that typically is the same as used before. Undissolved solids may be again filtered off, washed with the solvent and the product is isolated from the resulting filtrate, e.g. by removing solvents via evaporation or distillation or by inducing crystallization, optionally after concentration of the filtrate. The raw N-substituted 1H-pyrazole-5-carbonylchloride compound I thus obtained can be used directly in step (iii) of the process according to the second aspect of the invention or sent to other uses. Alternatively, it can be retained for a later use or further purified beforehand. For further purification, it is possible to use one or more methods known to those skilled in the art, for example recrystallization, distillation, sublimation, zone melting, melt crystallization or chromatography. It is however preferred to subject compound II to a subsequent synthetic step in the form of the raw material obtained directly after the workup procedure.

The compounds of formula (II) are known e.g. from WO 2003/015519 or WO 2003/106427 or they can be prepared by analogy to the methods described therein or in WO 2008/126858, WO 2008/126933, WO 2008/130021, WO 2007/043677 and Bioorganic and Medicinal Chemistry Letters 2005, 15, 4898-4906.

According to further embodiments of the invention the compounds of formula (II'), that differ from compounds of formula (II) by having a substituent $R^{1a}$ instead of a substituent $R^1$, can e.g. be prepared by the reaction sequence depicted in the following scheme 1.

Scheme 1:

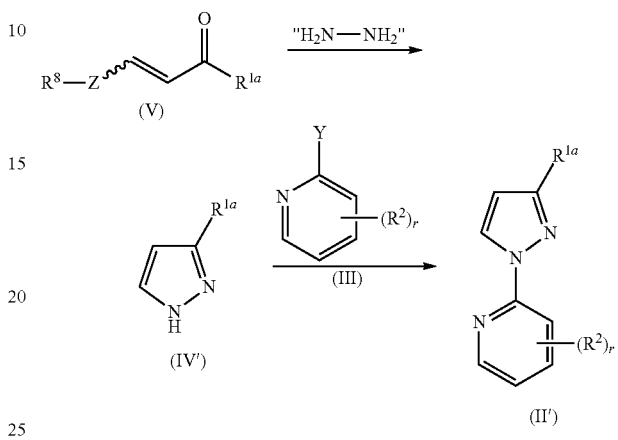

In scheme 1, the variables r and $R^2$ are as defined above. The variables Z, Y, $R^{1a}$ and $R^8$ have the following meanings:

Z is O or S or $NR^9$;

Y is a suitable leaving group such as halogen, $C_1$-$C_3$-alkoxy, $C_1$-$C_3$-alkylthio, $C_1$-$C_3$-haloalkoxy, $C_1$-$C_3$-haloalkylthio, —S(O)$R^b$, —S(O)$_2R^b$, —OS(O)$R^b$, —OS(O)$_2R^b$ and —NO$_2$, where $R^b$ has one of the meanings given for $R^b$ above, and where $R^b$ is in particular $C_1$-$C_4$-alkyl, $C_1$-$C_4$-haloalkyl or phenyl, which is unsubstituted or which carries 1, 2 or 3 radicals selected from halogen and $C_1$-$C_4$-alkyl, and where Y is in particular halogen, —S(O)$_2R^b$ or —OS(O)$R^b$, where $R^b$ is as defined above, and where $R^b$ is in particular $C_1$-$C_4$-alkyl;

$R^{1a}$ has one of the meanings given for $R^1$, as defined herein and in the claims, with the exception of halogen, cyano and —SF$_5$ and where $R^{1a}$ is in particular selected from $C_1$-$C_4$-fluoroalkyl, CBrF$_2$ and $C_1$-$C_4$-fluoroalkoxyalkyl, such as CH$_2$OCHF$_2$, and in especially selected from the group consisting of CF$_3$, CHF$_2$, CBrF$_2$ and CH$_2$OCHF$_2$;

$R^8$ is selected from the group consisting of $C_1$-$C_6$-alkyl, $C_1$-$C_6$-cycloalkyl, $C_1$-$C_6$-haloalkyl and $C_1$-$C_6$-halocycloalkyl; and where $R^8$ is in particular $C_1$-$C_6$-alkyl;

$R^g$ if present, is selected from the group consisting of $C_1$-$C_6$-alkyl, $C_3$-$C_8$-cycloalkyl, $C_1$-$C_6$-haloalkyl and $C_1$-$C_6$-cyclohaloalkyl, with preference for R9 being $C_1$-$C_6$-alkyl, or for Z being $NR^g$ the moiety Z—$R^8$ may also form a 5- to 7-membered saturated N-bound heterocyclic radical, which in addition to the nitrogen atom may have one further heteroatom or heteroatom moiety as ring member, where the further heteroatom or heteroatom moiety is selected from the group consisting of O, S and N—($C_1$-$C_4$-alkyl), examples of such heterocyclic radicals including 1-pyrrolidinyl, 1-piperidinyl, 1-methyl-4-piperazinyl, 4-morpholinyl and 4-thiomorpholinyl.

The reaction of scheme 1 is particularly successful, if the variables r, Z, Y, $R^8$, $R^{1a}$ and $R^2$ on their own and in particular in combination have the following meanings:

r is 1;
Z is O;
Y is halogen, —S(O)$_2$R$^b$ or —OS(O)R$^b$, where R$^b$ is as defined above, and where R$^b$ is in particular $C_1$-$C_4$-alkyl;
$R^8$ is $C_1$-$C_6$-alkyl;
$R^{1a}$ is selected from the group consisting of $C_1$-$C_4$-fluoroalkyl, CBrF$_2$ and $C_1$-$C_4$-fluoroalkoxyalkyl, such as CH$_2$OCHF$_2$, and in particular selected from the group consisting of CF$_3$, CHF$_2$, CBrF$_2$ and CH$_2$OCHF$_2$;
$R^2$ is selected from the group consisting of halogen and $C_1$-$C_4$-fluoroalkyl, in particular selected from the group consisting of halogen and CF$_3$, with particular preference given to compounds of the formula III, wherein r is 1 and where $R^2$ is located in the ortho position with regard to the point of attachment of the substituent Y. In this case, $R^2$ is in particular selected from the group of halogen and $C_1$-$C_4$-fluoroalkyl, especially selected from the group consisting of halogen and CF$_3$, and more particularly $R^2$ is chlorine.

The reaction of scheme 1 may also be particularly successful, if the variables r, Z, Y, $R^8$, $R^{1a}$ and $R^2$ on their own and in particular in combination have the following meanings:

r is 1;
Z is NR$^9$;
Y is halogen, —S(O)$_2$R$^b$ or —OS(O)R$^b$, where R$^b$ is as defined above, and where R$^b$ is in particular $C_1$-$C_4$-alkyl;
$R^8$ is $C_1$-$C_6$-alkyl;
R$^g$ is $C_1$-$C_6$-alkyl; or for Z being NR$^g$ the moiety Z—R$^8$ may also form a 5- to 7-membered saturated N-bound heterocyclic radical, which is selected from 1-pyrrolidinyl, 1-piperidinyl, 1-methyl-4-piperazinyl, 4-morpholinyl and 4-thiomorpholinyl;
$R^{1a}$ is selected from the group consisting of $C_1$-$C_4$-fluoroalkyl, CBrF$_2$ and $C_1$-$C_4$-fluoroalkoxyalkyl, such as CH$_2$OCHF$_2$, and in particular selected from the group consisting of CF$_3$, CHF$_2$, CBrF$_2$ and CH$_2$OCHF$_2$;
$R^2$ is selected from the group consisting of halogen and $C_1$-$C_4$-fluoroalkyl, in particular selected from the group consisting of halogen and CF$_3$, with particular preference given to compounds of the formula III, wherein r is 1 and where $R^2$ is located in the ortho position with regard to the point of attachment of the substituent Y. In this case, $R^2$ is in particular selected from the group of halogen and $C_1$-$C_4$-fluoroalkyl, especially selected from the group consisting of halogen and CF$_3$, and more particularly $R^2$ is chlorine.

Thus, in a first step the process of scheme 1 comprises reacting a compound of formula V with hydrazine or hydrazine hydrate or a salt thereof. In a second step the thus obtained pyrazole compound of formula IV' is reacted with a pyridine compound III to yield the compound of formula (II'). The reactions of the first and the second step can be performed by analogy to the methods described in WO 2008/126858, WO 2008/126933, WO 2008/130021, WO 2007/043677 and Bioorganic and Medicinal Chemistry Letters 2005, 15, 4898-4906.

According to the first reaction depicted in scheme 1, a compound of formula V is reacted with hydrazine or hydrazine hydrate or a salt thereof. The reaction is usually achieved by contacting the compound of formula V with hydrazine or hydrazine hydrate or a salt thereof in a solvent.

Suitable solvents include water and polar protic organic solvents and mixtures thereof. Examples of suitable polar protic solvents, which can be used in step 1 of scheme 1 are in particular alcohols, such as $C_1$-$C_4$-alkanols, $C_2$-$C_4$-alkandiols, e.g. ethylene glycol or propylene glycol, di- and tri-$C_2$-$C_3$-alkylene ethers, such as diethylene glycol or triethylene glycol, mono-$C_1$-$C_4$-alkylethers, in particular monomethylethers of $C_2$-$C_4$-alkandiols, e.g. ethylene glycol monomethyl ether, or mono-$C_1$-$C_4$-alkylethers, in particular monomethylethers of di- or tri-$C_2$-$C_3$-alkylene ethers and mixtures thereof. Preferred organic solvents are selected from the group of $C_1$-$C_4$-alkanols with particular preference given to ethanol.

The hydrazine or hydrazine salt is preferably employed in an amount of from 0.7 to 10 mol, preferably from 0.9 to 5 mol and in particular from 1 to 3 mol per mol of the compound of formula (V).

It has been found advantageous to carry out the first reaction of scheme 1 in the presence of an acid. The acid may be used in catalytic or stoichiometric amounts. The amount of acid may preferably be used in catalytic amounts, in particular in an amount from 0.001 to 0.2 mol, especially in an amount from 0.01 to 0.1 mol per mol of compound V but it is also be possible to use the acid in higher amounts. Suitable acids are in particular strong acids such as hydrochloric acid, sulphuric acid, nitric acid, or organic sulfonic acids such as alkylsulfonic acids or arylsulfonic acids. It is possible to ad the base separately but it is also possible to add the acid by using a salt of hydrazine with a strong acid, e.g. by using the mono- or dihydrocloride of hydrazine.

The reaction according to the first reaction depicted in scheme 1 is generally performed at a temperature in the range of from 0 to 150° C., preferably from 10 to 120° C. In principle, the reaction temperature can be as high as the boiling point of the reaction mixture at the given reaction pressure. The reaction pressure is generally not critical and may range from 0.9 to 2 bar, in particular from 0.9 to 1.5 bar and especially from 0.9 to 1.1 bar.

The thus obtained pyrazole can be isolated from the reaction mixture by conventional techniques, e.g. by distillation or extraction. The acid, if present, may be neutralized prior to isolation of the pyrazole compound but it may also be possible to isolate the pyrazole compound from the acidic reaction mixture, e.g. by distillation.

According to the second reaction depicted in scheme 1, a compound of formula (III) is reacted with the pyrazole compound IV. The amount of compound IV is generally from 0.8 to 1.2 mol, in particular from 0.9 to 1.1 mol per mol of compound III.

The reaction is usually achieved by contacting the compound of formula (IV) with the compound III in a solvent. In particular embodiments of the invention, the second reaction depicted in scheme 1 is carried out in an aprotic organic solvent or a mixture of aprotic organic solvents. Examples of suitable aprotic solvents are halogenated alkanes, such as methylene chloride, chloroform or 1,2-dichlorethane, aromatic hydrocarbons, such as toluene, xylenes or chlorobenzene, open-chained ethers, such as diethylether, methyl-tert-butyl ether, diisopropyl ether or methyl-isobutyl ether, cyclic ethers, such as tetrahydrofuran, 1,4-dioxane or 2-methyl tetrahydrofuran, N,N-di-$C_1$-$C_4$-alkylamides of aliphatic carboxylic acids such as N,N-dimethyl formamide, N,N-dimethyl acetamide, N—$C_1$-$C_4$-alkyl lactames such as N-methylpyrrolidinone, sulfoxides such as dimethylsulfoxide, nitriles such acetonitrile or propionitrile and pyridines such as pyridine, 2,6-dimethylpyridine or 2,4,6-trimethylpyridine. Preferably the reaction is carried out a polar aprotic solvent, in particular in a solvent selected from N,N-di-$C_1$-$C_4$-alkylamides of aliphatic carboxylic acids such as N,N-dimethyl formamide or N,N-dimethyl acetamide, and N—$C_1$-$C_4$-alkyl lactames such as N-methyl pyrrolidinone.

It has been found advantageous to carry out the second reaction of scheme 1 in the presence of a base. The base may be used in catalytic or stoichiometric amounts. The amount of base may preferably be used in at least almost stoichiometric amounts, e.g. in an amount from 0.9 to 5 mol in particular in an amount from 1 to 2 mol per mol of compound IV. Suitable bases are in particular oxo bases. Suitable oxo bases include but are not limited to hydroxides, in particular alkalimetal hydroxides such as lithium, sodium or potassium hydroxide, carbonates, in particular alkalimetal carbonates, such as lithium, sodium or potassium carbonates, hydrogen carbonates, in particular alkalimetal hydrogen carbonates, such as lithium, sodium or potassium hydrogen carbonates, phosphates or hydrogenphosphates, in particular alkalimetal phosphates or hydrogenphosphates, such as lithium, sodium or potassium phosphate, or lithium, sodium or potassium hydrogen phosphate, alkoxides, in particular alkalimetal alkoxides such as sodium or potassium methoxide, sodium or potassium ethoxide or sodium or potassium tert-butanolate, carboxylates, in particular alkalimetal carboxylates, such as lithium, sodium or potassium formiate, lithium, sodium or potassium acetate or lithium, sodium or potassium propionate. Suitable amine bases include but are not limited to ammonia and organic amines, in particular aliphatic or cycloaliphatic amines, e.g. di-$C_1$-$C_4$-alkylamines, tri-$C_1$-$C_4$-alkylamines, $C_3$-$C_6$-cycloalkylamines, $C_3$-$C_6$-cycloalkyl-di-$C_1$-$C_4$-alkylamines or cyclic amines such as dimethylamine, diethylamine, diisopropylamine, cyclohexylamine, dimethylcyclohexylamine, trimethylamine, diethylamine or triethylamine, piperidine and N-methylpiperidine. Preferred bases are alkalimetal carbonates, especially sodium, potassium and cesium carbonate.

The reaction according to the second reaction depicted in scheme 1 is generally performed at a temperature in the range of from 50 to 200° C., preferably from 80 to 180° C. In principle the reaction temperature can be as high as the boiling point of the reaction mixture at the given reaction pressure. The reaction pressure is generally not critical and may range from 0.9 to 2 bar, in particular from 0.9 to 1.5 bar and especially from 0.9 to 1.1 bar.

The compound of formula (II') formed in this reaction can be isolated from the reaction mixture by customary methods, e.g. by distillation or by crystallization or precipitation from the reaction mixture, preferably after having removed insoluble byproducts. The compound of formula II' can also be isolated from the reaction mixture by addition of water to the reaction mixture and extracting the thus obtained mixtures with a suitable solvent. Suitable solvents for extraction purposes are essentially immiscible with water and are capable of dissolving sufficient amounts of compound II'. It is also possible to concentrate the reaction mixture by distilling off the solvent, mixing the thus obtained residue with water and extracting the thus obtained mixture with a suitable solvent. Examples of suitable solvents are aliphatic hydrocarbons, such as alkanes, e.g. pentane, hexane or heptane, cycloaliphatic hydrocarbons, such as cycloalkanes, e.g. cyclopentane or cyclohexane, halogenated alkanes, such as methylene chloride or chloroform, aromatic hydrocarbons, such as benzene, toluene, the xylenes or chlorobenzene, open-chained ethers, such as diethylether, methyl-tert-butyl ether or methyl-isobutyl ether, or esters, such as ethyl acetate or ethyl propionate.

The isolated product II' can be further purified, e.g. by crystallization or distillation. However, frequently, the product is already obtained in a purity which does not require further purification steps.

Vinyl (thio)ether compounds of formula V are either commercially available on a large scale or easily produced using standard methods of organic chemistry, a skilled person is familiar with. Likewise, the compounds of formula (III) are readily available or can be prepared by analogy to routine methods of organic chemistry.

In step (iii) of the process according to the second aspect of the invention for preparing a sulfimine compound of formula (VI), a compound of formula (VII) is reacted with a pyrazole compound of formula (I) to yield a compound of formula (VI). The reaction of step (iii) can be carried out by analogy to conventional amidation reactions of carboxylic acid chlorides with aromatic amines as described e.g. in WO 2003/015519, WO 2006/062978, WO 2008/07158 or WO 2009/111553. Surprisingly, the group N=S(O)$_r$R$^6$R$^7$ does not interfere with the amidation reaction. Rather, the compounds of formula VI, can be obtained in high yields with high purity.

Usually, the compounds of formula (VII) and the compounds of formula (I) are preferably employed in stoichiometric or almost stoichiometric amount. Generally, the relative molar ratio of the compounds of formula (VII) to the compounds of formula (I) will be in a range from 1.1:1 to 1:2, preferably from 1.1:1 to 1:1.2 and in particular from 1.05:1 to 1:1.1.

It has been found advantageous to carry out the reaction of step (iii) in the presence of a base. Suitable bases include bases which are soluble or insoluble in the reaction medium. The base may be used in catalytic or stoichiometric amounts. The amount of base may preferably be in the range from 0.9 to 2 mol, in particular from 1 to 1.8 mol per mol of compound I.

Suitable bases include but are not limited to oxo bases and amine bases. Suitable oxo bases include but are not limited to carbonates, in particular alkali metal carbonates, such as lithium, sodium or potassium carbonates, phosphates, in particular alkalimetal phosphates, such as lithium, sodium or potassium phosphate. Suitable amine bases include but are not limited to tertiary organic amines, in particular aliphatic or cycloaliphatic tertiary amines, e.g. tri-$C_1$-$C_4$-alkylamines, $C_3$-$C_6$-cycloalkyl-di-$C_1$-$C_4$-alkylamines, tertiary cyclic amines and pyridines such as dimethylcyclohexylamine, trimethylamine, triethylamine, N-methylpiperidine, N-methylmorpholine, pyridine, 2,6-dimethylpyridine, 2,4,6-trimethylpyridine or quinoline. Preferred bases are alkalimetal carbonates, such as lithium, sodium or potassium carbonates and tertiary amines in particular triethylamine, pyridine, 2,6-dimethylpyridine or 2,4,6-trimethylpyridine.

In addition to or instead of the base, an amidation catalyst can be used. Suitable amidation catalysts are dialkylaminopyridines such as 4-(N,N-dimethylamino)pyridine (4-DMAP). The catalyst is usually employed in amounts from 0.001 to 1 mol, in particular from 0.005 to 0.2 mol, especially from 0.01 to 0.1 mol per mol of compound of formula (I).

In particular embodiments of the invention, the reaction of step (iii) is carried out in an organic solvent or a mixture of organic solvents. Suitable solvents for carrying out the reaction of step (iii) are preferably aprotic solvents and mixtures thereof. Examples of aprotic solvents are aliphatic hydrocarbons, such as alkanes, e.g. pentane, hexane or heptane, octane, cycloaliphatic hydrocarbons, such as cycloalkanes, e.g. cyclopentane or cyclohexane, halogenated alkanes, such as methylene chloride, chloroform or 1,2-dichlorethane, aromatic hydrocarbons, such as benzene, toluene, the xylenes, mesitylene or chlorobenzene, open-chained ethers, such as diethylether, methyl-tert-butyl ether, diisopropyl ether or methyl-isobutyl ether, cyclic ethers, such as tetrahydrofuran, 1,4-dioxane or 2-methyl tetrahydrofuran, nitriles, such as acetonitrile or propionitrile, the aforementioned pyridines such as pyridine, 2,6-dimethylpyridine or 2,4,6-trimethylpyridine, N,N-di-$C_1$-$C_4$-alkylamides of aliphatic carboxylic acids such as N,N-dimethylformamide, N,N-dimethylacetamide, and N—$C_1$-$C_4$-alkyl lactames such as N-methylpyrrolidinone. Particular preferred solvents for carrying out reaction of step (iii) are cyclohexane, dichloromethane, chlorobenzene, toluene, pyridine, tetrahydrofurane and N,N-dimethyl formamide, and mixtures thereof.

The reaction according to step (iii) of the inventive process is generally performed at a temperature in the range of from −40 to +150° C., preferably from 0 to 110° C. and more preferably from 20 to 80° C. In principle the reaction temperature can be as high as the boiling point of the reaction mixture at the given reaction pressure, but is preferably kept at the indicated lower values. The reaction pressure is generally not critical and may range from 0.9 to 2 bar, in particular from 0.9 to 1.5 bar and especially from 0.9 to 1.1 bar.

The reaction of step (iii) is carried out by reacting compound of formula (VII) with a suitable amount of a compound of formula (I) under the above reaction conditions. The reaction can be performed for example in the following manner: a solution or a suspension of the base and of the compound of formula (VII) in a suitable organic solvent is charged to a suitable reaction vessel. To this mixture, the compound of formula (I) is added, preferably as a solution or suspension in an organic solvent. Addition of the compound of formula (I) may be done as a single portion or preferably continuously or in several portions. To the resulting mixture, the catalyst may be added, if desired. The catalyst may be added either neat, in solution or as a suspension in a suitable organic solvent.

The compound of formula (VI) formed in reaction of step (iii) can be isolated from the reaction mixture by customary methods, e.g. by removal of the base from the reaction mixture by either filtration or extraction with water, followed by concentration by distilling off the solvent. Alternatively, the reaction mixture can be diluted with water and cooled to a temperature between −30 and +30° C. to precipitate the amide compound from the solvent or solvent mixture. The precipitated amide compound VI can be separated from the liquid reaction mixture by conventional means, e.g. by filtration, centrifugation etc. The amide compound of formula VI can also be isolated from the reaction mixture by addition of water to the reaction mixture and extracting the thus obtained mixtures with a suitable solvent. Suitable solvents for extraction purposes are essentially immiscible with water and are capable of dissolving sufficient amounts of compound VI. It is also possible to concentrate the reaction mixture by distilling of the solvent, mixing the thus obtained residue with water and extracting the thus obtained mixture with a suitable solvent. Examples of suitable solvents are aliphatic hydrocarbons, such as alkanes, e.g. pentane, hexane or heptane, cycloaliphatic hydrocarbons, such as cycloalkanes, e.g. cyclopentane or cyclohexane, halogenated alkanes, such as methylene chloride or chloroform, aromatic hydrocarbons, such as benzene, toluene, the xylenes or chlorobenzene, open-chain ethers, such as diethylether, diisopropyl ether, di-n-propyl ether, di-n-butyl ether, methyl-tert-butyl ether, ethyl-tert.-butyl ether or methyl-isobutyl ether, or esters, in particular $C_1$-$C_4$ alkyl esters of acetic acid or propionic acid such as ethyl acetate, butyl acetate or ethyl propionate.

The thus obtained compound of formula (VI) can be further purified, e.g. by crystallization or by chromatography or combined measures. However, frequently, the product is already obtained in a purity which does not require further purification steps.

The invention relates to a process for preparing a compound of the formula (VII). This process is hereinafter termed "process VII". According to a first embodiment, process VII comprises reacting a compound of the formula (VIII) with a compound of formula (IX). According to a second embodiment, process VII comprises reacting a compound of the formula (VIII) with a compound of formula (X).

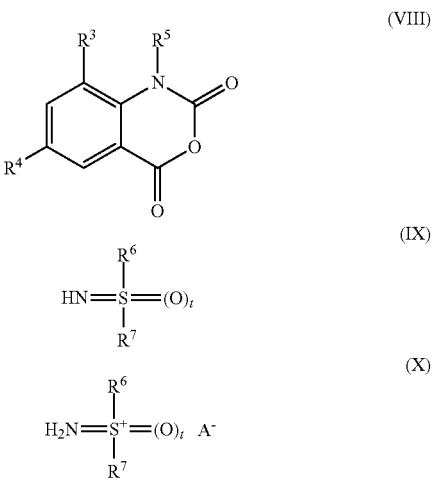

where $R^3$, $R^4$, $R^5$, t, $R^6$ and $R^7$ are as defined herein and in the claims and where $A^-$ is an equivalent of an anion having a $pK_B$ of at least 10, as determined under standard conditions (298 K; 1.013 bar) in water.

For the conversion in process VII particular preference is given to compounds of the formula (VIII) wherein $R^5$ is as defined herein and in the claims and where $R^3$ has one of the meanings given herein and in the claims or is hydrogen, and $R^4$ has one of the meanings given herein and in the claims or is hydrogen. Preferably, the radical $R^3$ and $R^4$ in formula (VIII) are, independently of each other, selected from the group consisting of hydrogen, halogen, $C_1$-$C_4$-alkyl, $C_1$-$C_4$-haloalkyl and cyano, it being possible that $R^3$ and $R^4$ are identical or different.

In the process VII of the present invention, preference is given to compounds of the formulae (IX) and (X), where the variable t is 0 and where $R^6$ and $R^7$, independently of each other, are selected from the group consisting of $C_1$-$C_6$-alkyl, $C_1$-$C_6$-haloalkyl, $C_3$-$C_6$-cycloalkyl, $C_3$-$C_6$-halocycloalkyl, $C_2$-$C_6$-alkenyl, $C_2$-$C_6$-haloalkenyl, wherein alkyl, alkenyl and cycloalkyl may optionally be substituted by one or more, e.g. 1 or 2 radicals $R^a$, where $R^a$ is as defined above and in particular has one of the preferred meanings given above for $R^a$. Particular preference is given to compounds of the formulae (IX) and (X), where the variable t is 0 and where $R^1$ and $R^2$, independently of each other, are more preferably selected from the group consisting of $C_1$-$C_6$-alkyl, $C_3$-$C_6$-cylcoalkyl and $C_3$-$C_6$-cycloalkyl-$C_1$-$C_4$-alkyl.

Likewise, preference is given to compounds of the formulae (IX) and (X), where the variable t is 0 and where $R^1$ and $R^2$ together represent a $C_4$-$C_6$-alkylene or $C_4$-$C_6$-alkenylene group forming together with the sulfur atom to which they are attached a 5-, 6- or 7-membered, saturated or partially unsaturated ring, wherein 1 or 2 of the $CH_2$ groups in the $C_4$-$C_6$-alkylene chain or 1 or 2 of any of the $CH_2$ or CH groups in the $C_4$-$C_6$-alkenylene chain may be replaced may be replaced by 1 or 2 groups independently selected from the group consisting of O, S, N and NH. Particular preference is also given to compounds of the formulae (IX) and (X), where the variable t is 0 and where $R^1$ and $R^2$ together preferably represent a $C_4$-$C_6$-alkylene group forming together with the sulfur atom to which they are attached a 5-, 6- or 7-membered saturated ring.

In the compounds of formula (X), $A^-$ is an equivalent of an anion having a $pK_B$ of at least 10, as determined under standard conditions (298 K; 1.013 bar) in water. In this context "equivalent" means the amount of anion required to achieve electroneutrality. For example, if the anion carries one negative charge the equivalent is 1, while if the anione carries two negative charges the equivalent is ½. Suitable anions are those, which have a basicity constant $pK_B$ of at least 10, in particular at least 12 as determined under standard conditions (298 K; 1.013 bar) in water. Suitable anions include inorganic ions such as $SO_4^{2-}$, $HSO_4^-$, $Cl^-$, $ClO_4^-$, $BF_4^-$, $PF_6^-$, $HPO_4^-$, and organic anions such as methylsulfonate, trifluoromethylsulfonate, trifluoroacetate, phenylsulfonate, toluenesulfonate, mesitylene sulfonate and the like.

In process VII, the compounds of formulae (IX) or (X), respectively, are typically employed in an amount of from 0.9 to 2 mol, preferably from 0.9 to 1.5 mol, more preferably from 0.9 to 1.2 mol and in particular from 0.95 to 1.1 mol per mol of the compound of formula (XIII) used in process VII.

It has been found advantageous to carry out the reaction of process VII in the presence of a base. Suitable bases include bases which are soluble or insoluble in the reaction medium. The base may be used in catalytic or stoichiometric amounts. The amount of base may preferably be in the range from 0.1 to 2 mol, in particular from 0.9 to 1.5 mol per mol of compound VIII or in the range from 0.1 to 2 mol, in particular from 0.9 to 1.5 mol per mol of compound Ix or X. In a particular embodiment the base is used in an amount of at least 0.9 mol, in particular at least 1 mol, e.g. from 0.9 to 2 mol, in particular from 1 to 1.5 mol per mol of compound VIII, in particular, if a compound of formula (X) is used.

Suitable bases include but are not limited to oxo bases and amine bases. Suitable oxo bases include but are not limited to those mentioned in context with the reaction of scheme 1 herein before. Preferred bases are oxo bases, in particular alkalimetal alkoxides, which are also termed alkalimetal alkanolates, especially sodium and potassium alkanolates such as sodium methoxides, potassium methoxide, sodium ethoxide, potassium ethoxide, sodium tert-butanolate or potassium tert-butanolate. Mixtures of oxo bases and amine bases may also be used. Likewise preferred are bases which are selected from the aforementioned amine bases, in particular from the aforementioned tertiary amines.

In particular embodiments of the invention, the reaction of process VII is carried out in an organic solvent or a mixture of organic solvents. Suitable solvents for carrying out reaction VII may be protic or aprotic solvents and mixtures thereof, with aprotic solvents being preferred. Examples of aprotic solvents are aliphatic hydrocarbons, such as alkanes, e.g. pentane, hexane or heptane, cycloaliphatic hydrocarbons, such as cycloalkanes, e.g. cyclopentane or cyclohexane, halogenated alkanes, such as methylene chloride, chloroform or 1,2-dichlorethane, aromatic hydrocarbons, such as benzene, toluene, the xylenes or chlorobenzene, open-chain ethers, such as diethylether, methyl-tert-butyl ether, diisopropyl ether or methyl-isobutyl ether, cyclic ethers, such as tetrahydrofuran, 1,4-dioxane or 2-methyl tetrahydrofuran, esters, in particular the aforementioned $C_1$-$C_4$-alkyl acetates and propionates such as ethyl acetate, butyl acetate or ethyl propionate, aliphatic or alicyclic carbonates such as diethyl carbonate, ethylene carbonate (1,3-dioxolan-2-on) or propylene carbonate (4-methyl-1,2-dioxolan-2-on). Suitable aprotic solvents may also be pyridines such as pyridine, 2,6-dimethylpyridine or 2,4,6-trimethylpyridine, N,N-di-$C_1$-$C_4$-alkylamides of aliphatic carboxylic acids such as N,N-dimethyl formamide, N,N-dimethyl acetamide, and N—$C_1$-$C_4$-alkyl lactames such as N-methylpyrrolidinone. Examples for polar protic solvents are $C_1$-$C_4$-alkanols, such as methanol, ethanol, propanol or isopropanol, $C_2$-$C_4$-alkandiols, such as ethylene glycol or propylene glycol, ether alkanols, such as diethylene glycol, sulfoxides, such as dimethyl sulfoxide, and mixtures thereof. Preferably the reaction is carried out in an aprotic solvent or a mixture of aprotic solvents.

The reaction according to process VII is generally performed at a temperature in the range of from −40 to +150° C., preferably from 0 to 110° C. and more preferably from 0 to 80° C. In principle the reaction temperature can be as high as the boiling point of the reaction mixture at the given reaction pressure, but is preferably kept at the indicated lower values. The reaction pressure is generally not critical and may range from 0.9 to 2 bar, in particular from 0.9 to 1.5 bar and especially from 0.9 to 1.1 bar.

The reaction of process VII is carried out by reacting compound VIII with a suitable amount of a compound of formulae (IX) or (X) under the above reaction conditions. The reaction can be performed for example in the following manner: a solution or a suspension of the compound of formula (VIII) in a suitable organic solvent is added to a suitable reaction vessel. To this mixture, the compound of formulae (IX) or (X) is added, preferably as a solution or suspension in an organic solvent. Addition of compound IX or X may be done as a single portion or preferably continuously or in several portions. To the resulting mixture, the base may be added, if desired. The base may be added either neat, in solution or as a suspension in a suitable organic solvent. Addition of the base may be done as a single portion or preferably continuously or in several portions. It is also possible to add the compound and, if desired, the base at the same time.

The compound of formula (VII) formed in reaction of process VII can be isolated from the reaction mixture by customary methods, e.g. by the addition of water and subsequent extraction with a suitable solvent, followed by concentration by distilling off the solvent. Suitable solvents for extraction purposes are essentially immiscible with water and capable of dissolving the compound of formula VII. Examples are aliphatic hydrocarbons, such as alkanes, e.g. pentane, hexane or heptane, cycloaliphatic hydrocarbons, such as cycloalkanes, e.g. cyclopentane or cyclohexane, halogenated alkanes, such as methylene chloride or chloroform, aromatic hydrocarbons, such as benzene, toluene, the xylenes or chlorobenzene, open-chained ethers, such as diethylether, methyl-tert-butyl ether or methyl-isobutyl ether, or esters, such as ethyl acetate or ethyl propionate.

The isolated product can be further purified, e.g. by crystallization or by chromatography or combined measures. However, frequently, the product is already obtained in a purity which does not require further purification steps.

The compounds of formulae (IX) and (X) are known from prior art, e.g. from WO 2007/006670; WO 2008/141843; Y. Tamura et al, Tetrahedron 1975, 31, 3035-3040; Fujii et al., Heteroatom Chemistry 2004, 15(3), 246-250; Johnson et al., J. Org. Chem. 1989, 54, 986-988; Yoshimura et al., J. Org. Chem. 1976, 41, 1728-1733; Appel et al., Chem. Ber. 1962, 95, 849-854 and Chem. Ber. 1966, 99, 3108-3117; or from Young et al, J. Org. Chem. 1987, 52, 2695-2699; or they can be prepared by analogy to the methods described therein or by analogy to the methods described in WO 2008/141843, U.S. Pat. No. 6,136,983 and the literature cited therein.

A particular suitable method for preparing the compounds of formula (X) is described scheme 2 below.

Scheme 2:

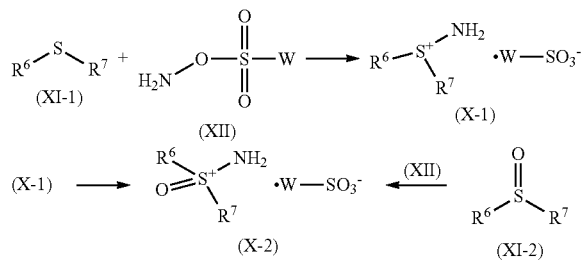

In scheme 2, $R^6$ and $R^7$ are as defined above. W can be any group which does not disturb the reaction, such as OH, $NH_2$, $C_1$-$C_4$-alkyl, $C_1$-$C_4$-haloalkyl, aryl or hetaryl, where the last two radicals are unsubstituted or substituted by 1, 2 or 3 radicals $R^e$, which are preferably selected from halogen and $C_1$-$C_4$-alkyl. W is preferably OH or preferably an aromatic group such as phenyl, optionally substituted with one or more radicals selected from halogen and $C_1$-$C_4$-alkyl, for example phenyl, 4-methylphenyl or 2,4,6-trimethylphenyl. In a particular embodiment W is OH.

According to the first reaction depicted in scheme 2, a sulfonyl hydroxylamine of formula (XII) is reacted with a sulfide of formula (XI-1), yielding a compound of formula (X-1) which corresponds to a compound of formula X, where t=0. The reaction can be performed by contacting the compounds of formula (XI) and (XII).

The compound of formula (XII) is preferably employed in an amount of from 0.7 to 1.1 mol, preferably from 0.8 to 1.0 mol and in particular from 0.85 to 0.99 mol per mol of the compound of formula (XI-1).

It has been found advantageous to carry out the first reaction of scheme 2 in the presence of a base. The base may be used in catalytic or stoichiometric amounts. The amount of base may preferably be in the range from 0.9 to 2 mol, in particular from 0.9 to 1.5 mol per mol of compound II or in the range from 1.0 to 1.2 mol per mol of compound XII.

Suitable bases include in particular oxo bases. Suitable oxo bases include but are not limited to those mentioned in context with the reaction of step (iii). Preferred bases alkalimetal alkoxides, especially sodium and potassium alkanolates, such as sodium methoxides, potassium methoxide, sodium ethoxide, potassium ethoxide, sodium tert-butanolate or potassium tert-butanolate.

In particular embodiments of the invention, the first reaction depicted in scheme 2 is carried out in an organic solvent or a mixture of organic solvents. Suitable solvents include but are not limited to polar protic or aprotic solvents and mixtures thereof, with protic solvents being preferred. Examples of polar aprotic solvents are halogenated alkanes, such as methylene chloride, chloroform or 1,2-dichlorethane, halogenated aromatic hydrocarbons, such as chlorobenzene, open-chained ethers, such as diethylether, methyl-tert-butyl ether, diisopropyl ether or methyl-isobutyl ether, cyclic ethers, such as tetrahydrofuran, 1,4-dioxane or 2-methyl tetrahydrofuran, or esters, such as ethyl acetate or ethyl propionate, N,N-di-$C_1$-$C_4$-alkylamides of aliphatic carboxylic acids such as N,N-dimethyl formamide, N,N-dimethyl acetamide, and N—$C_1$-$C_4$-alkyl lactames such as N-methylpyrrolidinone. Examples for polar protic solvents are $C_1$-$C_4$-alkanols such as methanol, ethanol, propanol and isopropanol, $C_2$-$C_4$-alkandiols, such as ethylene glycol or propylene glycol, and ether alkanols such as diethylene glycol, and mixtures thereof. Preferably the reaction is carried out in a protic solvent or a mixture thereof with an aprotic solvent. In particular, the solvent is a $C_1$-$C_4$-alkanol or a mixture of $C_1$-$C_4$-alkanols.

The reaction according to the first reaction depicted in scheme 2 is generally performed at a temperature in the range of from −50 to +20° C., preferably from −40 to 10° C. and more preferably from −40 to +5° C. The reaction pressure is generally not critical and may range from 0.9 to 2 bar, in particular from 0.9 to 1.5 bar and especially from 0.9 to 1.1 bar.

The first reaction of scheme 2 is carried out by reacting compound XI-1 with a suitable amount of a compound of formulae XII under the above reaction conditions. The reaction can be performed for example in the following manner: a solution or a suspension of a compound of formula (XI-1), optionally containing a base, in a suitable organic solvent is charged to a suitable reaction vessel. To this mixture the compound XII, preferably as a solution or suspension in an organic solvent is added at the above temperatures. Addition of compound XII may be done as a single portion or preferably continuously or in several portions.

The compound of formula (X-1) formed in this reaction can be isolated from the reaction mixture by customary methods, e.g. by crystallization or precipitation from the reaction mixture, preferably after having removed insoluble by products. Precipitation or crystallization may be achieved by concentration of the reaction mixture, cooling the reaction mixture or addition of an "anti-solvent" to the reaction mixture. Anti-solvents are organic solvents, wherein the compound X-1 is insoluble or only sparingly soluble. Suitable anti-solvents include but are not limited to aliphatic hydrocarbons, such as alkanes, e.g. pentane, hexane or heptane, cycloaliphatic hydrocarbons, such as cycloalkanes, e.g. cyclopentane or cyclohexane, aromatic hydrocarbons, such as benzene, toluene, the xylenes or chlorobenzene and open-chained ethers, such as diethylether, methyl-tert-butyl ether or methyl-isobutyl ether.

The isolated product can be further purified, e.g. by crystallization or tituration with a solvent, e.g. with acetonitrile. However, frequently, the product is already obtained in a purity which does not require further purification steps.

Compounds of formula (X), in which t is 1 (compounds X-2), may be prepared from compounds of formula (X-1) by oxidation with an appropriate oxidant, in analogy to described methods as described by, for example, Dillard et al, Journal of Medicinal Chemistry 1980, 23, 717-722. The compounds of formula (X-2) may also be prepared by reacting a sulfoxide XI-2 with an amination agent, such as a compound XII, in particular aminoxysulfonic acid NH$_2$OSO$_3$H, under similar conditions as described for the reaction of XI-1 with XII.

The compounds of formula (VIII) are known from prior art, e.g. from WO 2003/016284 and Coppola, Synthesis 1980, pp. 505-536, or they can be prepared by analogy to the methods described therein. The compounds VIII can also be prepared by reacting an anthranilic acid derivative XIII with carbonic ester or an equivalent thereof such as phosgene, diphosgene (trichloromethyl chloroformate), triphosgene (bis(trichloromethyl)carbonate), dialkyl carbonates, or alkyl chloroformiates as depicted in scheme 3.

Scheme 3:

In scheme 3, R$^3$, R$^4$ and R$^5$ are as defined above. L$^1$ is halogen, in particular chlorine, C$_1$-C$_4$-alkoxy, in particular methoxy or ethoxy, 1-imidazolyl or C$_1$-C$_4$-haloalkoxy such as trichloromethoxy. L$^2$ is halogen, in particular chlorine, trichloromethoxy, 1-imidazolyl, O—C(O)—Cl or C$_1$-C$_4$-alkoxy, in particular methoxy or ethoxy. Examples of suitable compounds of the formula C(O)L$^1$L$^2$ are phosgene, diphosgene, triphosgene, methyl or ethyl chloroformate, carbonyldiimidazole, dimethylcarbonate and diethylcarbonate. The reaction of XIII with C(O)L$^1$L$^2$ can be achieved by analogy to the processes described in WO 2007/43677.

The reactions described herein are carried out in reaction vessels customary for such reactions, the reaction being configurable continuously, semicontinuously or batchwise.

EXAMPLES

The compounds can be characterized e.g. by coupled High Performance Liquid Chromatography/mass spectrometry (HPLC/MS), by $^1$H-NMR and/or by their melting points. The following analytical procedures were employed:

Analytical HPLC column: RP-18 column Chromolith Speed ROD from Merck KgaA, Germany). Elution: acetonitrile+0.1% trifluoroacetic acid (TFA)/water+0.1% trifluoroacetic acid (TFA) in a ratio of from 5:95 to 95:5 in 5 minutes at 40° C. Analytical UPLC column: Phenomenex Kinetex 1.7 µm XB-C18 100 A; 50×2.1 mm; mobile phase: A: water+0.1% trifluoroacetic acid (TFA); B: acetonitrile+0.1% TFA; gradient: 5-100% B in 1.50 minutes; 100% B 0.20 min; flow: 0.8-1.0 mL/min in 1.50 minutes at 60° C.

MS-method: ESI positive $^1$H-NMR. The signals are characterized by chemical shift (ppm) vs. tetramethylsilane, by their multiplicity and by their integral (relative number of hydrogen atoms given). The following abbreviations are used to characterize the multiplicity of the signals: m=multiplett, q=quartett, t=triplett, d=doublet and s=singulett.

Starting Materials 6,8-dichloro-1H-benzo[d][1,3]oxazine-2,4-dione and 6-chloro-8-methyl-1H-3,1-benzoxazine-2,4-dione were prepared according to WO 2007/43677

S,S-Diisopropyl-5-aminosulfonium 2,4,6-trimethylphenylsulfonat was prepared according to Y. Tamura et al, *Tetrahedron*, 1975, 31, 3035-3040.

Example P.1

S,S-Dimethyl sulfinium sulfate (Compound IV-1 with R$^1$=R$^2$=methyl, A$^-$=½ SO$_4^{2-}$)

To a solution of sodium methylate (15.76 g of a 30% solution in methanol, 87.54 mmol, 1.100 equiv.) in methanol (60 mL) was added dimethyl sulphide (5.44 g, 6.40 mL, 87.6 mmol, 1.10 equiv.) at −5-0° C. To this mixture was added a pre-cooled solution (−20° C.) of hydroxylamine-O-sulfonic acid (9.00 g, 79.6 mmol) in methanol (60 mL) and the internal temperature was maintained at −5-0° C. After stirring at room temperature over night, all solids were removed by filtration. The filtrate was concentrated in vacuo and the residue was triturated with acetonitrile (50 mL) to yield the title compound (7.88 g, 39%).

The following compounds were prepared by analogy to example P.1:

S,S-diethyl sulfinium sulfate (Compound IV-1 with R$^1$=R$^2$=ethyl, A$^-$=½ SO$_4^{2-}$), S-ethyl-5-isopropyl sulfinium sulfate (Compound IV-1 with R$^1$=ethyl, R$^2$=isopropyl, A$^-$=½ SO$_4^{2-}$), S,S-diisopropyl sulfinium sulfate (Compound IV-1 with R$^1$=R$^2$=2-propyl, A$^-$=½ SO$_4^{2-}$), tetrahydro-λ$^4$-thiophen-1-ylamin mesitylsulfonate (Compound IV-1 with R$^1$-R$^2$=1,4-butandiyl, A$^-$=2,4,6-trimethylphenylsulfonate) was prepared according to Y. Tamura et al, *Tetrahedron*, 1975, 31, 3035-3040.

tetrahydro-λ$^4$-thiophen-1-ylamin sulfate (Compound IV-1 with R$^1$-R$^2$=1,4-butandiyl, A$^-$=½ SO$_4^{2-}$), λ$^4$-1,3-dithiolan-1-ylamin sulfate (Compound IV-1 with R$^1$-R$^2$=2-thiabutan-1,4-diyl, A$^-$=½ SO$_4^{2-}$), λ$^4$-thian-1-ylamin sulfate (Compound IV-1 with R$^1$-R$^2$=pentan-1,5-diyl, A$^-$=½ SO$_4^{2-}$), S,S-bis(cyclopropylmethyl) sulfinium sulfate (Compound IV-1 with R$^1$=R$^2$=cyclopropylmethyl, A$^-$=½ SO$_4^{2-}$), S,S-bis(2-cyclopropylethyl) sulfinium sulfate (Compound IV-1 with R$^1$=R$^2$=2-cyclopropylethyl, A$^-$=½ SO$_4^{2-}$), S,S-bis(cyclobutylmethyl) sulfinium sulfate (Compound IV-1 with R$^1$=R$^2$=cyclobutylmethyl, A$^-$=½ SO$_4^{2-}$), S,S-bis(cyclopentylmethyl) sulfinium sulfate (Compound IV-1 with R$^1$=R$^2$=cyclopentylmethyl, A$^-$=½ SO$_4^{2-}$), S-cyclopropylmethyl-5-ethyl sulfinium sulfate (Compound IV-1 with R$^1$=ethyl, R$^2$=cyclopropylmethyl, A$^-$=½ SO$_4^{2-}$), S-(2-cyclopropylethyl)-S-ethyl sulfinium sulfate (Compound IV-1 with R$^1$=ethyl, R$^2$=2-cyclopropylethyl, A$^-$=½ SO$_4^{2-}$), S-(2-cyclopropylethyl)-S-isopropyl sulfinium sulfate (Compound IV-1 with R$^1$=2-propyl, R$^2$=2-cyclopropylethyl, A$^-$=½ SO$_4^{2-}$), S-(1-cyclopropylethyl)-S-isopropyl sulfinium sulfate (Compound IV-1 with R$^1$=2-propyl, R$^2$=1-cyclopropylethyl, A$^-$=½ SO$_4^{2-}$), S-cyclobutylmethyl-5-ethyl sulfinium sulfate (Compound IV-1 with $R^1$=ethyl, $R^2$=cyclobutylmethyl, $A^-$=½ $SO_4^{2-}$),
S-cyclopentylmethyl-5-ethyl sulfinium sulfate (Compound IV-1 with $R^1$=ethyl, $R^2$=cyclopentylmethyl, $A^-$=½ $SO_4^{2-}$),
S-cyclopropylmethyl-5-isopropyl sulfinium sulfate (Compound IV-1 with $R^1$=2-propyl, $R^2$=cyclopropylmethyl, $A^-$=½ $SO_4^{2-}$),
S-cyclobutylmethyl-5-isopropyl sulfinium sulfate (Compound IV-1 with $R^1$=2-propyl, $R^2$=cyclobutylmethyl, $A^-$=½ $SO_4^{2-}$),
S-cyclopentylmethyl-5-isopropyl sulfinium sulfate (Compound IV-1 with $R^1$=2-propyl, $R^2$=cyclopentylmethyl, $A^-$=½ $SO_4^{2-}$),
S,S-di-n-propyl sulfinium sulfate (Compound IV-1 with $R^1$=$R^2$=n-propyl, $A^-$=½ $SO_4^{2-}$),
S-vinyl-5-ethyl sulfinium sulfate (Compound IV-1 with $R^1$=ethyl, $R^2$=vinyl, $A^-$=½ $SO_4^{2-}$),
S,S-di-n-butyl sulfinium sulfate (Compound IV-1 with $R^1$=$R^2$=n-butyl, $A^-$=½ $SO_4^{2-}$),
S,S-di-n-pentyl sulfinium sulfate (Compound IV-1 with $R^1$=$R^2$=n-pentyl, $A^-$=½ $SO_4^{2-}$),
S,S-di-n-hexyl sulfinium sulfate (Compound IV-1 with $R^1$=$R^2$=n-hexyl, $A^-$=½ $SO_4^{2-}$),
S,S-bis(2-ethylhexyl) sulfinium sulfate (Compound IV-1 with $R^1$=$R^2$=2-ethylhexyl, $A^-$=½ $SO_4^{2-}$),
S,S-bis(3-methyl-2-butyl) sulfinium sulfate (Compound IV-1 with $R^1$=$R^2$=3-methyl-2-butyl, $A^-$=½ $SO_4^{2-}$),
S,S-bis(3-methyl-1-butyl) sulfinium sulfate (Compound IV-1 with $R^1$=$R^2$=3-methyl-1-butyl, $A^-$=½ $SO_4^{2-}$),
S,S-bis(2-methylpropyl) sulfinium sulfate (Compound IV-1 with $R^1$=$R^2$=2-methylpropyl, $A^-$=½ $SO_4^{2-}$),
S-isopropyl-5-methyl sulfinium sulfate (Compound IV-1 with $R^1$=methyl, $R^2$=isopropyl $A^-$=½ $SO_4^{2-}$),
S-2-butyl-5-methyl sulfinium sulfate (Compound IV-1 with $R^1$=methyl, $R^2$=2-butyl, $A^-$=½ $SO_4^{2-}$),
S-3-Methyl-2-butyl-5-methyl sulfinium sulfate (Compound IV-1 with $R^1$=methyl, $R^2$=3-Methyl-2-butyl $A^-$=½ $SO_4^{2-}$),
S-3-Methyl-2-butyl-5-ethyl sulfinium sulfate (Compound IV-1 with $R^1$=ethyl, $R^2$=3-Methyl-2-butyl $A^-$=½ $SO_4^{2-}$),
S-3-Methyl-2-butyl-5-isopropyl sulfinium sulfate (Compound IV-1 with $R^1$=2-propyl, $R^2$=3-Methyl-2-butyl $A^-$=½ $SO_4^{2-}$),
S,S-bis(2-hydroxyethyl) sulfinium sulfate (Compound IV-1 with $R^1$=$R^2$=2-hydroxyethyl, $A^-$=½ $SO_4^{2-}$),
S-(4-Fluorophenyl)-S-methyl sulfinium sulfate (Compound IV-1 with $R^1$=methyl, $R^2$=4-fluorophenyl, $A^-$=½ $SO_4^{2-}$),
S-n-pentyl-S-2-hydroxyethyl sulfinium sulfate (Compound IV-1 with $R^1$=n-pentyl, $R^2$=2-hydroxyethyl, $A^-$=½ $SO_4^{2-}$),
S-ethyl-5-cyclopropyl sulfinium sulfate (Compound IV-1 with $R^1$=ethyl, $R^2$=cyclopropyl, $A^-$=½ $SO_4^{2-}$),
S-2-propyl-5-cyclopropyl sulfinium sulfate (Compound IV-1 with $R^1$=2-propyl, $R^2$=cyclopropyl, $A^-$=½ $SO_4^{2-}$),
S-methyl-5-ethyl sulfinium sulfate (Compound IV-1 with $R^1$=methyl, $R^2$=ethyl, $A^-$=½ $SO_4^{2-}$),
S-methyl-S-n-propyl sulfinium sulfate (Compound IV-1 with $R^1$=methyl, $R^2$=n-propyl, $A^-$=½ $SO_4^{2-}$),
S-(2-chloroethyl)-S-ethyl sulfinium sulfate (Compound IV-1 with $R^1$=2-chloroethyl, $R^2$=ethyl, $A^-$=½ $SO_4^{2-}$).

Example P.2

8-Bromo-6-chloro-1H-benzo[d][1,3]oxazine-2,4-dione

To a solution of 2-amino-3-bromo-5-chlorobenzoic acid (10.0 g, 39.9 mmol) in dioxane (170 mL) was added phosgene (20% in toluene, 42.0 mL, 79.9 mmol) over a period of 15 mins. The reaction was stirred at ambient temperature for 48 h and then concentrated in vacuo. The resulting solid was crushed and further dried in vacuo to yield the desired product (12.6 g, 114%) which was used in the subsequent step without further purification.

The following compounds were prepared by analogy to example P.2:
6,8-dichloro-1H-benzo[d][1,3]oxazine-2,4-dione
6,8-dibromo-1H-benzo[d][1,3]oxazine-2,4-dione The following compounds can be prepared by analogy to example P.2:
6-chloro-8-methyl-1H-benzo[d][1,3]oxazine-2,4-dione
6-bromo-8-methyl-1H-benzo[d][1,3]oxazine-2,4-dione
6-cyano-8-methyl-1H-benzo[d][1,3]oxazine-2,4-dione
6-chloro-8-trifluoromethyl-1H-benzo[d][1,3]oxazine-2,4-dione
8-chloro-6-trifluoromethyl-1H-benzo[d][1,3]oxazine-2,4-dione
6-bromo-8-trifluoromethyl-1H-benzo[d][1,3]oxazine-2,4-dione
8-bromo-6-trifluoromethyl-1H-benzo[d][1,3]oxazine-2,4-dione
8-chloro-6-cyano-1H-benzo[d][1,3]oxazine-2,4-dione
6-Bromo-8-chloro-1H-benzo[d][1,3]oxazine-2,4-dione,
8-Bromo-6-chloro-1H-benzo[d][1,3]oxazine-2,4-dione,
6-chloro-8-methoxy-1H-benzo[d][1,3]oxazine-2,4-dione,
6-chloro-8-cyclopropyl-1H-benzo[d][1,3]oxazine-2,4-dione,
6-chloro-8-ethyl-1H-benzo[d][1,3]oxazine-2,4-dione,
6-difluoromethoxy-8-methyl-1H-benzo[d][1,3]oxazine-2,4-dione,
6-cyano-8-methoxy-1H-benzo[d][1,3]oxazine-2,4-dione,
6-fluoro-8-methyl-1H-benzo[d][1,3]oxazine-2,4-dione,
6-iodo-8-methyl-1H-benzo[d][1,3]oxazine-2,4-dione,
6-nitro-8-methyl-1H-benzo[d][1,3]oxazine-2,4-dione,
6-(5-chloro-2-thienyl)-8-methyl-1H-benzo[d][1,3]oxazine-2,4-dione,
6-(3-pyrazol-1H-yl)-8-methyl-1H-benzo[d][1,3]oxazine-2,4-dione,
6-(3-isoxazolyl)-8-methyl-1H-benzo[d][1,3]oxazine-2,4-dione,
6-(hydroxyiminomethyl)-8-methyl-1H-benzo[d][1,3]oxazine-2,4-dione,
6-(methoxyiminomethyl)-8-methyl-1H-benzo[d][1,3]oxazine-2,4-dione,
6-(dimethylhydrazonomethyl)-8-methyl-1H-benzo[d][1,3]oxazine-2,4-dione and
6-(2,2,2-trifluoroethylhydrazonomethyl)-8-methyl-1H-benzo[d][1,3]oxazine-2,4-dione.

Example P.3

1-(3-chloro-2-pyridyl)-3-trifluoromethyl-1H-pyrazol a) 2.71 kg of 1,1,1-trifluoro-4-methoxy-but-3-en-2-on, 2.44 kg of ethanol and 3.10 kg of water were charged into a reaction vessel. 20 ml of concentrated hydrochloric acid and 0.80 kg of hydrazine hydrate were successively added and the mixture was heated to reflux for 4 h. The mixtures was allowed to cool and neutralized by addition of 10% aqueous NaOH to about pH 4-5. Then the mixture was evaporated. Toluene was added and the mixture was again evaporated to yield 2 kg of raw 3-trifluoromethyl-pyrazole with a purity of >85%.

1.72 kg (10.75 mol) of the raw 3-trifluoromethylpyrazole obtained in step a), 1.75 kg (11.83 mol) of 2,3-dichloropyridine and 4.73 kg of dimethyl formamide were charged to a reaction vessel. 2.97 kg (21.50 mol) of potassium carbonate were added, the mixture was heated to 120° C. with stirring and kept at 120-125° C. for further 3 h. The reaction mixtures was cooled to 25° C. and poured into 20 l of water. The thus obtained mixture was extracted twice with 5 L of tert.-butylmethyl ether. The combined organic phases were washed with 4 l of water and then evaporated to dryness. Toluene was added and the mixture was again evaporated to dryness. Thereby, the 2.7 kg of the title compound was obtained (purity>75% as determined by GC; yield 81.5%). The product can be purified by distillation.

Characterization by $^1$H-NMR (400 MHz, CDCl$_3$): δ [delta]=6.73 (d, 1H), 7.38 (d, 1H), 7.95 (m, 1H), 8.14 (m, 1H), 8.46 (m, 1H).

Preparation of the Compounds of Formula (VII)

Example P.4

2-amino-5-chloro-N-(dimethyl-λ$^4$-sulfanylidene)-3-methyl-benzamide

To a solution of 6-chloro-8-methyl-1H-3,1-benzoxazine-2,4-dione (3.00 g, 12.8 mmol) in dichloromethane (40 mL) was added dimethyl sulfinium sulfate (2.25 g, 8.93 mmol, 0.70 equiv.) and potassium tert-butylate (1.58 g, 14.0 mmol, 1.10 equiv.) at room temperature. The mixture was stirred for 1.5 h, upon which water was added and the layers were separated. The aqueous layer was extracted with dichloromethane, combined organic layers were dried over sodium sulphate and concentrated in vacuo. The residue was purified by flash-chromatography on silica gel to yield the title compound (2.63 g, 84%).

Characterization by HPLC-MS: 1.855 min, M=245.00.

Example P.5

2-amino-5-chloro-N-(bis-2-propyl-λ$_4$-sulfanylidene)-3-methyl-benzamide

To a solution of 6-chloro-8-methyl-1H-3,1-benzoxazine-2,4-dione (3.00 g, 12.8 mmol) in dichloromethane (40 mL) was added bis-2-propyl sulfinium sulfate (3.76 g, 8.93 mmol, 0.70 equiv.) and potassium tert-butylate (1.58 g, 14.0 mmol, 1.10 equiv.) at room temperature. The mixture was stirred for 1.5 h, upon which water was added and the layers were separated. The aqueous layer was extracted with dichloromethane, combined organic layers were dried over sodium sulphate and concentrated in vacuo. The residue was purified by flash-chromatography on silica gel to yield the title compound (2.89 g, 69%).

Characterization by UPLC-MS: 1.044 min, M=329.1;
Characterization by $^1$H-NMR (400 MHz, DMSO-d$_6$): δ [delta]=1.04 (m, 12H), 2.06 (s, 3H), 2.96 (m, 2H), 3.01 (m, 2H), 6.62 (br. s, 2H), 7.03 (s, 1H), 7.72 (s, 1H).

Example P.6

2-amino-5-chloro-N-(bis-2-methylpropyl-λ$^4$-sulfanylidene)-3-methyl-benzamide

To a solution of 6-chloro-8-methyl-1H-3,1-benzoxazine-2,4-dione (12.17 g, 0.06 mol) in anhydrous DMSO (100 mL) was added bis-2-methylpropyl sulfinium sulfate (14.56 g, 0.04 mol, 0.70 equiv.) and triethyl amine (9.19 mL, 6.67 g, 0.07 mol, 1.15 equiv.) at room temperature. The mixture was stirred for 4.5 h, and then added dropwise to ice-water. The mixture was extracted with dichloromethane and the combined organic layers were dried over sodium sulphate and concentrated in vacuo. The residue was triturated with ether to yield the title compound (8.3 g, 46%).

Characterization by $^1$H-NMR (400 MHz, DMSO-d$_6$): δ [delta]=1.04 (m, 12H), 2.06 (s, 3H), 2.96 (m, 2H), 3.01 (m, 2H), 6.62 (br. s, 2H), 7.03 (s, 1H), 7.72 (s, 1H).

Example P.7

2-amino-5-chloro-N-(diethyl-λ$^4$-sulfanylidene)-3-methyl-benzamide

To a solution of 6-chloro-8-methyl-1H-3,1-benzoxazine-2,4-dione (2 g, 0.01 mol) in anhydrous propylene carbonate (30 mL) was added bis-2-ethyl sulfinium sulfate (2.04 g, 0.01 mol, 0.70 equiv.) and triethyl amine (1.38 mL, 1.0 g g, 0.01 mol, 1.05 equiv.) at room temperature. The mixture was stirred for 4.5 h, and then added dropwise to ice-water. The mixture was extracted with dichloromethane and the combined organic layers were dried over sodium sulphate and concentrated in vacuo. The residue was triturated with ether to yield the title compound (1.43 g, 55%).

Characterization by $^1$H-NMR (400 MHz, CDCl$_3$): δ [delta]=1.39 (t, 6H), 2.13 (s, 3H), 3.02 (q, 4H), 5.95 (br. S, 2H), 7.01 (s, 1H), 7.98 (s, 1H).

Example P.8

2-amino-3,5-dichloro-N-(bis-2-methylpropyl-λ$^4$-sulfanylidene)-benzamide

The title compound was prepared by analogy to the method of example P.7
Yield: 60%
Characterization by $^1$H-NMR (400 MHz, DMSO-d$_6$): δ [delta]=1.23 (d, 6H), 1.38 (d, 6H), 3.42 (m, 2H), 7.02 (br. s, 2H), 7.41 (s, 1H), 7.95 (s, 1H).

By the methods described in examples P.4 to P.8 the compounds of formula VII with t=0, R$^5$=H, summarized in the following table C.1 were prepared:

TABLE C.1 compounds of formula VII with t = 0 and R$^5$ = H

| Cpd. | R$^6$ | R$^7$ | R$^3$ | R$^4$ | HPLC/MS (Method) |
|---|---|---|---|---|---|
| S.3 | C$_2$H$_5$ | C$_2$H$_5$ | CH$_3$ | Cl | 2.159 min, m/z = 273.0 (A) |
| S.4 | CH$_2$CH(CH$_3$)$_2$ | CH$_2$CH(CH$_3$)$_2$ | Cl | Cl | |
| S.5 | CH(CH$_3$)$_2$ | CH(CH$_3$)$_2$ | Cl | Cl | 3.346 min, m/z = 321.05 (A) |
| S.6 | C$_2$H$_5$ | C$_2$H$_5$ | Cl | Cl | 2.821 min, m/z = 292.9 (A) |
| S.7 | CH$_2$—c-Pr | CH$_2$—c-Pr | CH$_3$ | Cl | 1.191 min, m/z = 325.5 (B) |
| S.8 | CH$_2$—c-Pr | CH$_2$—c-Pr | Cl | Cl | 1.391 min, m/z = 320.8 (B) |
| S.9 | CH$_2$—c-Pr | C$_2$H$_5$ | CH$_3$ | Cl | 1.197 min, m/z = 299.1 (B) |
| S.10 | CH$_2$—c-Pr | CH(CH$_3$)$_2$ | Cl | Cl | 3.200 min, m/z = 333.0 (A) |

TABLE C.1-continued compounds of formula VII with t = 0 and $R^5$ = H

| Cpd. | $R^6$ | $R^7$ | $R^3$ | $R^4$ | HPLC/MS (Method) |
|---|---|---|---|---|---|
| S.11 | $CH_2$—c-Pr | $CH(CH_3)_2$ | $CH_3$ | Cl | 2.433 min, m/z = 313.0 (A) |
| S.12 | $C_2H_5$ | $C_2H_5$ | $CF_3$ | Cl | 3.218 min, m/z = 327.00 (A) |
| S.13 | $C_2H_5$ | $C_2H_5$ | $CF_3$ | Br | 3.291 min, m/z = 372.90 (A) |
| S.14 | $C_2H_5$ | $C_2H_5$ | Br | Cl | 2.980 min, m/z = 338.90 (A) |
| S.15 | $C_2H_5$ | $C_2H_5$ | Cl | Br | 2.970 min, m/z = 338.90 (A) |
| S.16 | $CH(CH_3)_2$ | $CH(CH_3)_2$ | $CF_3$ | Cl | 3.604 min, m/z = 355.05 (A) |
| S.17 | $CH(CH_3)_2$ | $CH(CH_3)_2$ | $CF_3$ | Br | 3.677 min, m/z = 400.95 (A) |
| S.18 | $CH(CH_3)_2$ | $CH(CH_3)_2$ | Br | Cl | 3.390 min, m/z = 366.95 (A) |
| S.19 | $CH(CH_3)_2$ | $CH(CH_3)_2$ | Cl | Br | 3.381 min, m/z = 366.95 (A) |
| S.20 | $CH(CH_3)_2$ | $CH(CH_3)_2$ | Br | Br | 3.409 min, m/z = 410.90 (A) |
| S.21 | $CH_2CH_2CH_3$ | $CH_2CH_2CH_3$ | $CH_3$ | Cl | 1.046 min, m/z = 301.1 (B) |
| S.22 | $CH_2CH_2CH_3$ | $CH_2CH_2CH_3$ | Cl | Cl | 3.441 min, m/z = 320.95 (A) |
| S.23 | $C_2H_5$ | $C_2H_5$ | Br | Br | 1.102 min, m/z = 383.0 (B) |
| S.24 | $CH(CH_3)_2$ | $CH(CH_3)_2$ | $CH_3$ | Cl | 2.510 min, m/z = 301.05 (A) |

$CH_2$—c-Pr = $CH_2$—cyclopropyl

The following compounds were/can be prepared by analogy to examples P.4 to P.8:
2-amino-5-chloro-N-(tetrahydro-$\lambda^4$-thiophenylidene)-3-methyl-benzamide,
2-amino-5-chloro-N-(diethyl-$\lambda^4$-sulfanylidene)-3-methyl-benzamide,
2-amino-5-bromo-N-(bis-2-propyl-$\lambda^4$-sulfanylidene)-3-methyl-benzamide,
2-amino-5-bromo-N-(dimethyl-$\lambda^4$-sulfanylidene)-3-methyl-benzamide,
2-amino-5-bromo-N-(diethyl-$\lambda^4$-sulfanylidene)-3-methyl-benzamide,
2-amino-5-bromo-N-(tetrahydro-$\lambda^4$-thiophenylidene)-3-methyl-benzamide,
2-amino-5-cyano-N-(bis-2-propyl-$\lambda^4$-sulfanylidene)-3-methyl-benzamide,
2-amino-5-cyano-N-(dimethyl-$\lambda^4$-sulfanylidene)-3-methyl-benzamide,
2-amino-5-cyano-N-(diethyl-$\lambda^4$-sulfanylidene)-3-methyl-benzamide,
2-amino-5-cyano-N-(tetrahydro-$\lambda^4$-thiophenylidene)-3-methyl-benzamide,
2-amino-3,5-dichloro-N-(bis-2-propyl-$\lambda^4$-sulfanylidene)-benzamide,
2-amino-3,5-dichloro-N-(dimethyl-$\lambda^4$-sulfanylidene)-benzamide,
2-amino-3,5-dichloro-N-(diethyl-$\lambda^4$-sulfanylidene)-benzamide,
2-amino-3,5-dichloro-N-(tetrahydro-$\lambda^4$-thiophenylidene)-benzamide,
2-amino-3,5-dibromo-N-(bis-2-propyl-$\lambda^4$-sulfanylidene)-benzamide,
2-amino-3,5-dibromo-N-(dimethyl-$\lambda^4$-sulfanylidene)-benzamide,
2-amino-3,5-dibromo-N-(diethyl-$\lambda^4$-sulfanylidene)-benzamide,
2-amino-3,5-dibromo-N-(tetrahydro-$\lambda^4$-thiophenylidene)-benzamide,
2-amino-5-bromo-N-(bis-2-propyl-$\lambda^4$-sulfanylidene)-3-trifluoromethyl-benzamide,
2-amino-5-bromo-N-(dimethyl-$\lambda^4$-sulfanylidene)-3-trifluoromethyl-benzamide,
2-amino-5-bromo-N-(diethyl-$\lambda^4$-sulfanylidene)-3-trifluoromethyl-benzamide,
2-amino-5-bromo-N-(tetrahydro-$\lambda^4$-thiophenylidene)-3-trifluoromethyl-benzamide,
2-amino-3-chloro-5-cyano-N-(bis-2-propyl-$\lambda^4$-sulfanylidene)-benzamide,
2-amino-3-chloro-5-cyano-N-(dimethyl-$\lambda^4$-sulfanylidene)-benzamide,
2-amino-3-chloro-5-cyano-N-(diethyl-$\lambda^4$-sulfanylidene)-benzamide,
2-amino-3-chloro-5-cyano-N-(tetrahydro-$\lambda^4$-thiophenylidene)-benzamide,
2-amino-3-bromo-N-(bis-2-propyl-$\lambda^4$-sulfanylidene)-5-trifluoromethyl-benzamide,
2-amino-5-chloro-N-(bis-2-propyl-$\lambda^4$-sulfanylidene)-3-trifluoromethyl-benzamide,
2-amino-5-chloro-N-(dimethyl-$\lambda^4$-sulfanylidene)-3-trifluoromethyl-benzamide,
2-amino-5-chloro-N-(diethyl-$\lambda^4$-sulfanylidene)-3-trifluoromethyl-benzamide,
2-amino-5-chloro-N-(tetrahydro-$\lambda^4$-thiophenylidene)-3-trifluoromethyl-benzamide,
2-amino-3-bromo-N-(dimethyl-$\lambda^4$-sulfanylidene)-5-trifluoromethyl-benzamide,
2-amino-3-bromo-N-(diethyl-$\lambda^4$-sulfanylidene)-5-trifluoromethyl-benzamide,
2-amino-3-bromo-N-(tetrahydro-$\lambda^4$-thiophenylidene)-5-trifluoromethyl-benzamide,
2-amino-3-chloro-N-(bis-2-propyl-$\lambda^4$-sulfanylidene)-5-trifluoromethyl-benzamide,
2-amino-3-chloro-N-(dimethyl-$\lambda^4$-sulfanylidene)-5-trifluoromethyl-benzamide,
2-amino-3-chloro-N-(diethyl-$\lambda^4$-sulfanylidene)-5-trifluoromethyl-benzamide,
2-amino-3-chloro-N-(tetrahydro-$\lambda^4$-thiophenylidene)-5-trifluoromethyl-benzamide,
2-amino-3-bromo-N-(diethyl-$\lambda^4$-sulfanylidene)-5-chloro-benzamide,
2-amino-3-bromo-N-(bis-2-propyl-$\lambda^4$-sulfanylidene)-5-chloro-benzamide,
2-amino-3,5-dichloro-N-(ethyl-2-propyl-$\lambda^4$-sulfanylidene)-benzamide,
2-amino-5-chloro-N-(ethyl-2-propyl-$\lambda^4$-sulfanylidene)-3-methyl-benzamide,
2-amino-5-chloro-N-(bis-2-methylpropyl-$\lambda^4$-sulfanylidene)-3-methyl-benzamide,
2-amino-3,5-dichloro-N-(bis-2-methylpropyl-$\lambda^4$-sulfanylidene)-benzamide,
2-amino-3,5-dichloro-N-(bis-cyclopropylmethyl-$\lambda^4$-sulfanylidene)-benzamide.

Preparation Examples

Preparation of the Compounds of Formula (I-A)

Example A.1

2-(3-Chloropyridin-2-yl)-5-trifluoromethyl-2H-pyrazole-3-carboxylate

In a reaction vessel equipped with a thermometer, septum, nitrogen inlet and stirring bar, 2.0 g (8.1 mmol) of 1-(3-chloro-2-pyridyl)-3-trifloromethyl-1H-pyrazole were dissolved in 15 ml of dry dimethoxyethane. By means of a syringe, 8.08 ml of a 2 M solution (16.1 mmol, 2.0 equiv.) of isopropyl magnesium chloride in tetrahydrofuran were added dropwise with stirring, while cooling the vessel with an ice bath and keeping the internal temperature at about 5° C. The mixture was stirred for further 3 hours at 5° C. Then the ice-bath was removed and carbon dioxide was bubbled through mixture causing an increase of the temperature up to 28° C. After 10 minutes, the exothermic reaction has ceased, and the mixture was cooled and all volatiles were removed by evaporation. The residue containing the title compound (5.61 g, purity>71%) as a mixture with chloromagnesium 2-methyl propionate. This mixture was used as such in the next step without further purification.

Preparation of the compounds of formula (I)

Examples S.1 to S.7

Example S.1

2-(3-Chloropyridin-2-yl)-5-trifluoromethyl-2H-pyrazole-3-carbonyl chloride

In a reaction vessel equipped with a thermometer, septum, nitrogen inlet and stirring bar, 10.0 g (40.4 mmol) of 1-(3-chloro-2-pyridyl)-3-trifloromethyl-1H-pyrazole were dissolved in 50 ml of dry dimethoxyethane. By means of a syringe, 40.4 ml of a 2 M solution (80.8 mmol, 2.0 equiv.) of isopropyl magnesium chloride in tetrahydrofuran were added dropwise with stirring, while cooling the vessel with an ice bath and keeping the internal temperature at about 5° C. The mixture was stirred for further 2 hours at 5° C. Then the ice-bath was removed and carbon dioxide was bubbled through mixture causing an increase of the temperature up to 28° C. After 10 minutes, the exothermic reaction has ceased, and, the mixture was cooled and all volatiles were removed by evaporation. The residue containing the carboxylate compound I-A was taken up in 50 mL of dichloromethane and one drop of dry DMF was added. To this mixture, 14.41 g (121.2 mmol, 3.0 equiv.) of thionyl chloride were added and heated to reflux for 3 hours. After cooling, the resulting precipitate was removed by filtration and the mother liquid was concentrated in vacuum to obtain 13.0 g of the title compound (purity>85%, yield 100%) which was used in the next step without further purification.

$^1$H-NMR (400 MHz, CDCl$_3$): δ [delta]=7.43-7.54 (m, 2H), 7.93 (d, 1H), 8.52 (m, 1H).

Example S.1a 2-(3-Chloropyridin-2-yl)-5-trifluoromethyl-2H-pyrazole-3-carbonyl chloride In a reaction vessel equipped with a thermometer, septum, nitrogen inlet and stirring bar, 5.61 g of 2-(3-chloropyridin-2-yl)-5-trifluoromethyl-2H-pyrazole-3-carboxylate as obtained in example A.1 were dissolved in 50 mL of dichloromethane and one drop of dry DMF was added. To this mixture, 3.08 g (24.3 mmol, 3.0 equiv.) of oxalyl chloride were added at room temperature and stirred over night. After concentration in vacuum the resulting residue was taken up in dichloromethane and the resulting precipitate was removed by filtration. The obtained mother liquid was concentrated in vacuum to obtain 3.05 g of the title compound (purity>82%, yield 100%) which was used in the next step without further purification.

The $^1$H-NMR data (400 MHz, CDCl$_3$) correspond to the data as obtained in Example S.1.

Example S.1b 2-(3-Chloropyridin-2-yl)-5-trifluoromethyl-2H-pyrazole-3-carboxylic acid In a reaction vessel equipped with a thermometer, septum, nitrogen inlet and stirring bar, 5.61 g of 2-(3-chloropyridin-2-yl)-5-trifluoromethyl-2H-pyrazole-3-carboxylate as obtained in example A.1 were taken up in 50 mL of water and concentrated aqueous hydrochloric acid was added to adjust the pH to 2. The mixture was extracted with ethyl acetate and combined organic layers were washed with brine, dried over sodium sulphate and concentrated in vacuum to obtain the title compound (2.3 g, 98%). Characterization by HPLC-MS: R=3.295 min; m/z=291.95

Example S.1c 2-(3-Chloropyridin-2-yl)-5-trifluoromethyl-2H-pyrazole-3-carbonyl chloride In a reaction vessel equipped with a thermometer, septum, nitrogen inlet and stirring bar, 0.5 g (1.7 mmol) of 2-(3-chloropyridin-2-yl)-5-trifluoromethyl-2H-pyrazole-3-carboxylic acid as obtained in example S.1b were dissolved in 10 mL of dichloromethane and one drop of dry DMF was added. To this mixture, 0.65 g (5.14 mmol, 3.0 equiv.) of oxalyl chloride were added at 0° C. and stirred at room temperature over night. After concentration in vacuum the resulting residue was taken up in dichloromethane and the resulting precipitate was removed by filtration. The obtained mother liquid was concentrated in vacuum to obtain 0.58 g of the title compound (purity>91%, yield 100%) which was used in the next step without further purification. The $^1$H-NMR data (400 MHz, CDCl$_3$) correspond to the data as obtained in Example S.1.

The following compounds can be prepared by analogy to example S.1, S.1a or S.1c:

Example S.2

2-(3-Chloropyridin-2-yl)-5-bromo-2H-pyrazole-3-carbonyl chloride

Example S.3

2-(3-Trifluoromethyl-pyridin-2-yl)-5-trifluoromethyl-2H-pyrazole-3-carbonyl chloride Example S.4

2-(3-Chloropyridin-2-yl)-5-difluoromethyl-2H-pyrazole-3-carbonyl chloride

Example S.5

2-(3-Trifluoromethyl-pyridin-2-yl)-5-difluoromethyl-2H-pyrazole-3-carbonyl chloride

Example S.6

2-(3-Chloropyridin-2-yl)-5-methoxy-2H-pyrazole-3-carbonyl chloride

Example S.7

2-(3-Trifluoromethyl-pyridin-2-yl)-5-methoxy-2H-pyrazole-3-carbonyl chloride

Preparation of the Compounds of Formula (VI)

Examples 1 to 56

Example 1

2-(3-chloro-2-pyridyl)-N-[2,4-dichloro-6-[(diethyl-λ⁴-sulfanylidene)carbamoyl]phenyl]-5-(trifluoromethyl)pyrazole-3-carboxamide To a suspension of potassium carbonate (0.51 g, 3.7 mmol, 1.50 equiv) and 2-amino-3,5-dichloro-N-(diethyl-λ⁴-sulfanylidene)benzamide (0.72 g, 2.5 mmol) in dichloromethane (5 mL) was added a solution of crude 2-(3-chloro-2-pyridyl)-5-(trifluoromethyl)pyrazole-3-carbonyl chloride (1.00 g, 2.74 mmol, 1.11 equiv.) as obtained from S.1 in dichloromethane (5 mL) at room temperature. After stirring over night, all solids were filtered off. The mother liquid was washed with water, separated and dried over $Na_2SO_4$. After concentration, the resulting solids were triturated with ether to obtain the title compound (0.95 g, 68%).

Characterization by $^1H$-NMR (400 MHz, DMSO-$d_6$):

δ [delta]=1.13 (t, 6H), 2.91 (m, 2H), 3.08 (m, 2H), 7.67 (dd, 1H), 7.77 (s, 2H), 7.89 (s, 1H), 8.22 (d, 1H), 8.51 (d, 1H), 10.73 (s, 1H).

The compounds of examples 2 to 56 that are compounds of formula (VI-A) depicted in the following table, can be prepared by analogy to the methods described in example 1:

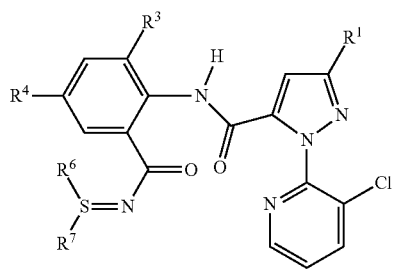

(VI-A)

Compounds VI-A are compounds of the formula VI with t=0, $R^2$=Cl and $R^5$=H.

| Ex. | $R^6$ | $R^7$ | $R^3$ | $R^4$ | $R^1$ | HPLC/MS-Log P |
|---|---|---|---|---|---|---|
| 2 | CH(CH₃)₂ | CH(CH₃)₂ | Cl | Cl | CF₃ | 3.890 min*; m/z = 596.00 |
| 3 | CH₃ | CH₃ | Cl | Cl | CF₃ | 3.372 min*; m/z = 539.95 |
| 4 | CH₂CH₂CH₂CH₂ | | Cl | Cl | CF₃ | 3.543 min*; m/z = 564.00 |
| 5 | CH₃ | CH₃ | CH₃ | Cl | CF₃ | |
| 6 | C₂H₅ | C₂H₅ | CH₃ | Cl | CF₃ | 3.599 min*; m/z = 546.05 |
| 7 | CH(CH₃)₂ | CH(CH₃)₂ | CH₃ | Cl | CF₃ | 3.704 min*; m/z = 574.00 |
| 8 | CH₂CH₂CH₂CH₂ | | CH₃ | Cl | CF₃ | 3.478 min*; m/z = 544.05 |
| 9 | C₂H₅ | C₂H₅ | Br | Cl | CF₃ | 3.633 min*; m/z = 611.85 |
| 10 | CH(CH₃)₂ | CH(CH₃)₂ | Br | Cl | CF₃ | 3.630 min*; m/z = 639.90 |
| 11 | C₂H₅ | C₂H₅ | Br | Br | CF₃ | 1.127 min**; m/z = 655.9 |
| 12 | CH(CH₃)₂ | CH(CH₃)₂ | Br | Br | CF₃ | 3.665 min*; m/z = 683.90 |
| 13 | C₂H₅ | C₂H₅ | CF₃ | Cl | CF₃ | 1.231 min**; m/z = 600.0 |
| 14 | CH(CH₃)₂ | CH(CH₃)₂ | CF₃ | Cl | CF₃ | 1.169 min**; m/z = 628.1 |
| 15 | C₂H₅ | C₂H₅ | CF₃ | Br | CF₃ | 1.248 min**; m/z = 645.9 |
| 16 | CH(CH₃)₂ | CH(CH₃)₂ | CF₃ | Br | CF₃ | 1.308 min**; m/z = 673.9 |
| 17 | C₂H₅ | C₂H₅ | Br | CF₃ | CF₃ | 1.301 min**; m/z = 646.1 |
| 18 | CH(CH₃)₂ | CH(CH₃)₂ | Br | CF₃ | CF₃ | 1.350 min**; m/z = 673.9 |
| 19 | C₂H₅ | C₂H₅ | Cl | CF₃ | CF₃ | 1.284 min**; m/z = 673.9 |
| 20 | CH(CH₃)₂ | CH(CH₃)₂ | Cl | CF₃ | CF₃ | 1.358 min**; m/z = 600.1 |
| 21 | C₂H₅ | C₂H₅ | Cl | CN | CF₃ | 1.171 min**; m/z = 557.3 |
| 22 | CH(CH₃)₂ | CH(CH₃)₂ | Cl | CN | CF₃ | 1.262 min**; m/z = 585.3 |
| 23 | C₂H₅ | C₂H₅ | CH₃ | CN | CF₃ | 1.179 min**; m/z = 537.3 |
| 24 | CH(CH₃)₂ | CH(CH₃)₂ | CH₃ | CN | CF₃ | 1.253 min**; m/z = 565.3 |
| 25 | CH₂CH₂CH₂CH₂ | | CH₃ | Cl | Br | 3.277 min*; m/z = 556.0 |
| 26 | CH₃ | CH₃ | CH₃ | Cl | Br | 3.067 min*; m/z = 529.9 |
| 27 | C₂H₅ | C₂H₅ | CH₃ | Cl | Br | 3.309 min*; m/z = 557.9 |
| 28 | CH(CH₃)₂ | CH(CH₃)₂ | CH₃ | Cl | Br | Log P: 2.9 [pH = 10.0] |
| 29 | CH₂CH₂CH₂CH₂ | | Cl | Cl | Br | 3.184 min*; m/z = 575.8 |
| 30 | CH₃ | CH₃ | Cl | Cl | Br | 3.015 min*; m/z = 549.8 |
| 31 | C₂H₅ | C₂H₅ | Cl | Cl | Br | |
| 32 | CH(CH₃)₂ | CH(CH₃)₂ | Cl | Cl | Br | 3.538 min*; m/z = 605.8 |
| 33 | CH₂CH₂CH₂CH₂ | | CH₃ | Cl | CHF₂ | |
| 34 | CH₃ | CH₃ | CH₃ | Cl | CHF₂ | 1.060 min**; m/z = 500.2 |
| 35 | C₂H₅ | C₂H₅ | CH₃ | Cl | CHF₂ | 1.134 min**; m/z = 528.2 |
| 36 | CH(CH₃)₂ | CH(CH₃)₂ | CH₃ | Cl | CHF₂ | 1.225 min**; m/z = 556.3 |
| 37 | CH₂CH₂CH₂CH₂ | | Cl | Cl | CHF₂ | |
| 38 | CH₃ | CH₃ | Cl | Cl | CHF₂ | 1.062 min**; m/z = 520.2 |
| 39 | C₂H₅ | C₂H₅ | Cl | Cl | CHF₂ | 1.144 min**; m/z = 549.9 |
| 40 | CH(CH₃)₂ | CH(CH₃)₂ | Cl | Cl | CHF₂ | 1.240 min**; m/z = 578.0 |
| 41 | C₂H₅ | C₂H₅ | Br | Cl | CHF₂ | 1.148 min**; m/z = 594.1 |
| 42 | CH(CH₃)₂ | CH(CH₃)₂ | Br | Cl | CHF₂ | 1.205 min**; m/z = 622.2 |
| 43 | C₂H₅ | C₂H₅ | Br | Br | CHF₂ | 1.171 min**; m/z = 638.1 |

-continued

| Ex. | $R^6$ | $R^7$ | $R^3$ | $R^4$ | $R^1$ | HPLC/MS-Log P |
|---|---|---|---|---|---|---|
| 44 | $CH(CH_3)_2$ | $CH(CH_3)_2$ | Br | Br | $CHF_2$ | 1.245 min**; m/z = 666.1 |
| 45 | $C_2H_5$ | $C_2H_5$ | $CF_3$ | Cl | $CHF_2$ | |
| 46 | $CH(CH_3)_2$ | $CH(CH_3)_2$ | $CF_3$ | Cl | $CHF_2$ | |
| 47 | $C_2H_5$ | $C_2H_5$ | $CF_3$ | Br | $CHF_2$ | |
| 48 | $CH(CH_3)_2$ | $CH(CH_3)_2$ | $CF_3$ | Br | $CHF_2$ | |
| 49 | $C_2H_5$ | $C_2H_5$ | Br | $CF_3$ | $CHF_2$ | |
| 50 | $CH(CH_3)_2$ | $CH(CH_3)_2$ | Br | $CF_3$ | $CHF_2$ | |
| 51 | $C_2H_5$ | $C_2H_5$ | Cl | $CF_3$ | $CHF_2$ | |
| 52 | $CH(CH_3)_2$ | $CH(CH_3)_2$ | Cl | $CF_3$ | $CHF_2$ | |
| 53 | $C_2H_5$ | $C_2H_5$ | Cl | CN | $CHF_2$ | |
| 54 | $CH(CH_3)_2$ | $CH(CH_3)_2$ | Cl | CN | $CHF_2$ | |
| 55 | $C_2H_5$ | $C_2H_5$ | $CH_3$ | CN | $CHF_2$ | 3.035 min*; m/z = 519.0 |
| 56 | $CH(CH_3)_2$ | $CH(CH_3)_2$ | $CH_3$ | CN | $CHF_2$ | 3.277 min*; m/z = 547.1 |

*Analytical HPLC column: RP-18 column Chromolith Speed ROD from Merck KgaA, Germany). Elution: acetonitrile + 0.1% trifluoroacetic acid (TFA)/water + 0.1% trifluoroacetic acid (TFA) in a ratio of from 5:95 to 95:5 in 5 minutes at 40° C..
**Analytical UPLC column: Phenomenex Kinetex 1.7 μm XB-C18 100A; 50 × 2.1 mm; mobile phase: A: water + 0.1% trifluoroacetic acid (TFA); B: acetonitrile + 0.1% TFA; gradient: 5-100% B in 1.50 minutes; 100% B 0.20 min; flow: 0.8-1.0 mL/min in 1.50 minutes at 60° C..
***logP determinations were performed via capillary electrophorese on a cePro9600 ™ from CombiSep.

Example 57

2-(3-chloropyridin-2-yl)-N-[4-chloro-2-methyl-6-[(diethyl-$\lambda^4$-sulfanylidene)carbamoyl]phenyl]-5-(trifluoromethyl)pyrazole-3-carboxamide A 40 L-reactor was charged with 5.5 kg (94% pure, 20.9 mol) of 1-(3-chloropyridin-2-yl)-3-trifluoromethyl-1H-pyrazole in 5.5 L dimethoxyethane (water content below 100 ppm). The temperature was adjusted to 0° C. and 22.0 L of a 2 M solution (44.0 mol, 2.1 equiv.) of isopropyl magnesium chloride in tetrahydrofuran were added within 140 min. The mixture was stirred for 180 min at 0° C. to complete the deprotonation. Carbon dioxide was bubbled through the reaction mixture for 90 min keeping the temperature at 20° C. by external cooling until the exothermic reaction subsided. The mixture was stirred at room temperature overnight. 18 L of the solvent mixture were removed under reduced pressure (150-250 mbar). 11.5 L 1,2-dichloroethane were added and 10 L of the solvent mixture were removed by distillation at 60° C./100 mbar. This procedure was repeated twice and finally 10 L of fresh 1,2-dichloroethane were added that contained 25 mL N,N-dimethylformamide. The temperature of the mixture was adjusted to 60° C. and 9.9 kg (83.2 mol, 4.0 equiv.) thionyl chloride were added at a rate that ensured a safe handling of the gas evolution. The mixture was stirred for 3 h at 60° C. and afterwards at room temperature overnight. A precipitation of salts was observed in the course of the reaction. Excess thionyl chloride and low boilers were removed under reduced pressure (60-70° C., 100 mbar). Fresh 1,2-dichloroethane was added three times (10-20 L each time) when stirring became difficult. Finally 6 L 1,2-dichloroethane were added and the solids removed by filtration. The solids were washed twice with 10 L 1,2-dichloroethane. The obtained solution (45.4 kg) was used directly in the next step.

A 80 L-reactor was charged with 3.57 kg (13.1 mol) of 2-amino-5-chloro-3-methyl-N-(diethyl-$\lambda^4$-sulfanylidene)benzamide in 35.5 kg 1,2-dichloroethane followed by 3.13 kg (31.0 mol) triethylamine. The solution of 2-(3-chloropyridin-2-yl)-5-trifluoromethyl-2H-pyrazole-3-carbonyl chloride obtained in the previous step was added in portions (in total 44 kg) until HPLC showed complete conversion of the 2-amino-5-chloro-3-methyl-N-(diethyl-$\lambda^4$-sulfanylidene)benzamide. The mixture was stirred for 60 h at room temperature. The mixture was washed with 10 L 1% aqueous hydrochloric acid, 10 L 5% aqueous sodium bicarbonate solution and 10 L water successively. The aqueous phases were discarded. 38 L solvent were removed from the organic phase under reduced pressure (50° C., 100 mbar). 25 L methyl tert-butyl ether were added and the mixture was stirred at room temperature overnight. The temperature was adjusted to 10° C. and the precipitated product removed by filtration. The residue was washed with 5 L methyl tert-butyl ether and dried in a stream of nitrogen. Yield 3.8 kg (93.2% pure, 6.5 mol, 31% based on 1-(3-chloropyridin-2-yl)-3-trifluoromethyl-1H-pyrazole). Additional 600 g product were present in the mother liquor.

Characterization by HPLC: 4.36 min.

*Analytical HPLC column: Zorbax Eclipse XDB-C18, 1.8 μm 50*4.6 mm, Agilent. Elution: acetonitrile/water+ 0.1% phosphoric acid in a ratio from 25:75 to 100:0 in 7 minutes at 30° C., 250 bar, flow rate 1.5 mL/min.

Characterization by $^1$H-NMR (500 MHz, DMSO) [delta]: 10.87 (s, 1H), 8.53 (d, 1H), 8.22 (d, 1H), 7.75 (s, 1H), 7.65 (m, 2H), 7.40 (s, 1H), 3.09 (m, 2H), 2.92 (m, 2H) 1.15 (m, 6H).

Example 58a 2-(3-chloro-2-pyridyl)-N-[2,4-dichloro-6-[(diethyl-$\lambda^4$-sulfanylidene)carbamoyl]phenyl]-5-(trifluoromethyl)pyrazole-3-carboxamide To a solution of 2-amino-3,5-dichloro-N-(diethyl-$\lambda^4$-sulfanylidene)benzamide (8.82 g, 25.6 mmol) in pyridine (30 mL) was added N,N-dimethylamino pyridine (312 mg, 2.56 mmol, 10.0 mol %). At 90° C., a solution of 2-(3-chloro-2-pyridyl)-5-(trifluoromethyl)pyrazole-3-carbonyl chloride (10.90 g, 29.12 mmol, 1.100 equiv.) in pyridine (50 mL) was added dropwise and the mixture was stirred for 1 h. The mixture was cooled and concentrated in vacuum. Water was added and the mixture was extracted with ethyl acetate. Combined organic layers were washed with water and brine, dried over sodium sulphate, filtered and concentrated in vacuum. Flash-chromatography on silica gel yielded the title compound (4.12 g, 28%). Characterization by $^1$H-NMR (400 MHz, DMSO-$d_6$): δ [delta]=1.13 (t, 6H), 2.91 (m, 2H), 3.08 (m, 2H), 7.67 (dd, 1H), 7.77 (s, 2H), 7.89 (s, 1H), 8.22 (d, 1H), 8.51 (d, 1H), 10.73 (s, 1H).

Example 58b 2-(3-chloro-2-pyridyl)-N-[2,4-dichloro-6-[(diethyl-$\lambda^4$-sulfanylidene)carbamoyl]phenyl]-5-(trifluoromethyl)pyrazole-3-carboxamide To a suspension of potassium carbonate (7.78 g, 56.3 mmol, 1.10 equiv) and 2-amino-3,5-dichloro-N-(diethyl-$\lambda^4$-sulfanylidene)benzamide (15.00 g, 51.16 mmol) in toluene (50 mL) was added a solution of 2-(3-chloro-2-pyridyl)-5-(trifluoromethyl)pyrazole-3-carbonyl chloride (17.62 g, 51.15 mmol, 1.000 equiv.) in toluene (55 mL) at 60° C. After 1.5 h at this temperature, the mixture was cooled and water was added. The resulting precipitate was collected by filtration, washed with water and petrol ether and dried to obtain the title compound (18.73 g, 65%).

Characterization by $^1$H-NMR (400 MHz, DMSO-d$_6$): δ [delta]=1.13 (t, 6H), 2.91 (m, 2H), 3.08 (m, 2H), 7.67 (dd, 1H), 7.77 (s, 2H), 7.89 (s, 1H), 8.22 (d, 1H), 8.51 (d, 1H), 10.73 (s, 1H).

Example 59a

Synthesis of 2-(3-chloro-2-pyridyl)-N-[2,4-dichloro-6-[(bis-2-propyl-λ$^4$-sulfanylidene)carbamoyl]phenyl]-5-(trifluoromethyl)pyrazole-3-carboxamide To a suspension of potassium carbonate (0.892 g, 6.46 mmol, 1.10 equiv) and 2-amino-3,5-dichloro-N-(bis-2-propyl-λ$^4$-sulfanylidene)benzamide (2.05 g, 5.87 mmol) in toluene (30 mL) was added a solution of 2-(3-chloro-2-pyridyl)-5-(trifluoromethyl)pyrazole-3-carbonyl chloride (2.02 g, 5.87 mmol, 1.00 equiv.) in toluene (20 mL) at 60° C. After 45 min at this temperature, the mixture was cooled and water was added. The resulting precipitate was collected by filtration, washed with water and toluene and dried to obtain the title compound (3.07 g, 84%).

Characterization by UPLC-MS: 1.395 min, M=602.1 (Analytical UPLC column: Phenomenex Kinetex 1.7 µm XB-C18 100 A; 50×2.1 mm; mobile phase: A: water+0.1% trifluoroacetic acid (TFA); B: acetonitrile+0.1% TFA; gradient: 5-100% B in 1.50 minutes; 100% B 0.20 min; flow: 0.8-1.0 mL/min in 1.50 minutes at 60° C.)

Example 59b

Synthesis of 2-(3-chloro-2-pyridyl)-N-[2,4-dichloro-6-[(bis-2-propyl-λ$^4$-sulfanylidene)carbamoyl]phenyl]-5-(trifluoromethyl)pyrazole-3-carboxamide To a solution of 6,8-dichloro-1H-3,1-benzoxazine-2,4-dione (2.50 g, 10.8 mmol) in anhydrous propylene carbonate (20 mL) was added bis-2-methylpropyl sulfinium sulfate (2.75 g, 7.53 mmol, 0.70 equiv.) and triethyl amine (1.14 g, 11.3 mmol, 1.10 equiv.) at room temperature. The mixture was stirred for 3 h. ⅓ of the resulting mixture was transferred to a separate reaction flask and used for the next transformation as such.

To a solution of the above obtained solution of 2-amino-3,5-dichloro-N-(bis-2-propyl-λ$^4$-sulfanylidene)benzamide (6.7 mL; ~3.6 mmol) was added potassium carbonate (0.60 g, 4.3 mmol, 1.20 equiv) and a solution of 2-(3-chloro-2-pyridyl)-5-(trifluoromethyl)pyrazole-3-carbonyl chloride (1.34 g, 4.31 mmol, 1.20 equiv.) in toluene (10 mL) at room temperature. After 6 h at this temperature, the mixture pured onto water and treated with a small amount of ethanol under sonification. The resulting precipitate was collected by filtration, washed with water and diisopropyl ether and dried to obtain the title compound (1.29 g, 60%).

Characterization by $^1$H-NMR (400 MHz, DMSO-d$_6$):
δ [delta]=1.18 (d, 6H), 1.22 (d, 6H), 3.30 (m, 2H), 7.68 (dd, 1H), 7.75 (m, 2H), 7.81 (s, 1H), 8.21 (d, 1H), 8.54 (d, 1H), 10.76 (s, 1H).

Example 60

2-(3-chloro-2-pyridyl)-N-[2-methyl-4-chloro-6-[(diethyl-λ$^4$-sulfanylidene)carbamoyl]phenyl]-5-(trifluoromethyl)pyrazole-3-carboxamide To a suspension of potassium carbonate (0.71 g, 10 mmol, 1.3 equiv) and 2-amino-3-methyl-5-chloro-N-(diethyl-λ$^4$-sulfanylidene)benzamide (1.42 g, 3.96 mmol) in propylene carbonate (20 mL) was added a solution of 2-(3-chloro-2-pyridyl)-5-(trifluoromethyl)pyrazole-3-carbonyl chloride (1.35 g, 4.35 mmol, 1.10 equiv.) in propylene carbonate (10 mL) at room temperature. After 24 h at this temperature, the mixture was poured onto water and spiked with ethanol under vigorous stirring. The resulting solids were collected by filtration and contained pure title compound (1.57 g, 73%).

$^1$H NMR (500 MHz, DMSO) [delta]: 10.87 (s, 1H), 8.53 (d, 1H), 8.22 (d, 1H), 7.75 (s, 1H), 7.65 (m, 2H), 7.40 (s, 1H), 3.09 (m, 2H), 2.92 (m, 2H) 1.15 (m, 6H).

Example 61

2-(3-chloro-2-pyridyl)-N-[2-methyl-4-chloro-6-[(di-2-propyl-λ$^4$-sulfanylidene)carbamoyl]phenyl]-5-(trifluoromethyl)pyrazole-3-carboxamide To a suspension of bis-2-isopropyl sulfinium sulfate (192 g, 0.53 mol, 0.68 equiv.) in DMSO (700 mL) a solution of 6-chloro-8-methyl-1H-3,1-benzoxazine-2,4-dione (162 g, 0.77 mol) in anhydrous DMSO (300 mL) was added at 22° C. followed by addition of triethylamine (117.4 mL, 84.75 g, 0.85 mol, 1.1 equiv.) at 22° C. The mixture was stirred for 6 h, and then added dropwise to ice-water. The mixture was extracted with dichloromethane and the combined organic layers were dried over sodium sulphate and concentrated in vacuo. The residue was triturated with diisopropyl ether to yield the title compound (189.9 g, 82%).

Characterization by $^1$H-NMR (400 MHz, CDCl$_3$): δ [delta]=1.40 (2×d, 12H), 2.11 (s, 3H), 3.23 (m, 2H), 6.05 (br. s, 2H), 7.03 (s, 1H), 8.01 (s, 1H).

To a suspension of potassium carbonate (9.73 g, 70.0 mmol, 1.10 equiv) and 2-amino-5-chloro-N-(diisopropyl-λ$^4$-sulfanylidene)-3-methyl-benzamide (18.7 g, 62.4 mmol, 1.00 equiv) in toluene (80 mL) a solution of 2-(3-chloro-2-pyridyl)-5-(trifluoromethyl)pyrazole-3-carbonyl chloride (20.1 g, 64.1 mmol, 1.03 equiv.) in toluene (40 mL) was added at 60° C. After 35 minutes at 60° C., the reaction mixture was cooled to room temperature and diluted with ethyl acetate (50 mL) and water (50 mL). The organic phase was washed with water (50 mL), 0.1 M HCl (50 mL), dried over Na$_2$SO$_4$ and concentrated to afford, after recrystallization, 24.4 g (66%) of the tile compound.

Characterization by $^1$H-NMR (400 MHz, DMSO-d$_6$): δ [delta]=1.20 (d, 6H), 1.30 (d, 6H), 2.15 (s, 3H), 3.30 (m, 2H), 7.41 (s, 1H), 7.62 (m, 2H), 7.80 (s, 1H), 8.22 (d, 1H), 8.52 (d, 1H), 10.88 (s, 1H).

The invention claimed is:
1. A process for preparing a compound of formula (I):

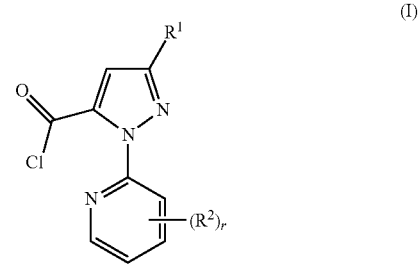

in which
R$^1$ is selected from the group consisting of hydrogen, halogen, cyano, —SF$_5$, CBrF$_2$, C$_1$-C$_6$-alkyl, C$_1$-C$_6$- fluoroalkyl, $C_3$-$C_8$-cycloalkyl, $C_3$-$C_8$-fluorocycloalkyl, $C_2$-$C_6$-alkenyl, $C_2$-$C_6$-fluoroalkenyl, wherein the six last mentioned radicals may be substituted by one or more radicals $R^a$; —Si$(R^f)_2R^g$, —OR$^b$, —SR$^b$, —S(O)$_m$R$^b$, —S(O)$_n$N($R^c$)$R^d$, —N($R^{c1}$)$R^{d1}$, phenyl which may be substituted by 1, 2, 3, 4 or 5 radicals $R^e$, and a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO and SO$_2$, as ring members, where the heterocyclic ring may be substituted by one or more radicals $R^e$;

each $R^2$ is independently selected from the group consisting of halogen, SF$_5$, $C_1$-$C_6$-alkyl, $C_1$-$C_6$-fluoroalkyl, $C_3$-$C_8$-cycloalkyl, $C_3$-$C_8$-fluorocycloalkyl, $C_2$-$C_6$-alkenyl, $C_2$-$C_6$-fluoroalkenyl, wherein the six last mentioned radicals may be substituted by one or more radicals $R^a$; —Si$(R^f)_2R^g$, —OR$^b$, —SR$^b$, —S(O)$_m$R$^b$, —S(O)$_n$N($R^c$)$R^d$, —N($R^{c1}$)$R^{d1}$, phenyl which may be substituted by 1, 2, 3, 4 or 5 radicals $R^e$, and a 3-, 4-, 5-, 6- or 7-membered saturated, partially unsaturated or completely unsaturated heterocyclic ring containing 1, 2 or 3 heteroatoms or heteroatom groups selected from the group consisting of N, O, S, NO, SO and SO$_2$, as ring members, where the heterocyclic ring may be substituted by one or more radicals $R^e$;

$R^a$ is selected from the group consisting of SF$_5$, $C_1$-$C_6$-alkyl, $C_1$-$C_6$-fluoroalkyl, $C_1$-$C_6$-alkoxy-$C_1$-$C_6$-alkyl, $C_3$-$C_8$-cycloalkyl, $C_3$-$C_8$-fluorocycloalkyl, $C_2$-$C_6$-alkenyl, $C_2$-$C_6$-fluoroalkenyl, —Si$(R^f)_2R^g$, —OR$^b$, —SR$^b$, —S(O)$_m$R$^b$, —S(O)$_n$N($R^c$)$R^d$, —N($R^{c1}$)$R^{d1}$, phenyl which may be substituted by 1, 2, 3, 4 or 5 radicals $R^e$, and a 3-, 4-, 5-, 6- or 7-membered saturated, partially unsaturated or completely unsaturated heterocyclic ring containing 1, 2 or 3 heteroatoms or heteroatom groups selected from the group consisting of N, O, S, NO, SO and SO$_2$, as ring members, where the heterocyclic ring may be substituted by one or more radicals $R^e$;

or two geminally bound radicals $R^a$ together form a group selected from the group consisting of =C$R^hR^i$, =N$R^{c1}$, =NO$R^b$ and =NN$R^{c1}$, or two radicals $R^a$, together with the carbon atoms to which they are bound, form a 3-, 4-, 5-, 6-, 7- or 8-membered saturated or partially unsaturated carbocyclic or heterocyclic ring containing 1, 2 or 3 heteroatoms or heteroatom groups selected from the group consisting of N, O, S, NO, SO and SO$_2$, as ring members;

wherein, in the case of more than one $R^a$, $R^a$ can be identical or different;

$R^b$ is selected from the group consisting of $C_1$-$C_6$-alkyl, $C_1$-$C_6$-fluoroalkyl, $C_2$-$C_6$-alkenyl, $C_2$-$C_6$-fluoroalkenyl, $C_3$-$C_8$-cycloalkyl, $C_3$-$C_8$-fluorocycloalkyl, wherein the six last mentioned radicals may optionally carry 1 or 2 radicals selected from the group consisting of $C_1$-$C_6$-alkoxy, $C_1$-$C_6$-fluoroalkoxy, $C_1$-$C_6$-fluoroalkylthio, $C_1$-$C_6$-alkylsulfinyl, $C_1$-$C_6$-fluoroalkylsulfinyl, $C_1$-$C_6$-alkylsulfonyl, $C_1$-$C_6$-fluoroalkylsulfonyl, —Si$(R^f)_2R^g$, phenyl, benzyl, pyridyl and phenoxy, wherein the four last mentioned radicals may be unsubstituted, partially or fully halogenated and/or may carry 1, 2 or 3 substituents selected from the group consisting of $C_1$-$C_6$-alkyl, $C_1$-$C_6$-fluoroalkyl, $C_1$-$C_6$-alkoxy and $C_1$-$C_6$-fluoroalkoxy;

wherein, in the case of more than one $R^b$, $R^b$ can be identical or different;

$R^c$, $R^d$ are, independently from one another and independently of each occurrence, selected from the group consisting of cyano, $C_1$-$C_6$-alkyl, $C_1$-$C_6$-fluoroalkyl, $C_2$-$C_6$-alkenyl, $C_2$-$C_6$-fluoroalkenyl, $C_3$-$C_8$-cycloalkyl, $C_3$-$C_8$-fluorocycloalkyl, wherein the six last mentioned radicals may optionally carry 1 or 2 radicals selected from the group consisting of $C_1$-$C_6$-alkoxy, $C_1$-$C_6$-fluoroalkoxy, $C_1$-$C_6$-alkylthio, $C_1$-$C_6$-fluoroalkylthio, $C_1$-$C_6$-alkylsulfinyl, $C_1$-$C_6$-alkylsulfonyl, —Si$(R^f)_2R^g$, phenyl, benzyl, pyridyl and phenoxy, wherein the four last mentioned radicals may be unsubstituted, partially or fully halogenated and/or may carry 1, 2 or 3 substituents selected from the group consisting of $C_1$-$C_6$-alkyl, $C_1$-$C_6$-fluoroalkyl, $C_1$-$C_6$-alkoxy and $C_1$-$C_6$-fluoroalkoxy;

or $R^c$ and $R^d$, together with the nitrogen atom to which they are bound, form a 3-, 4-, 5-, 6- or 7-membered saturated, partly unsaturated or completely unsaturated heterocyclic ring which may contain 1 or 2 further heteroatoms selected from the group consisting of N, O and S as ring members, where the heterocyclic ring may carry 1, 2, 3 or 4 substituents selected from the group consisting of halogen, $C_1$-$C_4$-alkyl, $C_1$-$C_4$-fluoroalkyl, $C_1$-$C_4$-alkoxy and $C_1$-$C_4$-fluoroalkoxy;

$R^{c1}$ is hydrogen or has one of the meanings given for $R^c$;
$R^{d1}$ is hydrogen or has one of the meanings given for $R^d$;
$R^e$ is selected from the group consisting of halogen, $C_1$-$C_6$-alkyl, $C_1$-$C_6$-fluoroalkyl, $C_2$-$C_6$-alkenyl, $C_2$-$C_6$-fluoroalkenyl, $C_3$-$C_8$-cycloalkyl, $C_3$-$C_8$-fluorocycloalkyl, where the six last mentioned radicals may optionally carry 1 or 2 radicals selected from the group consisting of $C_1$-$C_4$-alkoxy; $C_1$-$C_6$-alkoxy, $C_1$-$C_6$-fluoroalkoxy, $C_1$-$C_6$-alkylthio, $C_1$-$C_6$-fluoroalkylthio, $C_1$-$C_6$-alkylsulfinyl, $C_1$-$C_6$-fluoroalkylsulfinyl, $C_1$-$C_6$-alkylsulfonyl, $C_1$-$C_6$-fluoroalkylsulfonyl, —Si$(R^f)_2R^g$, phenyl, benzyl, pyridyl and phenoxy, wherein the four last mentioned radicals may be unsubstituted, partially or fully halogenated and/or may carry 1, 2 or 3 substituents selected from the group consisting of $C_1$-$C_6$-alkyl, $C_1$-$C_6$-fluoroalkyl, $C_1$-$C_6$-alkoxy and $C_1$-$C_6$-fluoroalkoxy;

wherein, in the case of more than one $R^e$, $R^e$ can be identical or different;

$R^f$, $R^g$ are, independently of each other and independently of each occurrence, selected from the group consisting of $C_1$-$C_4$-alkyl, $C_3$-$C_6$-cycloalkyl, alkyl, phenyl and benzyl;

$R^h$, $R^i$ are, independently from one another and independently of each occurrence, selected from the group consisting of hydrogen, halogen, SF$_5$, $C_1$-$C_6$-alkyl, $C_1$-$C_6$-fluoroalkyl, $C_2$-$C_6$-alkenyl, $C_2$-$C_6$-fluoroalkenyl, $C_3$-$C_8$-cycloalkyl, $C_3$-$C_8$-fluorocycloalkyl, where the six last mentioned radicals may optionally carry 1 or 2 radicals selected from the group consisting of $C_1$-$C_4$-alkyl and $C_1$-$C_4$-fluoroalkyl; $C_1$-$C_6$-alkoxy, $C_1$-$C_6$-fluoroalkoxy, $C_1$-$C_6$-alkylthio, $C_1$-$C_6$-fluoroalkylthio, $C_1$-$C_6$-alkylsulfinyl, $C_1$-$C_6$-alkylsulfonyl, —Si$(R^f)_2R^g$, phenyl, benzyl, pyridyl and phenoxy, wherein the four last mentioned radicals may be unsubstituted, partially or fully halogenated and/or may carry 1, 2 or 3 substituents selected from the group consisting of $C_1$-$C_6$-alkyl, $C_1$-$C_6$-fluoroalkyl, $C_1$-$C_6$-alkoxy, $C_1$-$C_6$-fluoroalkoxy, ($C_1$-$C_6$-alkoxy)carbonyl, ($C_1$-$C_6$-alkyl)amino and di-($C_1$-$C_6$-alkyl)amino;

m is 1 or 2, wherein, in the case of several occurrences, m may be identical or different;

n is 0, 1 or 2; wherein, in the case of several occurrences, n may be identical or different;

r is 0, 1, 2, 3 or 4;

comprising i) deprotonating a compound of the formula (II)

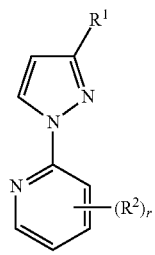
(II)

in which the variables $R^1$, $R^2$ and r are each as defined above, with a magnesium-organic base having a carbon bound magnesium; and ii) subjecting the product obtained in step (i) to a carboxylation by reacting it with carbon dioxide or a carbon dioxide equivalent, to obtain a compound of formula (I-A):

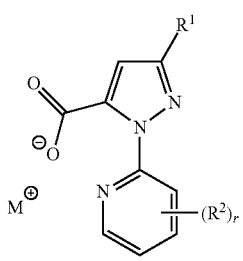
(I-A)

wherein $M^+$ is a cation or cation equivalent compensating the charge of the carboxylate; and wherein the carboxylate compound of formula I-A is converted in a step (ii-a) to the corresponding carbonyl chloride compound of formula (I):

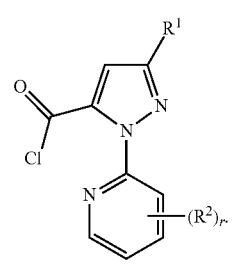
(I)

2. The process according to claim 1, wherein the carboxylate compound of formula I-A is further converted in a step (ii-b) to the corresponding acid compound (I-B):

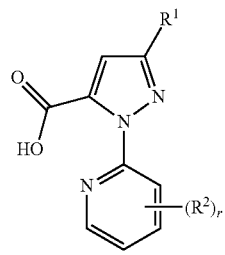
(I-B)

in which the variables $R^1$, $R^2$ and r are each as defined in claim 1, and wherein the acid compound I-B is further converted in a step (ii-c) to the corresponding carbonyl chloride compound (I):

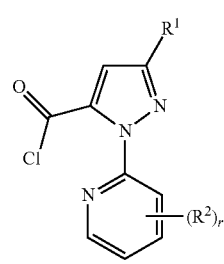
(I)

in which the variables $R^1$, $R^2$ and r are each as defined in claim 1.

3. The process according to claim 1, in which the conversion of a compound of formula (II) to a carboxylate compound of formula (I-A) in steps i and ii is done in an aprotic organic solvent or aprotic solvent mixture comprising an aprotic solvent having an ether moiety.

4. The process according to claim 2, in which the conversion of the compound of formula I-A or I-B to the carbonylchloride compound of formula I (step or step ii-b and ii-c) is done in a non-polar solvent.

5. The process according to claim 1, wherein $R^1$ is selected from the group consisting of halogen, $C_1$-$C_4$-fluoroalkyl, $C_1$-$C_4$-alkoxy and $C_1$-$C_4$-fluoroalkoxy-$C_1$-$C_4$-alkyl.

6. The process according to claim 1, wherein
r is 1, and
$R^2$ is located in position 3 of the pyridyl moiety of the compound of the formula (I).

7. The process according to claim 1, wherein the base is selected from the group consisting of $C_1$-$C_6$-alkyl magnesium halide and $C_5$-$C_6$-cycloalkyl magnesium halide.

8. The process according to claim 1, wherein the compound of formula II is obtained by reacting a compound of formula (III) with a compound of the formula (IV)

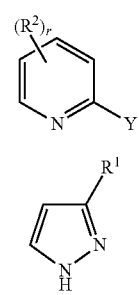
(III)

(IV)

in which

R$^1$, R$^2$ and r are as defined in claim 1; and

Y is selected from the group consisting of halogen, C$_1$-C$_3$-alkoxy, C$_1$-C$_3$-alkylthio, C$_1$-C$_3$-haloalkoxy, C$_1$-C$_3$-haloalkylthio, —S(O)R$^b$, —S(O)$_2$R$^b$, —OS(O) R$^b$, —OS(O)$_2$R$^b$ and —NO$_2$, where R$^b$ is as defined in claim 1;

in the presence of a base.

9. The process according to claim 8, wherein the compound of formula (IV) is obtained by reacting a compound of formula (V)

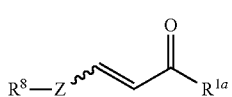

(V)

in which

R$^{1a}$ has one of the meanings given for R$^1$ in claim 1 with the exception of halogen, cyano and —SF$_5$;

Z is O, S or NR$^9$; and

R$^8$ is selected from the group consisting of C$_1$-C$_6$-alkyl, C$_3$-C$_8$-cycloalkyl, C$_1$-C$_6$-haloalkyl and C$_1$-C$_6$-cyclohaloalkyl;

R$^9$ if present, is selected from the group consisting of C$_1$-C$_6$-alkyl, C$_3$-C$_8$-cycloalkyl, C$_1$-C$_6$-haloalkyl and C$_1$-C$_6$-cyclohaloalkyl or for Z being NR$^9$ the moiety Z—R$^8$ may also form a 5- to 7-membered saturated N-bound heterocycle, which in addition to the nitrogen atom may have one further heteroatom or heteroatom moiety as ring member, where the further heteroatom or heteroatom moiety is selected from the group consisting of O, S and N—(C$_1$-C$_4$-alkyl);

with hydrazine, or its salts or its hydrates.

10. A process for preparing a compound of formula (VI)

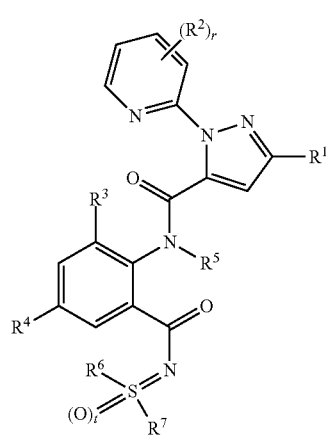

(VI)

in which

R$^1$ is selected from the group consisting of hydrogen, halogen, cyano, —SF$_5$, CBrF$_2$, C$_1$-C$_6$-alkyl, C$_1$-C$_6$-fluoroalkyl, C$_3$-C$_8$-cycloalkyl, C$_3$-C$_8$-fluorocycloalkyl, C$_2$-C$_6$-alkenyl, C$_2$-C$_6$-fluoroalkenyl, wherein the six last mentioned radicals may be substituted by one or more radicals R$^a$; —Si(R$^f$)$_2$R$^g$, —OR$^b$, —SR$^b$, —S(O)$_m$R$^b$, —S(O)$_n$N(R$^c$)R$^d$, —N(R$^{c1}$)R$^{d1}$ phenyl which may be substituted by 1, 2, 3, 4 or 5 radicals R$^e$, and a 3-, 4-, 5-, 6- or 7-membered saturated, partially unsaturated or aromatic heterocyclic ring containing 1, 2 or 3 heteroatoms or heteroatom groups selected from the group consisting of N, O, S, NO, SO and SO$_2$, as ring members, where the heterocyclic ring may be substituted by one or more radicals R$^e$;

each R$^2$ is independently selected from the group consisting of halogen, SF$_5$, C$_1$-C$_6$-alkyl, C$_1$-C$_6$-fluoroalkyl, C$_3$-C$_8$-cycloalkyl, C$_3$-C$_8$-fluorocycloalkyl, C$_2$-C$_6$-alkenyl, C$_2$-C$_6$-fluoroalkenyl, wherein the six last mentioned radicals may be substituted by one or more radicals R$^a$; —Si(R$^f$)$_2$R$^g$, —OR$^b$, —SR$^b$, —S(O)$_m$R$^b$, —S(O)$_n$N(R$^c$)R$^d$, —N(R$^{c1}$)R$^{d1}$, phenyl which may be substituted by 1, 2, 3, 4 or 5 radicals R$^e$, and a 3-, 4-, 5-, 6- or 7-membered saturated, partially unsaturated or completely unsaturated heterocyclic ring containing 1, 2 or 3 heteroatoms or heteroatom groups selected from the group consisting of N, O, S, NO, SO and SO$_2$, as ring members, where the heterocyclic ring may be substituted by one or more radicals R$^e$;

R$^3$ and R$^4$ are independently selected from the group consisting of halogen, cyano, azido, nitro, —SCN, SF$_5$, C$_1$-C$_6$-alkyl, C$_1$-C$_6$-haloalkyl, C$_3$-C$_8$-cycloalkyl, C$_3$-C$_8$-halocycloalkyl, C$_2$-C$_6$-alkenyl, C$_2$-C$_6$-haloalkenyl, C$_2$-C$_6$-alkynyl, C$_2$-C$_6$-haloalkynyl, wherein the eight last mentioned radicals may be substituted by one or more radicals R$^a$; —Si(R$^f$)$_2$R$^g$, —OR$^{b1}$, —OS(O)$_n$R$^{b1}$, —SR$^{b1}$, —S(O)$_m$R$^{b1}$, —S(O)$_n$N(R$^{c1}$)R$^{d1}$, —N(R$^{c1}$) R$^{d1}$, —N(R$^{c1}$)C(=O)R$^a$, —C(=O)R$^a$, —C(=O) OR$^{b1}$, —C(=S)R$^a$, —C(=S)OR$^{b1}$, —C(=NR$^{c1}$) R$^a$, —C(=O)N(R$^{c1}$)R$^{d1}$, —C(=S)N(R$^{c1}$)R$^{d1}$, phenyl which may be substituted by 1, 2, 3, 4 or 5 radicals R$^e$, and a 3-, 4-, 5-, 6- or 7-membered saturated, partially unsaturated or completely unsaturated heterocyclic ring containing 1, 2 or 3 heteroatoms or heteroatom groups selected from the group consisting of N, O, S, NO, SO and SO$_2$, as ring members, where the heterocyclic ring may be substituted by one or more radicals R$^e$;

R$^5$ is selected from the group consisting of hydrogen, cyano, C$_1$-C$_{10}$-alkyl, haloalkyl, C$_3$-C$_8$-cycloalkyl, C$_3$-C$_8$-halocycloalkyl, C$_2$-C$_{10}$-alkenyl, C$_2$-C$_{10}$-haloalkenyl, C$_2$-C$_{10}$-alkynyl, C$_2$-C$_{10}$-haloalkynyl, wherein the eight last radicals may optionally be substituted by one or more radicals R$^a$; —N(R$^{c1}$)R$^{d1}$, —Si(R$^f$)$_2$R$^g$, —OR$^{b1}$, —SR$^{b1}$, —S(O)$_m$R$^{b1}$, —S(O)$_n$N (R$^{c1}$)R$^{d1}$, —C(=O)R$^a$, —C(=O)OR$^{b1}$, —C(=O) N(R$^{c1}$)R$^{d1}$, —C(=S)R$^a$, —C(=S)OR$^{b1}$, —C(=S) N(R$^{c1}$)R$^{d1}$, —C(=NR$^{c1}$)R$^a$, phenyl which may be substituted by 1, 2, 3, 4 or 5 radicals R$^e$, and a 3-, 4-, 5-, 6- or 7-membered saturated, partially unsaturated or completely unsaturated heterocyclic ring containing 1, 2 or 3 heteroatoms or heteroatom groups selected from the group consisting of N, O, S, NO, SO and SO$_2$, as ring members, where the heterocyclic ring may be substituted by one or more radicals R$^e$;

R$^6$ and R$^7$ are selected independently of one another from the group consisting of hydrogen, C$_1$-C$_{10}$-alkyl, C$_1$-C$_{10}$-haloalkyl, C$_3$-C$_8$-cycloalkyl, C$_3$-C$_8$-halocycloalkyl, C$_2$-C$_{10}$-alkenyl, C$_2$-C$_{10}$-haloalkenyl, C$_2$-C$_{10}$-alkynyl, C$_2$-C$_{10}$-haloalkynyl, wherein the eight last radicals may optionally be substituted by one or more radicals R$^a$;

or R$^6$ and R$^7$ together represent a C$_2$-C$_7$-alkylene, C$_2$-C$_7$-alkenylene or C$_6$-C$_9$-alkynylene chain forming together with the sulfur atom to which they are attached a 3-, 4-, 5-, 6-, 7-, 8-, 9- or 10-membered saturated, partially unsaturated or completely unsaturated ring, wherein 1 to 4 of the CH$_2$ groups in the C$_2$-C$_7$-alkylene chain or 1 to 4 of any of the CH$_2$ or CH groups in the $C_2$-$C_7$-alkenylene chain or 1 to 4 of any of the $CH_2$ groups in the $C_6$-$C_9$-alkynylene chain may be replaced by 1 to 4 groups independently selected from the group consisting of C=O, C=S, O, S, N, NO, SO, $SO_2$ and NH, and wherein the carbon and/or nitrogen atoms in the $C_2$-$C_7$-alkylene, $C_2$-$C_7$-alkenylene or $C_6$-$C_9$-alkynylene chain may be substituted with 1 to 5 substituents independently selected from the group consisting of halogen, cyano, $C_1$-$C_6$-alkyl, $C_1$-$C_6$-alkoxy, $C_1$-$C_6$-haloalkoxy, $C_1$-$C_6$-haloalkylthio, $C_3$-$C_8$-cycloalkyl, $C_3$-$C_8$-halocycloalkyl, $C_2$-$C_6$-alkenyl, $C_2$-$C_6$-haloalkenyl, $C_2$-$C_6$-alkynyl, $C_2$-$C_6$-haloalkynyl; said substituents being identical or different from one another if more than one substituent is present;

$R^a$, $R^b$, $R^c$, $R^{c1}$, $R^d$, $R^{d1}$, $R^e$, $R^f$, $R^g$, m and n are each as defined in claim 1;

$R^{b1}$ is hydrogen or has one of the meanings given for $R^b$ in claim 1; and t is 0 or 1; and r is 0, 1, 2, 3 or 4;

which comprises preparing a compound of the formula (I) according to claim 1 and subsequently iii) reacting the compound of the formula (I) with a compound of the formula (VII)

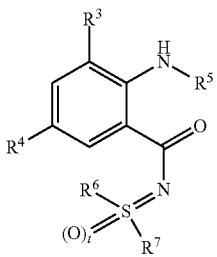

(VII)

in which the variables $R^3$, $R^4$, $R^5$, $R^6$, $R^7$ and t are each as defined above, in the presence of a base, to obtain a compound of the formula VI.

11. The process according to claim 10, wherein $R^3$ and $R^4$ are independently selected from the group consisting of halogen, cyano, $C_1$-$C_4$-alkyl and $C_1$-$C_4$-haloalkyl.

12. The process according to claim 10, wherein $R^3$ is selected from the group consisting of halogen, methyl and halomethyl, and $R^4$ is selected from the group consisting of halogen, cyano, methyl and halomethyl.

13. The process according to claim 11, wherein t is 0, and $R^6$ and $R^7$ are selected independently of one another from $C_1$-$C_6$-alkyl, or $R^6$ and $R^7$ together represent a $C_3$-$C_6$-alkylene chain forming together with the sulfur atom to which they are attached a 4-, 5-, 6- or 7-membered saturated ring.

14. The process according to claim 5, wherein $R^1$ is selected from the group consisting of halogen, $CF_3$, $CHF_2$ and methoxy.

15. The process according to claim 6, wherein r is 1, and $R^2$ is located in position 3 of the pyridyl moiety of the compound of the formula (I) and is selected from the group consisting of halogen and $CF_3$.

16. The process according to claim 4, in which the non-polar solvent is selected from the group consisting of dichloromethane, dichloroethane, toluene, chlorobenzene and mixtures thereof.

* * * * *